US012617818B2

(12) United States Patent
Root

(10) Patent No.: US 12,617,818 B2
(45) Date of Patent: May 5, 2026

(54) COMPOSITIONS AND METHODS FOR MODULATING MYOSIN SUBFRAGMENT-2 COILED COIL STABILITY AND METHODS FOR USING THEM

(71) Applicant: UNIVERSITY OF NORTH TEXAS, Denton, TX (US)

(72) Inventor: Douglas Root, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 883 days.

(21) Appl. No.: 17/914,277

(22) PCT Filed: Mar. 25, 2021

(86) PCT No.: PCT/US2021/024126
§ 371 (c)(1),
(2) Date: Sep. 23, 2022

(87) PCT Pub. No.: WO2021/195361
PCT Pub. Date: Sep. 30, 2021

(65) Prior Publication Data
US 2023/0227502 A1      Jul. 20, 2023

Related U.S. Application Data

(60) Provisional application No. 62/994,723, filed on Mar. 25, 2020.

(51) Int. Cl.
| | |
|---|---|
| *C07K 7/08* | (2006.01) |
| *A61K 38/00* | (2006.01) |
| *A61K 48/00* | (2006.01) |
| *A61P 9/04* | (2006.01) |

(52) U.S. Cl.
CPC ............ *C07K 7/08* (2013.01); *A61K 48/0066* (2013.01); *A61K 48/0075* (2013.01); *A61P 9/04* (2018.01); *A61K 38/00* (2013.01)

(58) Field of Classification Search
None
See application file for complete search history.

(56) References Cited

U.S. PATENT DOCUMENTS

2018/0217162 A1      8/2018   Fu et al.

OTHER PUBLICATIONS

NCBI Entry ELW69260.1 (Year: 2015).*
NCBI Entry MFK9479287.1 (Year: 2024).*
Tanner et al. Anti-S2 Peptides Modulate Myosin Coiled Coil Structure and Shift Force-PCa Curves in Human Cardiac Muscle. Biophysical Journal, Feb. 15, 2019, vol. 116, No. 3, Supplement 1, pp. 1a-580a.

* cited by examiner

*Primary Examiner* — Sudhakar Katakam
*Assistant Examiner* — Zachary J Miknis
(74) *Attorney, Agent, or Firm* — Gregory P. Einhorn; Greer, Burns & Crain, Ltd.

(57) ABSTRACT

In alternative embodiments, provided are peptides and peptide-comprising compositions, including products of manufacture and kits, and methods, for modulating myosin subfragment-2 coiled coil stability. In alternative embodiments, a peptide modulator of myosin subfragment-2 coiled coil stability as provided herein is administered to an individual in need thereof for: increasing exercise tolerance in a subject with heart failure; reducing hospitalization in a subject with heart failure; improving quality of life in a subject with heart failure; decreasing morbidity in a subject with heart failure; decreasing mortality in a subject with heart failure; modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies.

18 Claims, 41 Drawing Sheets
Specification includes a Sequence Listing.

Myofibrilar Contractility Assay

Edge of Coverslip (Immobile)

Glass bead (Mobile)

FIG. 55

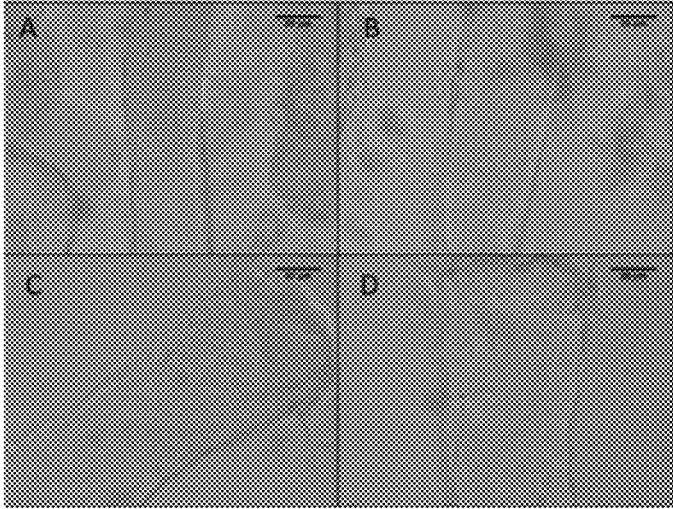

Figure 55A: Labeled destabilizer before ATP ~ 40 nM, Figure 55B: Labeled
Destabilizer after ATP ~ 40 nM, % Contraction: 25%; Figure 55C:
Labeled Stabilizer before ATP ~ 40 nM, Figure 55D: Labeled Stabilizer
after ATP ~ 40 nM, % Contraction: 13%

FIG. 56

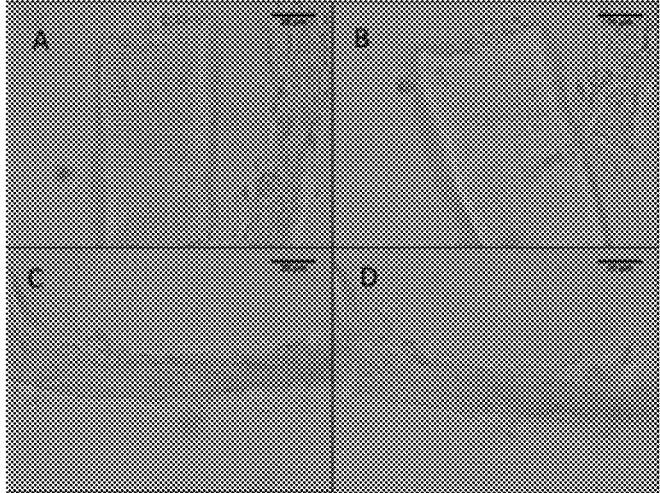

Figure 56A: Unlabeled destabilizer before ATP ~ 40 nM, Figure 56B:
Unlabeled Destabilizer after ATP ~ 40 nM, % Contraction: 30%; Figure
56C: Unlabeled stabilizer before ATP ~ 40 nM, Figure 56D: Unlabeled
Stabilizer after ATP ~ 40 nM, % Contraction: 11%

COMPOSITIONS AND METHODS FOR MODULATING MYOSIN SUBFRAGMENT-2 COILED COIL STABILITY AND METHODS FOR USING THEM

RELATED APPLICATIONS

This U.S. National Phase Patent Applications claims benefit of priority under 35 U.S.C. § 371 to Patent Convention Treaty (PCT) International Application PCT/US2021/024503, filed Mar. 26, 2021, which claims the benefit of priority under 35 U.S.C. § 119 (e) of U.S. Provisional Patent Application Ser. No. 63/994,723, filed Mar. 25, 2020. The aforementioned applications are expressly incorporated herein by reference in their entirety and for all purposes.

REFERENCE TO SEQUENCE LISTING

This application includes an electronically submitted sequence listing in .txt format. The .txt file contains a sequence listing entitled "6343.140271_ST25.txt" created on Nov. 10, 2025 and is 5,272 bytes in size. The sequence listing contained in this .txt file is part of the specification and is hereby incorporated by reference herein in its entirety.

TECHNICAL FIELD

This invention generally relates to cell biology and medicine. In alternative embodiments, provided are peptides and peptide-comprising compositions, including products of manufacture and kits, and methods, for modulating myosin subfragment-2 coiled coil stability. In alternative embodiments, a peptide modulator of myosin subfragment-2 coiled coil stability as provided herein is administered to an individual in need thereof for: increasing exercise tolerance in a subject with heart failure; reducing hospitalization in a subject with heart failure; improving quality of life in a subject with heart failure; decreasing morbidity in a subject with heart failure; decreasing mortality in a subject with heart failure; modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies.

BACKGROUND

Every day, approximately 2200 Americans die of cardiovascular disease. In fact, cardiovascular disease is the leading global cause of death, representing 31 percent of deaths around the world (Roger et al., 2012). Many types of heart disease contribute to these staggering/appalling statistics, and among them are hypertrophic cardiomyopathy (HCM), dilated cardiomyopathy (DCM), and chronic congestive heart failure (CHF). Although these diseases all are caused by different genetic mutations in the affected individual, they all render the heart incapable of effectively pumping blood to the body, leading to arrhythmia and cardiac failure (Miller et al., 2015; Reed & Sueta, 2015; Choudhry et al., 2019).

The most prevalent methods of treating arrhythmias and conduction defects involve implantation of a pacemaker or an implantable cardioverter-defibrillator (ICD) (Miller et al., 2015). While such methods are largely effective, they require invasive surgery to perform their function, which may lead to complications. Other popular methods of treatment for heart failures include angiotensin-converting enzyme (ACE) inhibitors, beta-blocking agents, diuretics, and digoxin (Reed & Sueta, 2015). However, these drug treatments lose potency as a patient acquires drug tolerance and requires higher doses, increasing the chance of side effects (Rickenbacher, P., 2011). A non-invasive and novel treatment for HCM, DCM, and CHF that directly affects the actin-myosin interaction at a biochemical level could alleviate these problems.

SUMMARY

In alternative embodiments, provided are synthetic or recombinant peptides comprising or consisting of an amino acid sequence:

(a) EMNERLEDEREMKAELTAK (SEQ ID NO:1), with L or D amino acid isomers;

(b) having the formula: $(K)_x$-FKA-$(K)_y$, or $(Lys)_x$-Phe-Lys-Ala-$(Lys)_y$ (SEQ ID NO: 2) wherein x and y are independently integers between 5 and 20, or x and y are independently 3, 4, 5, 6, 7, 8, 9, 10, 11, 12, 13, 14, 15, 16, 17, 18, 19 or 20, with L or D amino acid isomers, wherein optionally the peptide comprises or consists of an amino acid sequence: KKKKKKKKFKAKKKKKK (SEQ ID NO:3), with L or D amino acid isomers; or (c) a mimetic or peptidomimetic of (a) or (b), or a peptide of (a) or (b) having at least one, or comprising 1, 2, 3, 4, 5, 6, 7, 8, 9 or 10 or more conservative amino acid substitutions.

In alternative embodiments, provided are synthetic or recombinant nucleic acids encoding a synthetic or recombinant peptide as provided herein.

In alternative embodiments, provided are expression vehicles comprising the synthetic or recombinant nucleic acid as provided herein.

In alternative embodiments, provided are isolated or recombinant cells comprising the synthetic or recombinant peptide as provided herein, or the synthetic or recombinant nucleic acid as provided herein, or the expression vehicle as provided herein.

In alternative embodiments, provided are products of manufacture comprising: the synthetic or recombinant peptide as provided herein, or the synthetic or recombinant nucleic acid as provided herein, or the expression vehicle as provided herein, wherein optionally the product of manufacture is a pharmaceutical formulation, optionally formulated in a buffer, in a saline solution, in a powder, an emulsion, in a vesicle, in a liposome, in a nanoparticle, in a nanolipoparticle or equivalents thereof.

In alternative embodiments, provided are methods for:

treating, ameliorating or protecting (preventing), slowing the progress of, abating or decreasing one or more symptoms of, or reversing; hypertrophic cardiomyopathy (HCM), dilated cardiomyopathy (DCM), and chronic congestive heart failure (CHF)

increasing exercise tolerance in a subject with heart failure;

reducing hospitalization in a subject with heart failure;

improving quality of life in a subject with heart failure;

decreasing morbidity in a subject with heart failure;

decreasing mortality in a subject with heart failure;

modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies, in an individual or a patient in need thereof, the method comprising administering a peptide modulator of myosin subfragment-2 coiled coil stability, or a nucleic acid encoding the peptide modulator of myosin subfragment-2 coiled coil stability, to the individual in need thereof, wherein the peptide modulator of myosin subfragment-2 coiled coil stability comprises a peptide as provided herein, or the nucleic acid encoding the peptide modulator of myosin subfragment-2 coiled coil stability comprises a nucleic acid as provided herein.

In alternative embodiments of methods as provided herein:

a nucleic acid encoding the peptide modulator of myosin subfragment-2 coiled coil stability is operatively linked to a transcriptional regulatory sequence; or an expression vehicle, a vector, a recombinant virus, or equivalent, having contained therein a peptide modulator of myosin subfragment-2 coiled coil stability-encoding nucleic acid or gene, or a peptide modulator of myosin subfragment-2 coiled coil stability-expressing nucleic acid, transcript or message, and the expression vehicle, vector, recombinant virus, or equivalent can express the peptide modulator of myosin subfragment-2 coiled coil stability-encoding nucleic acid, gene, transcript or message in a cell or in vivo; and optionally the method comprises administering or delivering the peptide modulator of myosin subfragment-2 coiled coil stability-encoding nucleic acid, gene, transcript or message operatively linked to a transcriptional regulatory sequence, or the expression vehicle, vector, recombinant virus, or equivalent, to the cell, or an individual or a patient in need thereof;

the expression vehicle, vector, recombinant virus, or equivalent is or comprises: an adeno-associated virus (AAV), a lentiviral vector or an adenovirus vector, an AAV serotype AAV5, AAV6, AAV8 or AAV9, a rhesus-derived AAV, or the rhesus-derived AAV AAVrh.10hCLN2, an AAV capsid mutant or AAV hybrid serotype, an organ-tropic AAV, optionally, cardiac or skeletal muscle-tropic, wherein optionally the AAV is engineered to increase efficiency in targeting a specific cell type that is non-permissive to a wild type (wt) AAV and/or to improve efficacy in infecting only a cell type of interest, and optionally the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid;

the method comprises administering the peptide modulator of myosin subfragment-2 coiled coil stability-encoding nucleic acid, gene, transcript or message operatively linked to a transcriptional regulatory sequence, or the expression vehicle, vector, recombinant virus, or equivalent, to an individual or a patient in need thereof results in a peptide modulator of myosin subfragment-2 coiled coil stability being released into the bloodstream or general circulation, or an increased or sustained expression of the peptide modulator of myosin subfragment-2 coiled coil stability protein in the cell;

the peptide modulator of myosin subfragment-2 coiled coil stability-encoding nucleic acid is operatively linked to the transcriptional regulatory sequence; or the expression vehicle, vector, recombinant virus, or equivalent, is administered or delivered to the individual or a patient in need thereof, by oral, intramuscular (IM) injection, by intravenous (IV) injection, by subcutaneous (SC) or intradermal injection, by intrathecal injection, by intra-arterial (IA) injection, by intra-coronary injection, by inhalation, by aerosol, or by a biolistic particle delivery system, or by using a "gene gun", air pistol or a HELIOS™ gene gun (Bio-Rad Laboratories, Hercules, CA);

the individual, patient or subject is administered a stimulus or signal that induces expression of the peptide modulator of myosin subfragment-2 coiled coil stability-expressing nucleic acid or gene, or induces or activates a promoter (e.g., operably linked to the peptide modulator of myosin subfragment-2 coiled coil stability-expressing nucleic acid or gene) that induces expression of the peptide modulator of myosin subfragment-2 coiled coil stability-expressing nucleic acid or gene;

the individual, patient or subject is administered a stimulus or signal that induces synthesis of an activator of a promoter, optionally a cardiac cell-specific promoter (e.g., operably linked to the peptide modulator of myosin subfragment-2 coiled coil stability-expressing nucleic acid or gene);

the individual, patient or subject is administered a stimulus or signal that induces synthesis of a natural or a synthetic activator of the peptide modulator of myosin subfragment-2 coiled coil stability-expressing nucleic acid or gene or the peptide modulator of myosin subfragment-2 coiled coil stability-expressing nucleic acid or gene-specific promoter, wherein optionally the natural activator is an endogenous transcription factor;

the synthetic activator is a zinc-finger DNA binding protein designed to specifically and selectively turn on an endogenous or exogenous target gene, wherein optionally the endogenous target is a gene peptide modulator of myosin subfragment-2 coiled coil stability expressing nucleic acid or gene or an activator of a peptide modulator of myosin subfragment-2 coiled coil stability expressing nucleic acid or gene, or an activator of a promoter operatively linked to a peptide modulator of myosin subfragment-2 coiled coil stability-expressing nucleic acid or gene;

the stimulus or signal comprises a biologic, a light, a chemical or a pharmaceutical stimulus or signal;

the individual, patient or subject is administered a stimulus or signal that stimulates or induces expression of a post-transcriptional activator of a peptide modulator of myosin subfragment-2 coiled coil stability-expressing nucleic acid or gene, or an activator of a promoter operatively linked to a peptide modulator of myosin subfragment-2 coiled coil stability-expressing nucleic acid or gene;

the individual, patient or subject is administered a stimulus or signal that inhibits or induces inhibition of a transcriptional repressor or a post-transcriptional repressor of a peptide modulator of myosin subfragment-2 coiled coil stability expressing nucleic acid or gene;

the chemical or pharmaceutical that induces expression of the peptide modulator of myosin subfragment-2 coiled coil stability-expressing nucleic acid or gene, or induces expression of the regulated or inducible promoter operatively linked to the peptide modulator of myosin subfragment-2 coiled coil stability-expressing nucleic acid or gene, is an oral antibiotic, a doxycycline or a rapamycin; or a tet-regulation system using doxycycline is used to induce expression of the peptide modulator of myosin subfragment-2 coiled coil stability-expressing nucleic acid or gene, or an equivalent thereof;

the peptide modulator of myosin subfragment-2 coiled coil stability, or the peptide modulator of myosin subfragment-2 coiled coil stability-expressing nucleic acid or gene, or the expression vehicle, vector, recombinant virus, or equivalent, is formulated in a liquid, a gel, a hydrogel, a powder or an aqueous or a saline formulation;

the peptide modulator of myosin subfragment-2 coiled coil stability, or the peptide modulator of myosin subfragment-2 coiled coil stability-expressing nucleic acid or gene, or the expression vehicle, vector, recombinant virus, or equivalent, is formulated in a vesicle, liposome, nanoparticle or nanolipid particle (NLP);

the peptide modulator of myosin subfragment-2 coiled coil stability-expressing nucleic acid or gene or the expression vehicle, vector, recombinant virus, or equivalent, is formulated in an isolated or cultured cell, and optionally the cell is a mammalian cell, a cardiac cell, or a human cell, a non-human primate cell, a monkey cell, a mouse cell, a rat cell, a guinea pig cell, a rabbit cell, a hamster cell, a goat cell, a bovine cell, an equine cell, an ovine cell, a canine cell or a feline cell;

the peptide modulator of myosin subfragment-2 coiled coil stability, or the peptide modulator of myosin subfragment-2 coiled coil stability-expressing nucleic acid or gene, or the expression vehicle, vector, recombinant virus, or equivalent, is formulated as a pharmaceutical or sterile formulation; and/or the peptide modulator of myosin subfragment-2 coiled coil stability, or the peptide modulator of myosin subfragment-2 coiled coil stability-expressing nucleic acid or gene, or the expression vehicle, vector, recombinant virus, or equivalent, is formulated or delivered with, on, or in conjunction with a product of manufacture, an artificial organ or an implant.

In alternative embodiments, provided are uses of a synthetic or recombinant peptide, a synthetic or recombinant nucleic acid, an expression vehicle, an isolated or recombinant cell or a product of manufacture, as provided herein, for:

treating, ameliorating or protecting (preventing), slowing the progress of, abating or decreasing one or more symptoms of, or reversing; hypertrophic cardiomyopathy (HCM), dilated cardiomyopathy (DCM), and chronic congestive heart failure (CHF)

increasing exercise tolerance in a subject with heart failure;

reducing hospitalization in a subject with heart failure;

improving quality of life in a subject with heart failure;

decreasing morbidity in a subject with heart failure;

decreasing mortality in a subject with heart failure;

modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies, in an individual or a patient in need thereof.

In alternative embodiments, provided are synthetic or recombinant peptides, synthetic or recombinant nucleic acids, expression vehicles, isolated or recombinant cells or products of manufacture, as provided herein, for use in:

treating, ameliorating or protecting (preventing), slowing the progress of, abating or decreasing one or more symptoms of, or reversing; hypertrophic cardiomyopathy (HCM), dilated cardiomyopathy (DCM), and chronic congestive heart failure (CHF)

increasing exercise tolerance in a subject with heart failure;

reducing hospitalization in a subject with heart failure;

improving quality of life in a subject with heart failure;

decreasing morbidity in a subject with heart failure;

decreasing mortality in a subject with heart failure;

modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies, in an individual or a patient in need thereof.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

FIG. 21A shows a GFS experimental slide prepared by first selecting a clean glass slide and making a four walled chamber with edges of coverslip and vacuum grease;

FIG. 21B shows one side of a chamber being the glass coverslip treated with G-actin or the interested muscle myosin S2 peptide;

FIG. 21C that within a chamber, around 50 μL of anticipated myosin S2 peptide or actin coated silica beads was added followed by 100 μL low salt buffer, and 5 μL anti-S2 peptide; and FIG. 21D shows a chamber as sealed with another clean coverslip and vacuum grease leaving the center of the chamber with suspension buffer, treated bead and molecule of interest untethered, as described in detail in Example 1, below.

FIG. 27A graphically illustrates lifetime of cardiac ΔE930 muscle myosin S2 donor probe treated with the stabilizer peptide (green) compared to control (red);

FIG. 27B graphically illustrates lifetime of cardiac ΔE930 muscle myosin S2 donor probe treated with the stabilizer peptide (green) compared to cardiac wild-type muscle myosin S2 donor probe treated with the stabilizer peptide (red), as described in detail in Example 1, below.

FIG. 29A graphically illustrates lifetime of smooth muscle myosin S2 donor probe; and FIG. 29B graphically illustrates lifetime of smooth muscle myosin S2 donor probe treated with the stabilizer (green) and the destabilizer (blue);

as described in detail in Example 1, below.

Figure 30:
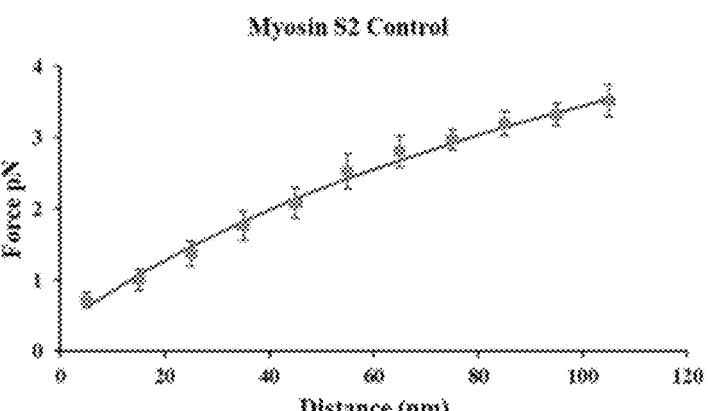

FIG. 30 graphically illustrates a force-distance graph of uncoiling a single molecule of cardiac myosin S2 peptide, as described in detail in Example 1, below.

Figure 31:
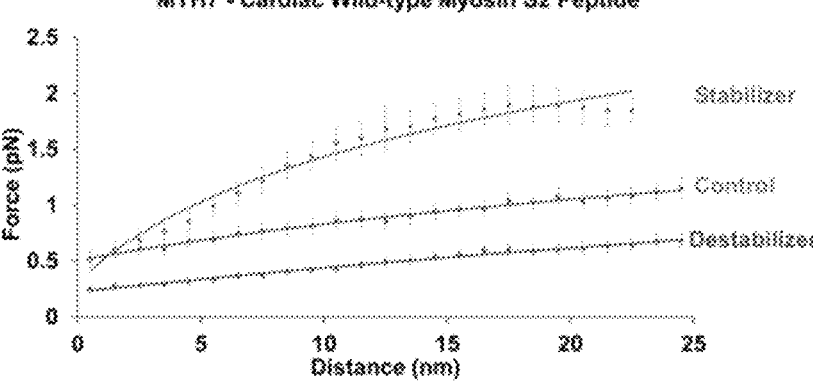

FIG. 31 illustrates a force-distance graph showing the force required to uncoil cardiac muscle myosin S2 molecule for a length of 10 nm in absence of anti-S2 peptides, as described in detail in Example 1, below.

Figure 32:
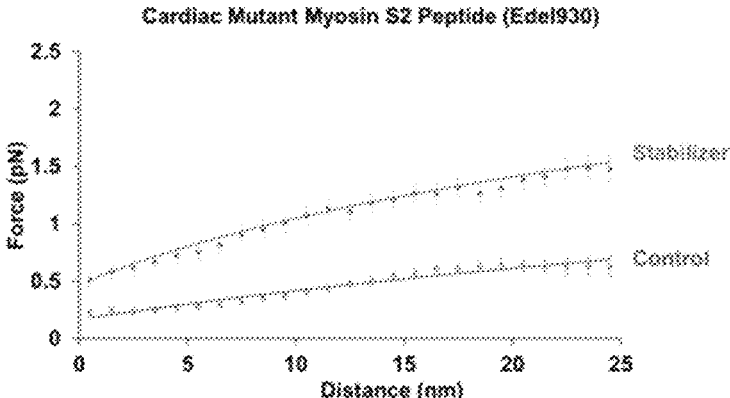

FIG. 32 illustrates a force-distance graph of uncoiling a single molecule of cardiac myosin S2 mutant peptide isoform, MYH7, in presence of anti-S2 peptide: (Green, or upper line) Force-distance graph of uncoiling a single molecule in presence of the stabilizer peptide; and (Blue, or lower line) Force-distance graph of uncoiling a single molecule, as described in detail in Example 1, below.

Figure 33:
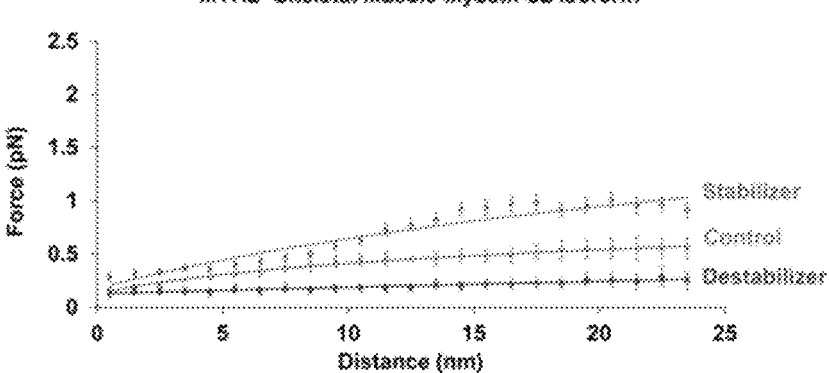

FIG. 33 illustrates a force-distance graph of uncoiling a single molecule of the skeletal myosin S2 peptide isoform (MYH2) in presence of anti-S2 peptides: (Green, or upper line) Force-distance graph of uncoiling a single molecule in presence of the stabilizer peptide; (Red, or lower line) Force-distance graph of uncoiling a single molecule in presence of the destabilizer peptide; and (Blue, or middle line) Force-distance graph of uncoiling a single molecule, as described in detail in Example 1, below.

Figure 34:
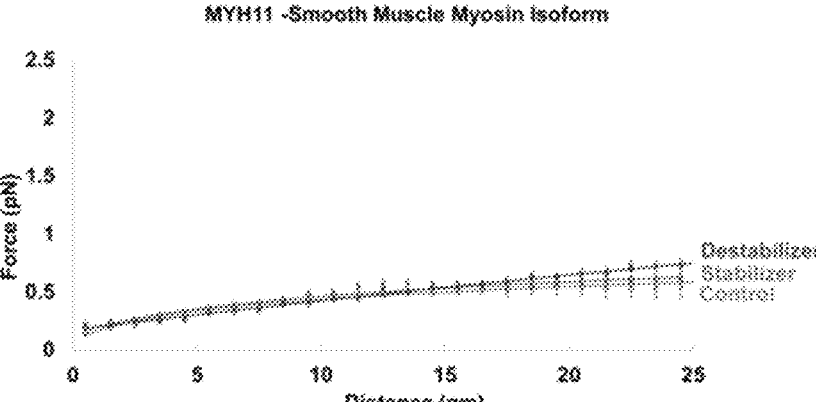

FIG. 34 illustrates a force-distance graph of uncoiling a single molecule of smooth myosin S2 peptide isoforms (MYH11) belonging to myosin heavy chain family in presence of anti-S2 peptides: (Green, or middle line); Force-distance graph of uncoiling a single molecule in presence of stabilizer peptide; (Red, or upper line) Force-distance graph of uncoiling a single molecule in presence of destabilizer peptide; and, (Blue, or lower line) Force-distance graph of uncoiling a single molecule, as described in detail in Example 1, below.

Figure 35:
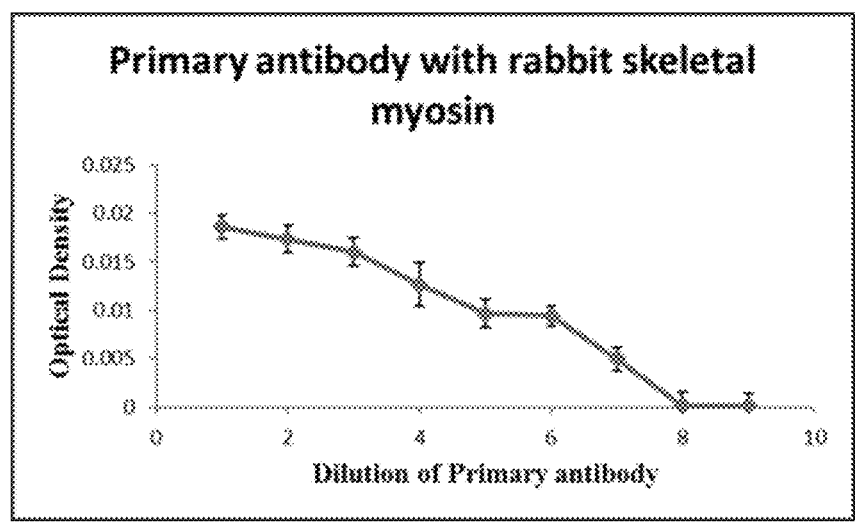

FIG. 35 graphically illustrates optical density versus dilutions of primary anti-S2 antibody, where mapped on x-axis is the exponential dilution for primary polyclonal anti-S2 antibody, as described in detail in Example 1, below.

Figure 36:
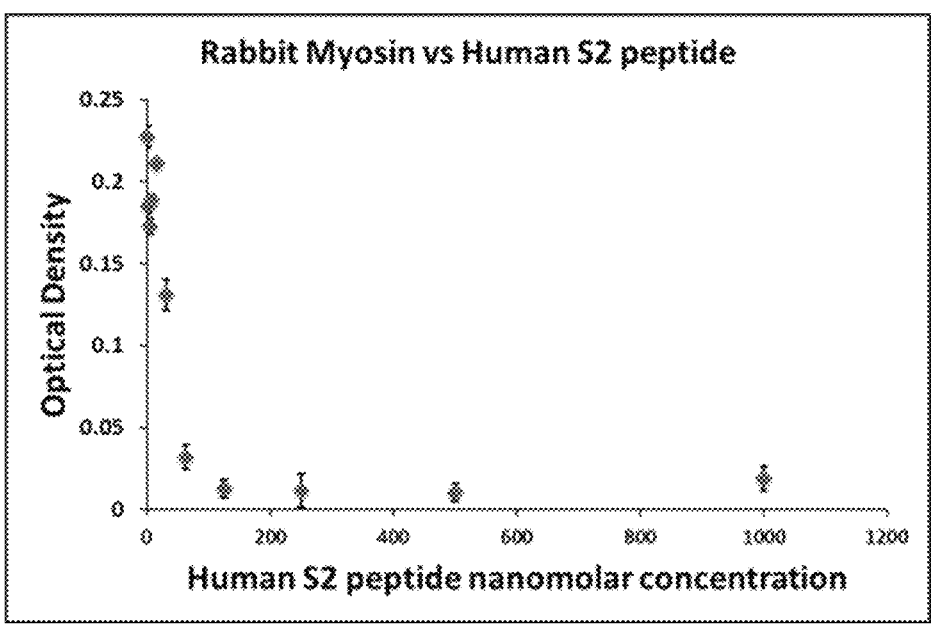

FIG. 36 graphically illustrates an exemplary cELISA for competitive binding of polyclonal anti-S2 antibody to human β-cardiac myosin S2 and rabbit skeletal myosin S2, as described in detail in Example 1, below.

Figure 37A:
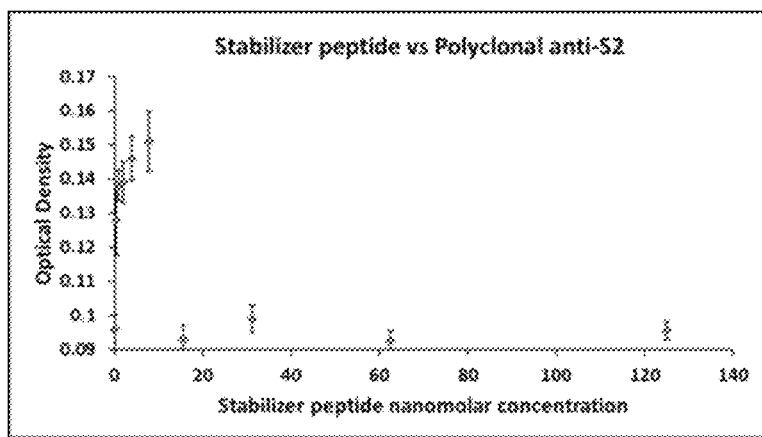
Figure 37B:
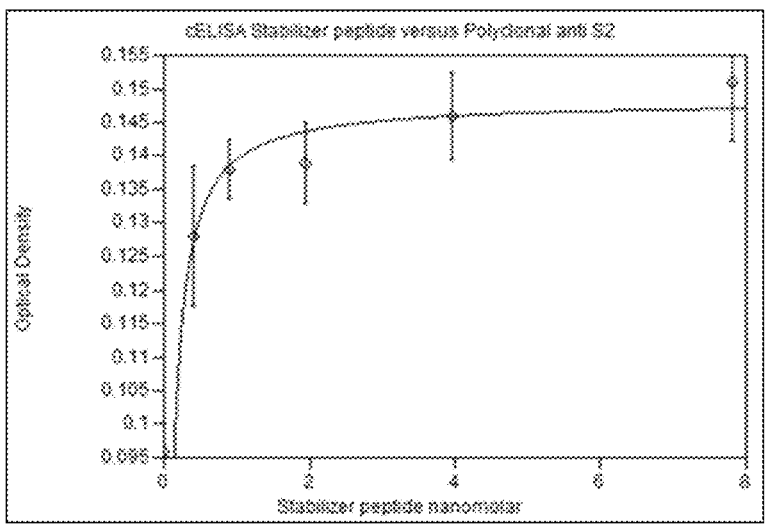

FIG. 37A graphically illustrates OD versus increasing amounts of stabilizer peptide concentration, where the low-high-low OD trend observed states the specific binding of stabilizer peptide to human cardiac myosin S2 peptide; and, FIG. 37B graphically illustrates a curve fit to determine the binding efficiency of stabilizer peptide to human cardiac myosin S2 peptide, as described in detail in Example 1, below.

Figure 38A:
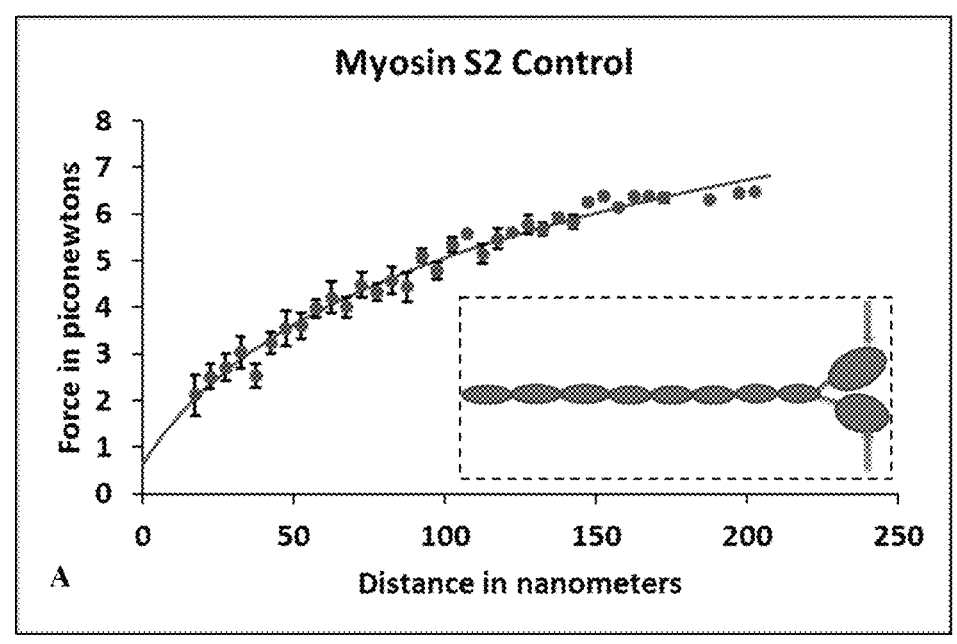
Figure 38B:
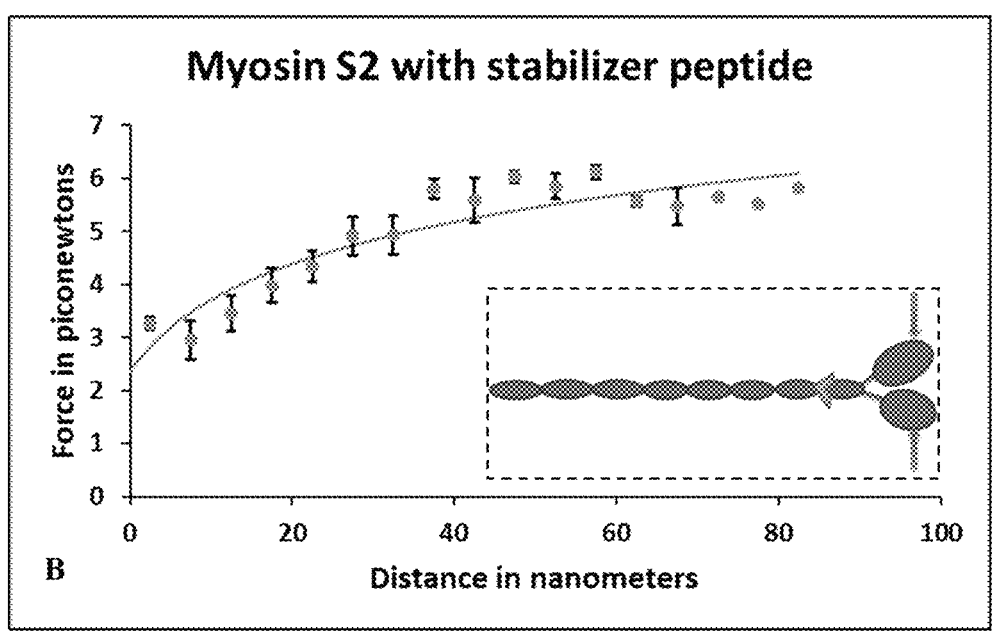

FIG. 38A-B illustrate a GFS curve fit for average forces to distance for the effect of stabilizer peptide over myosin S2 coiled coil:

FIG. 38A: Force distance curve for myosin molecule in absence of stabilizer peptide;

FIG. 38B: Force distance curve for myosin molecule in presence of stabilizer peptide, and in the dashed box; cartoon of a myosin molecule (red) with stabilizer peptide (green) tethered at myosin S1 actin with actin (cyan arrow) for GFS, as described in detail in Example 1, below.

Figure 39:
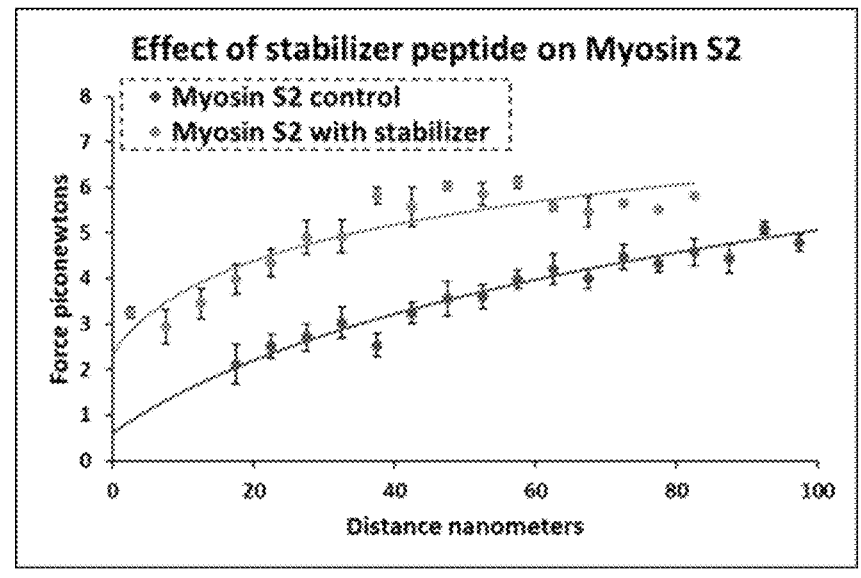

FIG. 39 illustrates a comparison of force distance curve of myosin molecule without stabilizer peptide (blue) and myosin molecule with stabilizer peptide added (red), as described in detail in Example 1, below.

Figure 40A:
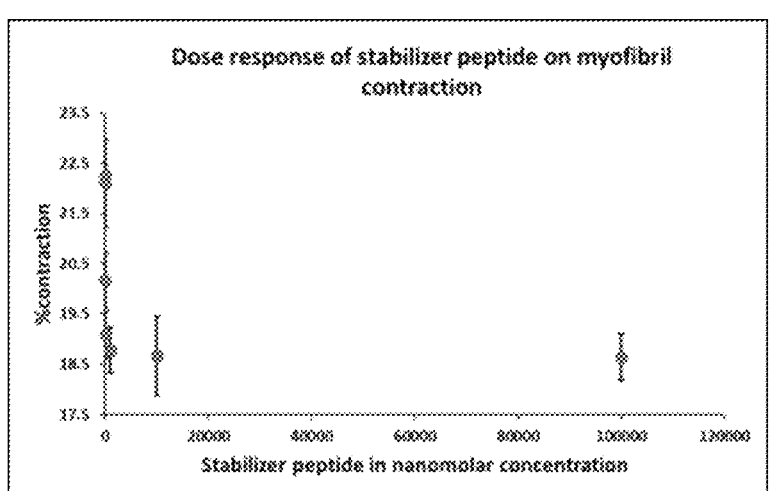
Figure 40B:
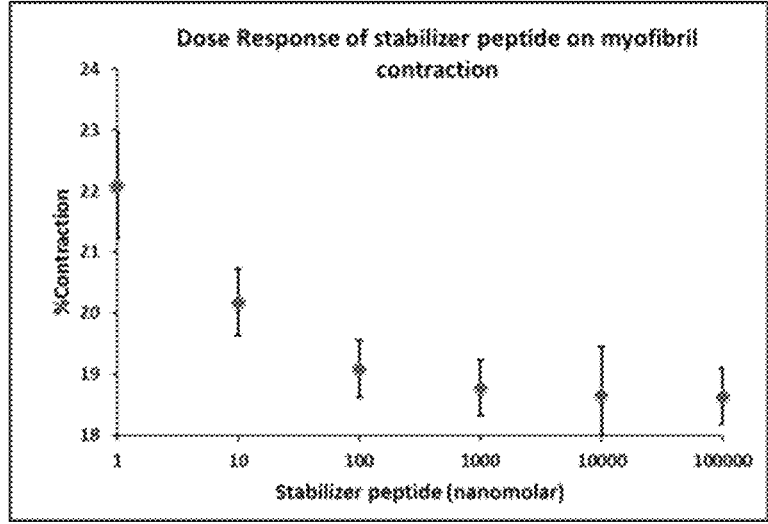

FIG. 40A-B graphically illustrate dose response of stabilizer peptide on myofibril contraction:

FIG. 40A graphically illustrates percentage of contraction versus stabilizer in nanomolar concentration;

FIG. 40B graphically illustrates percentage of contraction versus stabilizer in nanomolar concentration in the logarithmic power of 10, as described in detail in Example 1, below.

Figure 41A:
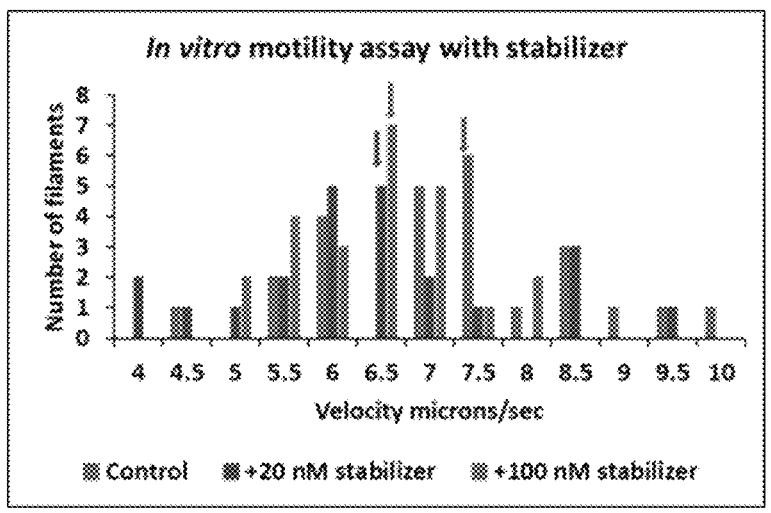
Figure 41B:
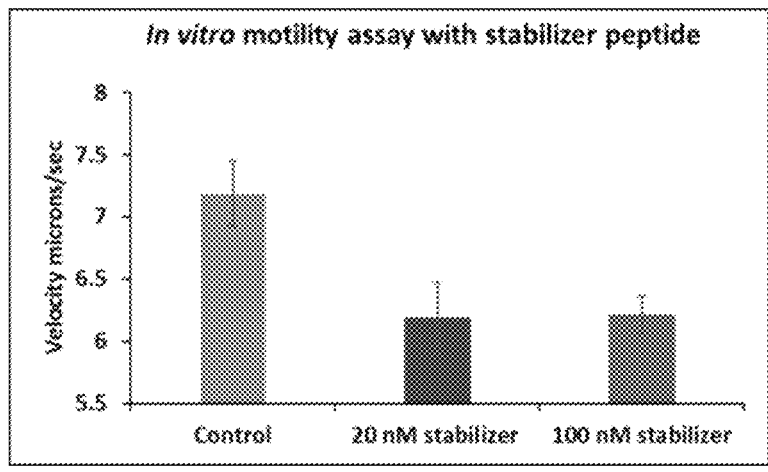

FIG. 41A-B illustrate histograms for the velocity of actin thin filaments in presence of stabilizer peptide:

FIG. 41A graphically illustrates histogram for the number of actin thin filaments with their respective velocity, control (blue); velocity of actin in absence of stabilizer peptide, test (red); velocity of actin thin filaments in presence of 20 nM stabilizer peptide and test (green); velocity of actin thin filaments in presence of 100 nM stabilizer peptide; and FIG. 41B graphically illustrates a histogram for the average velocities of actin thin filaments in control (blue) (n=26), test with 20 nM stabilizer peptide (red) (n=23) and test with 100 nM stabilizer peptide (green), as described in detail in Example 1, below.

Figure 42A:
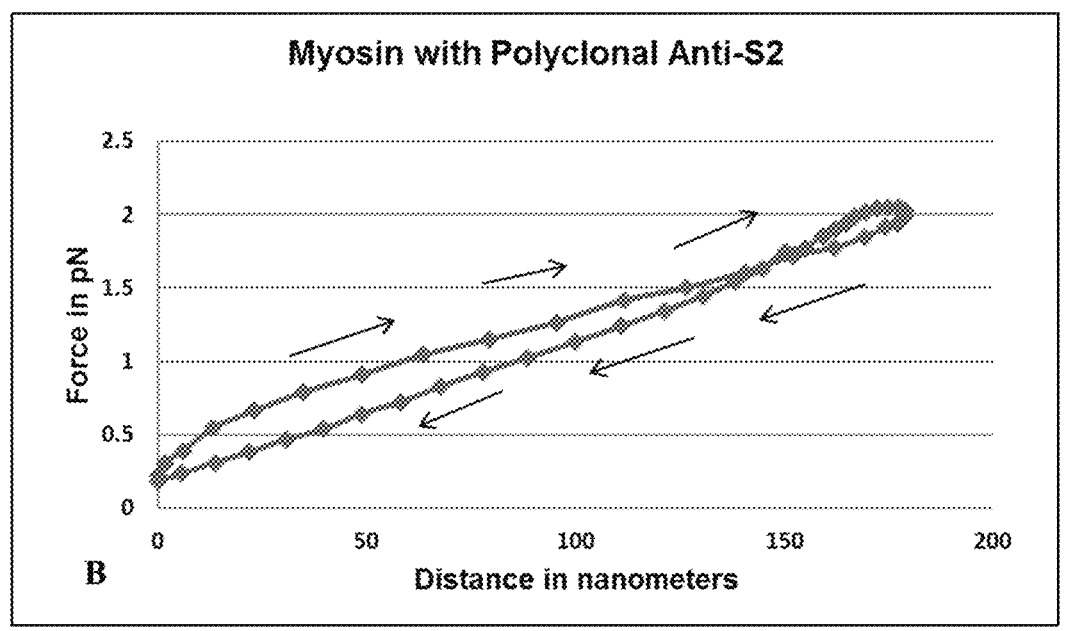
Figure 42B:
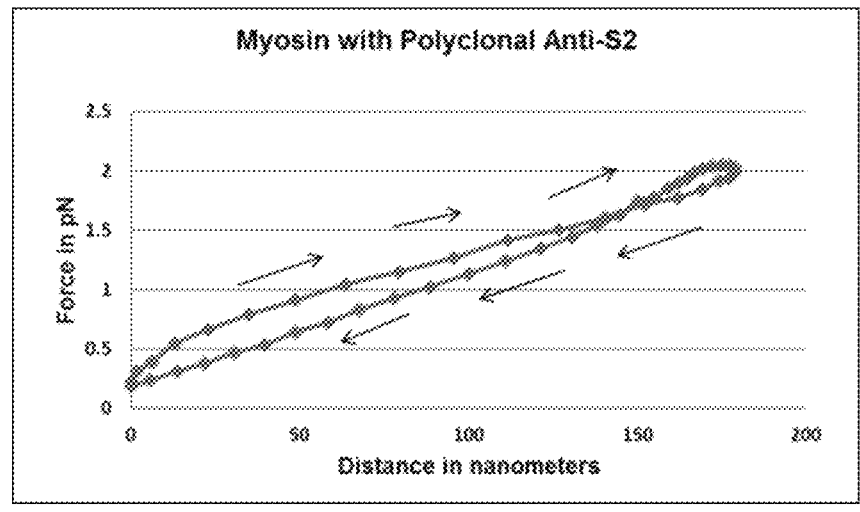

FIG. 42A-B illustrate force distance traces for myosin treated with polyclonal anti-S2 antibody:

FIG. 42A graphically illustrate force distance curve for myosin molecule without polyclonal anti-S2 antibody; and FIG. 42B graphically illustrate force distance curve for myosin molecule with polyclonal anti-S2 antibody; (black) arrows indicate the event of uncoiling and coiling back of myosin coiled coil, as described in detail in Example 1, below.

Figure 43:
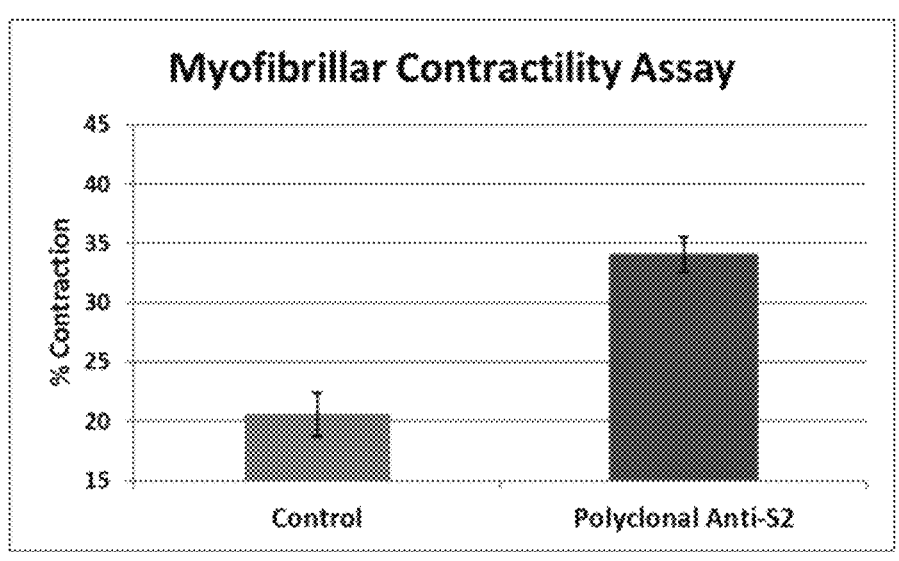

FIG. 43 graphically illustrates percentage contraction in myofibrils without (blue, control) and with polyclonal anti-S2 antibody (red, right), as described in detail in Example 1, below.

Figure 44A:
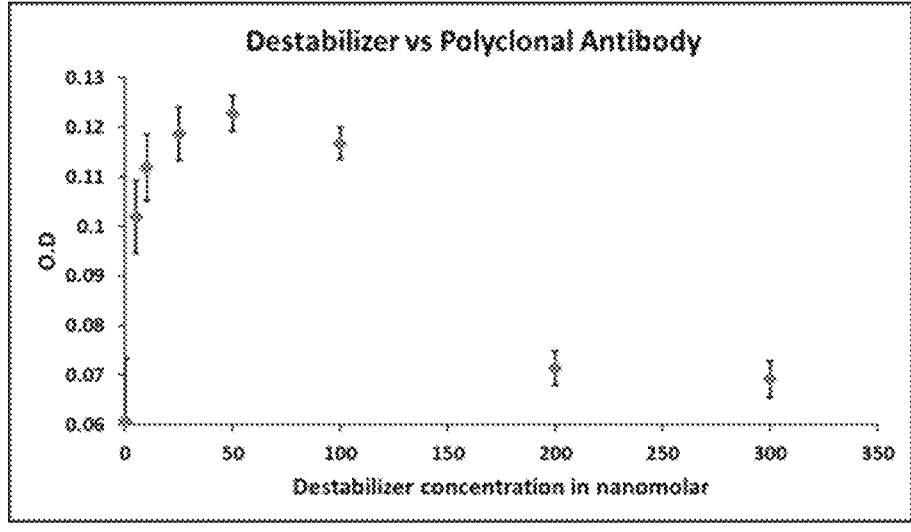
Figure 44B:
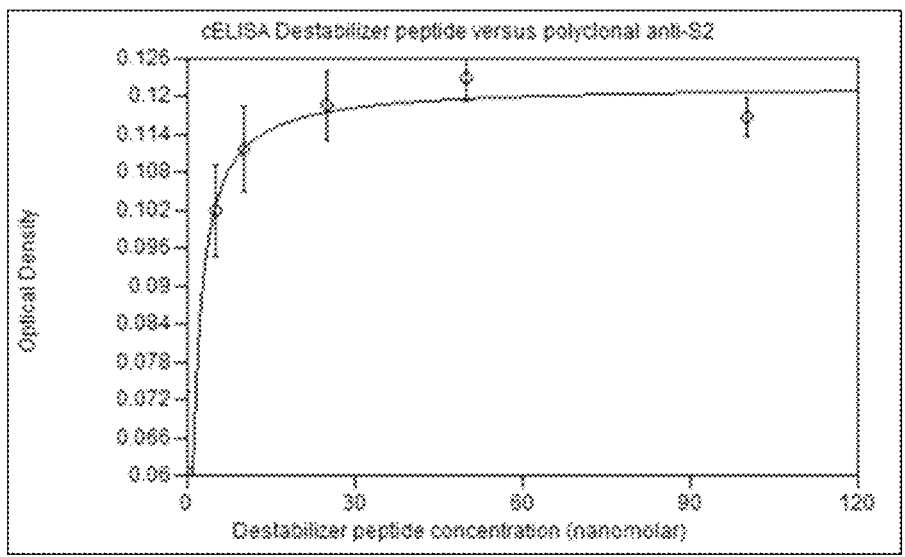

FIG. 44A-B graphically illustrates optical Density versus the destabilizer peptide concentration:

FIG. 44A graphically illustrate OD with increasing concentration of stabilizer peptide gave the trend of low-high-low OD;

FIG. 44B graphically illustrates curve fit of OD with increasing destabilizer concentration to calculate the binding efficiency $(K_d)$, as described in detail in Example 1, below.

Figure 45A:
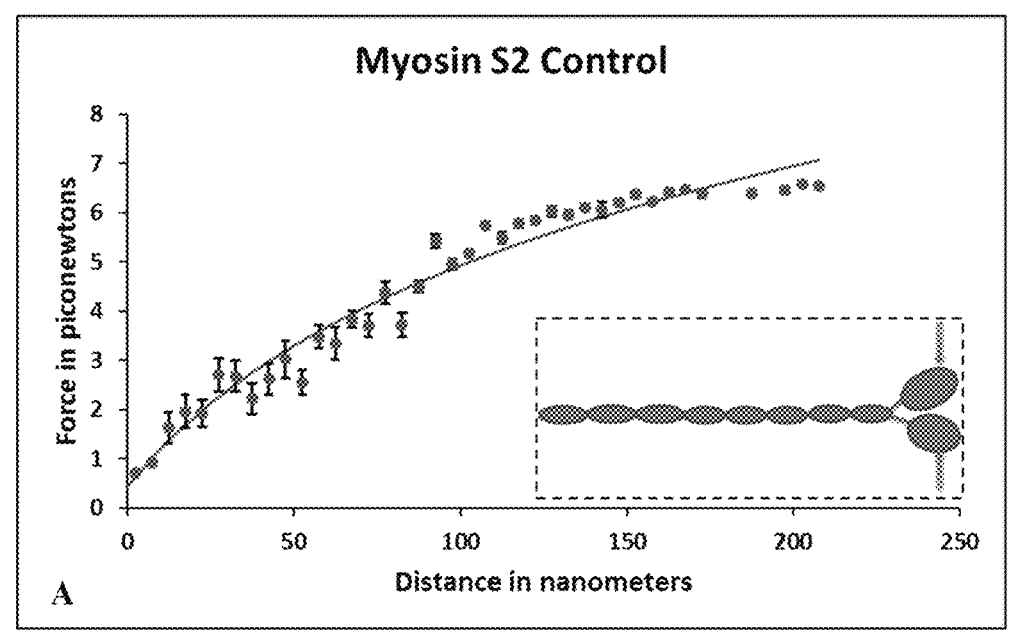
Figure 45B:
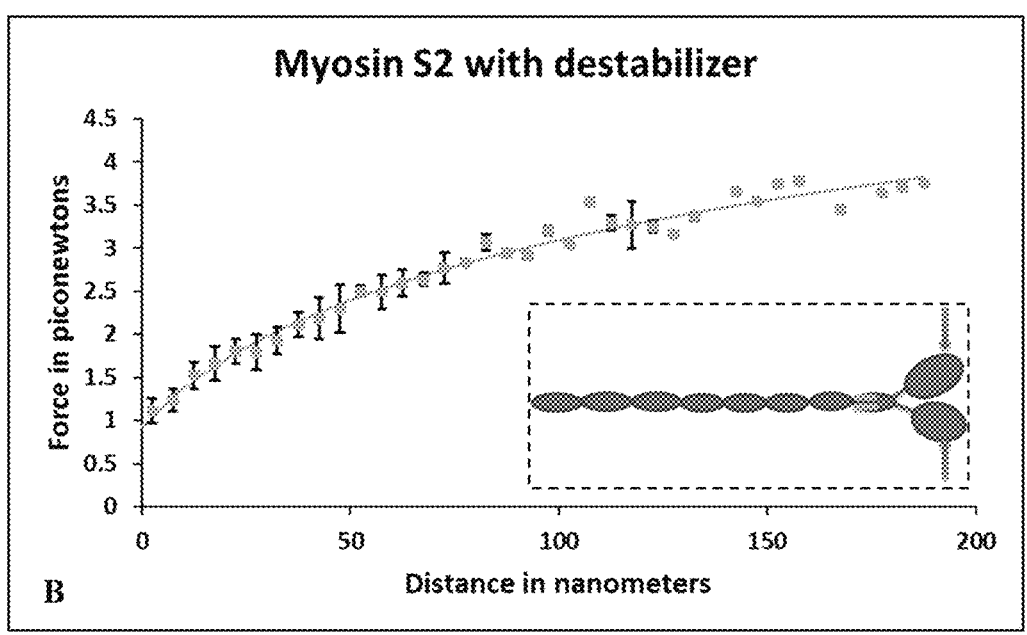

FIG. 45A-B illustrate force distance curve for GFS experiment with rabbit skeletal myosin treated with destabilizer peptide:

FIG. 45A graphically illustrates force distance curve for uncoiling of myosin molecule with no destabilizer peptide added; and FIG. 45B graphically illustrates force distance curve for uncoiling of myosin molecule with destabilizer peptide added; in dashed box; cartoon of a myosin molecule (red) with destabilizer peptide (orange) tethered at myosin S1 region with actin (cyan arrow) for GFS, as described in detail in Example 1, below.

Figure 46:
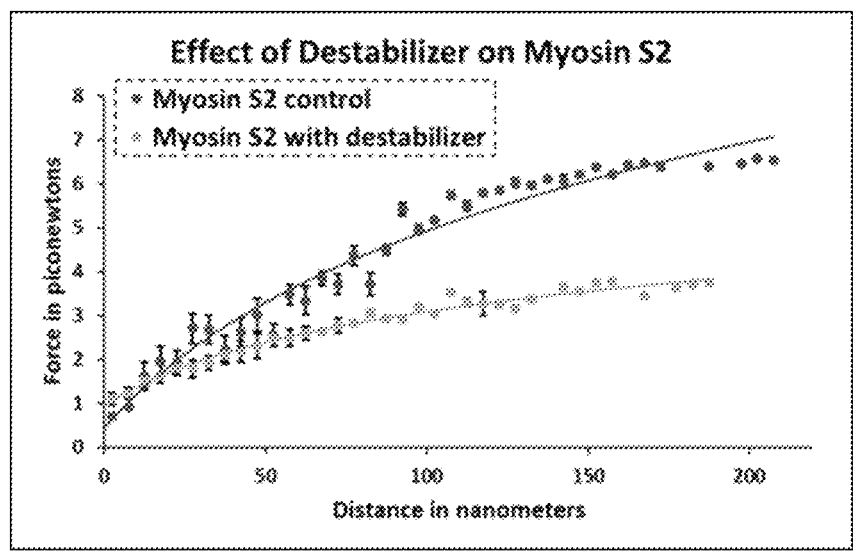

FIG. 46 graphically illustrates comparison of force distance curve for control (blue) and test (red) assay for myosin molecule treated with destabilizer peptide, as described in detail in Example 1, below.

Figure 47:
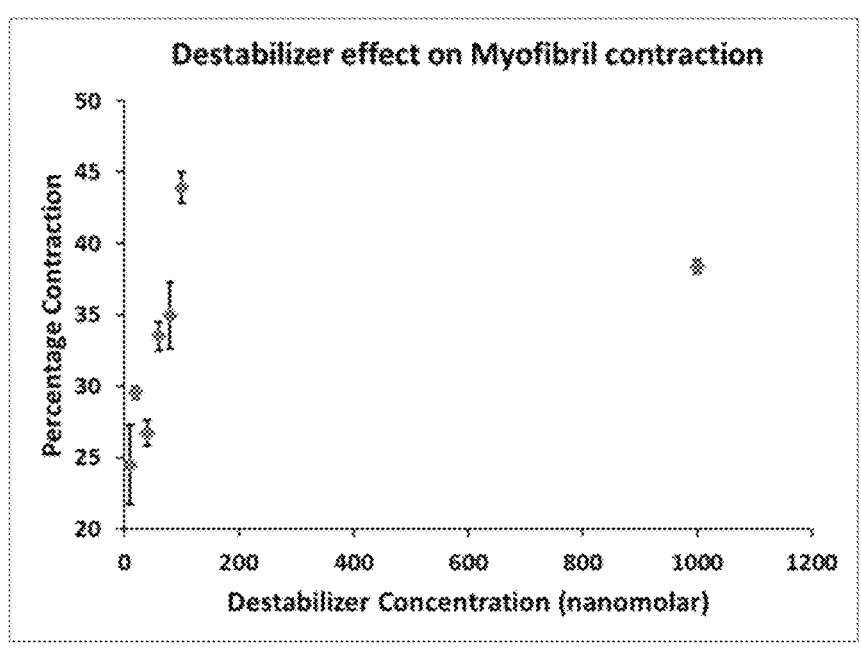

FIG. 47 graphically illustrates percentage contraction in sarcomeres versus destabilizer peptide concentration., as described in detail in Example 1, below.

Figure 48A:
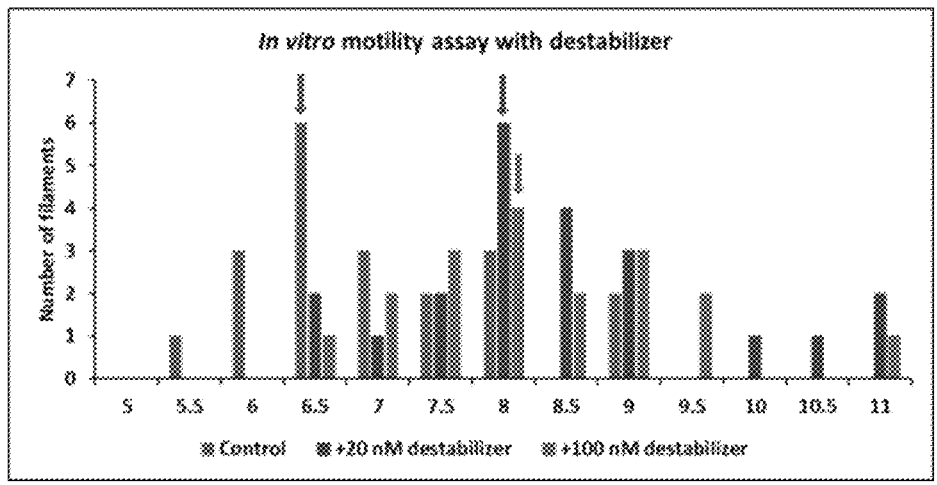
Figure 48B:
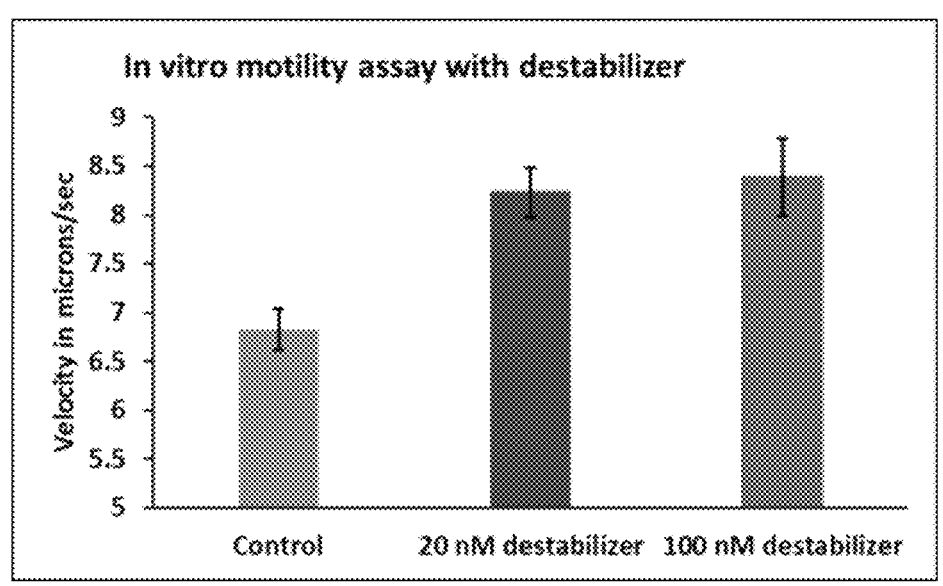

FIG. 48A-B illustrate histograms for the velocity of actin thin filaments in presence of destabilizer peptide:

FIG. 48A graphically illustrates a histogram for the number of actin thin filaments with their respective velocity, control (blue); velocity of actin in absence of destabilizer peptide, test (red); velocity of actin thin filaments in presence of 20 nM destabilizer peptide and test (green); velocity of actin thin filaments in presence of 100 nM destabilizer peptide; and FIG. 48B graphically illustrates a histogram for the average velocities of actin thin filaments in control (blue, or left column), test with 20 nM destabilizer peptide (red, or middle) and test with 100 nM destabilizer peptide (green or right column), as described in detail in Example 1, below.

Figure 49:
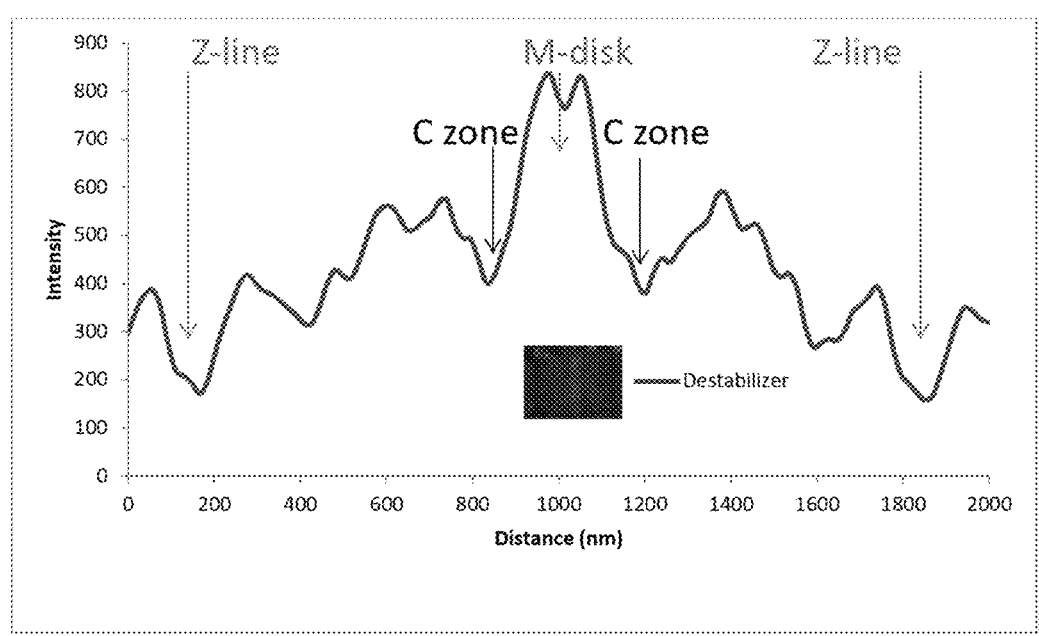

FIG. 49 illustrates a fluorescent intensity profile from a super-resolution microscopy of a single sarcomere stained with a fluorescein labeled destabilizer peptide using expansion microscopy and a confocal microscope with a water immersion objective lens, as described in detail in Example 1, below.

Figure 50A:
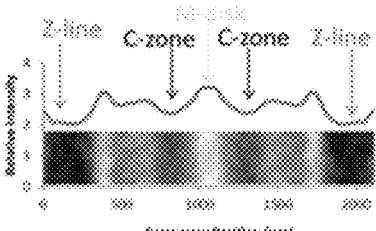
Figure 50B:
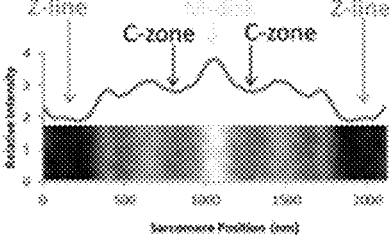

FIG. 50A-B illustrate images of a super-resolution microscopy averaged images of sarcomeres stained with both Stabilizer (FIG. 50A) and an exemplary destabilizer (FIG. 50B) illustrating specific labeling of the A band, as described in detail in Example 1, below.

Figure 51:
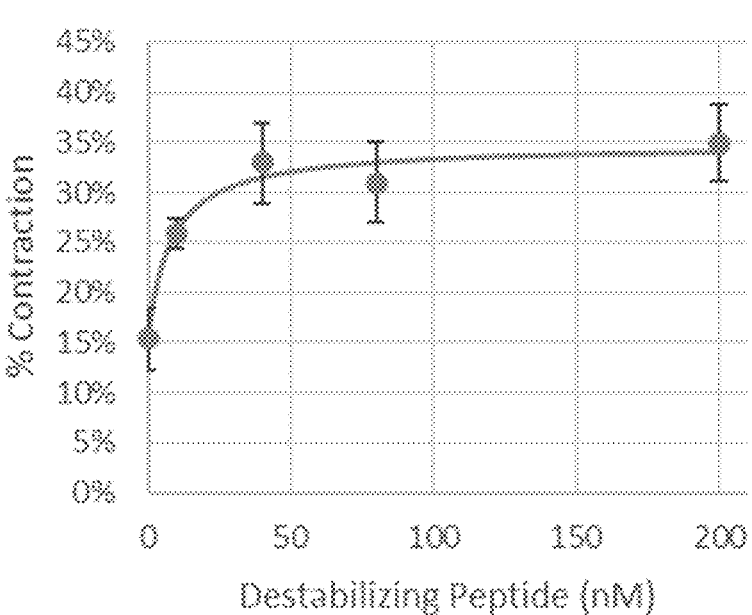

FIG. 51 graphically illustrates rabbit myofibrillar contractility assay with destabilizing peptide, as described in detail in Example 1, below.

Figure 52:
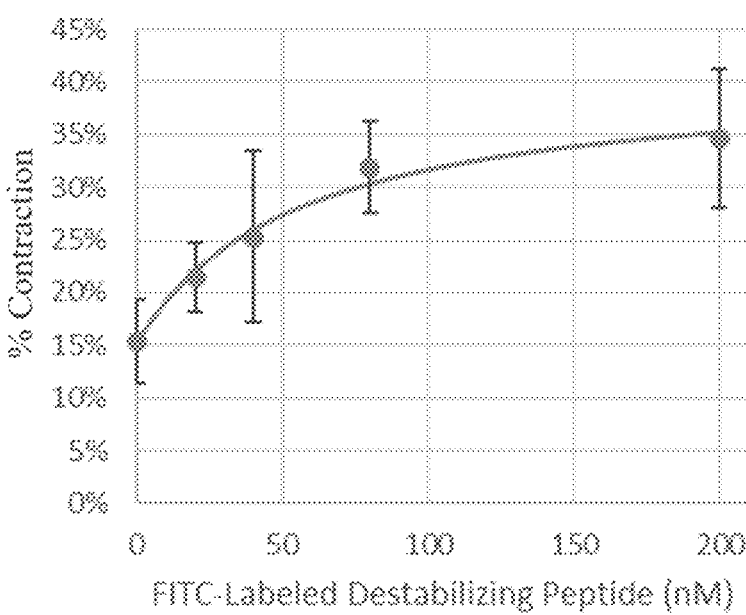

FIG. 52 graphically illustrates rabbit myofibrillar contractility assay with FITC labeled destabilizing peptide, as described in detail in Example 1, below.

Figure 53:
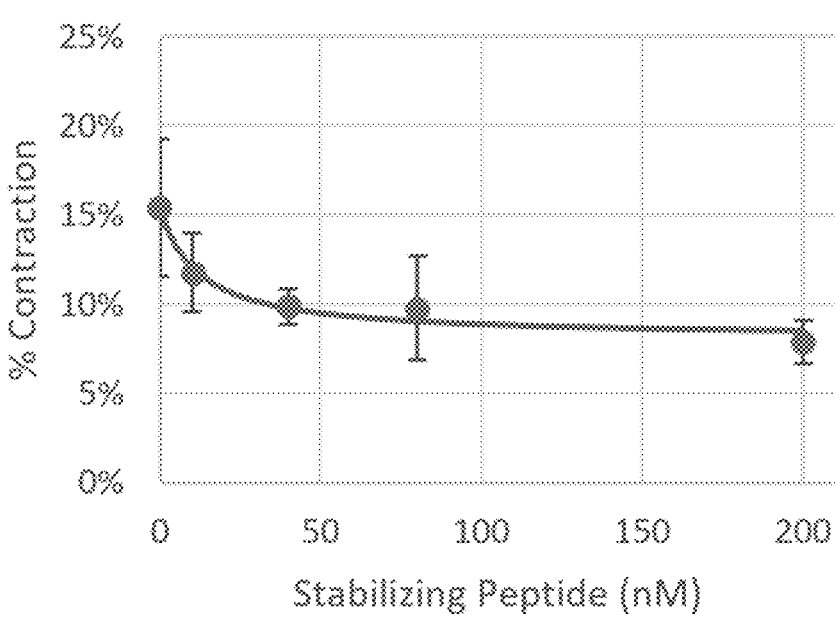

FIG. 53 graphically illustrates rabbit myofibrillar contractility assay with stabilizing peptide, as described in detail in Example 1, below.

Figure 54:
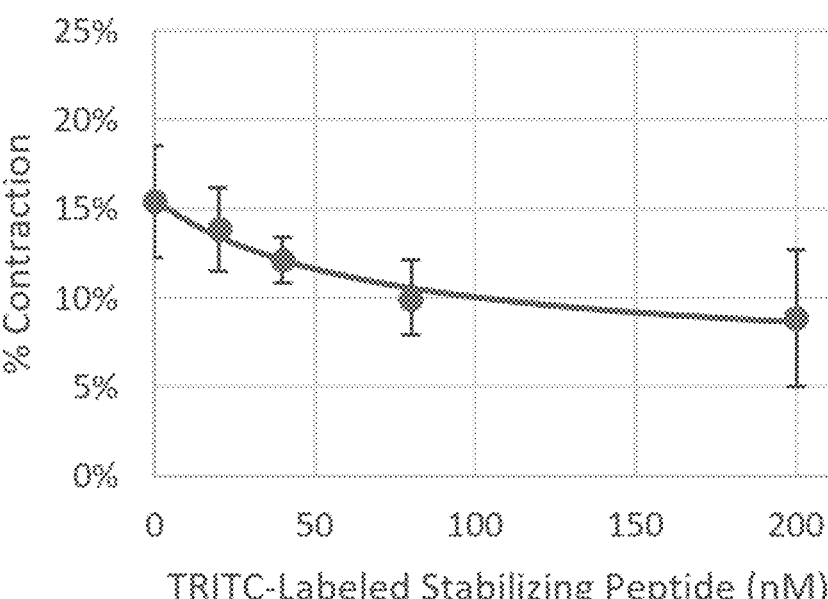

FIG. 54 graphically illustrates rabbit myofibrillar contractility assay with TRITC labeled stabilizing peptide, as described in detail in Example 1, below.

FIG. 55A illustrates an image of labeled destabilizer before ATP 40 nM, FIG. 55B illustrates an image of labeled Destabilizer after ATP 40 nM, % Contraction: 25%; FIG. 55C illustrates an image of labeled Stabilizer before ATP 40 nM, FIG. 55D illustrates an image of labeled Stabilizer after ATP 40 nM, % Contraction: 13%, as described in detail in Example 1, below.

FIG. 56A illustrates an image of unlabeled destabilizer before ATP 40 nM, FIG. 56B illustrates an image of unlabeled Destabilizer after ATP 40 nM, % Contraction: 30%; FIG. 56C illustrates an image of unlabeled stabilizer before ATP 40 nM, 56D illustrates an image of unlabeled Stabilizer after ATP 40 nM, % Contraction: 11%, as described in detail in Example 1, below.

Figure 57:
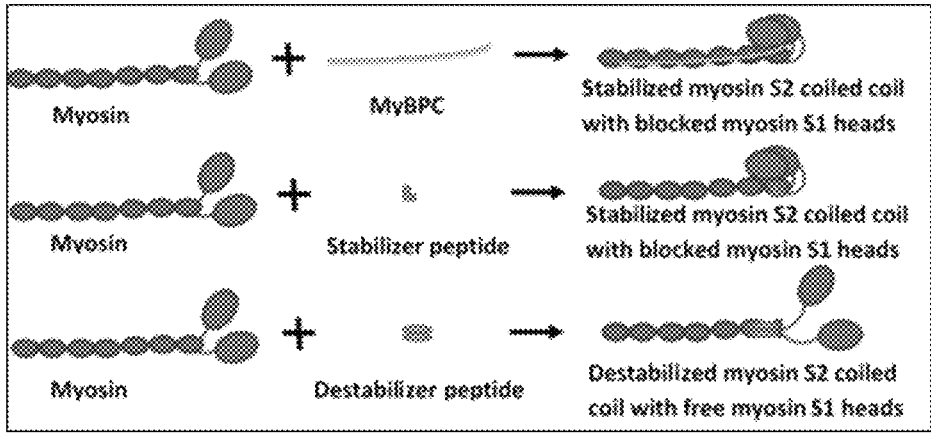

FIG. 57 schematically illustrates the effect of myosin S2 binding proteins on myosin S2 coiled coil, as described in detail in Example 1, below.

Figure 58:
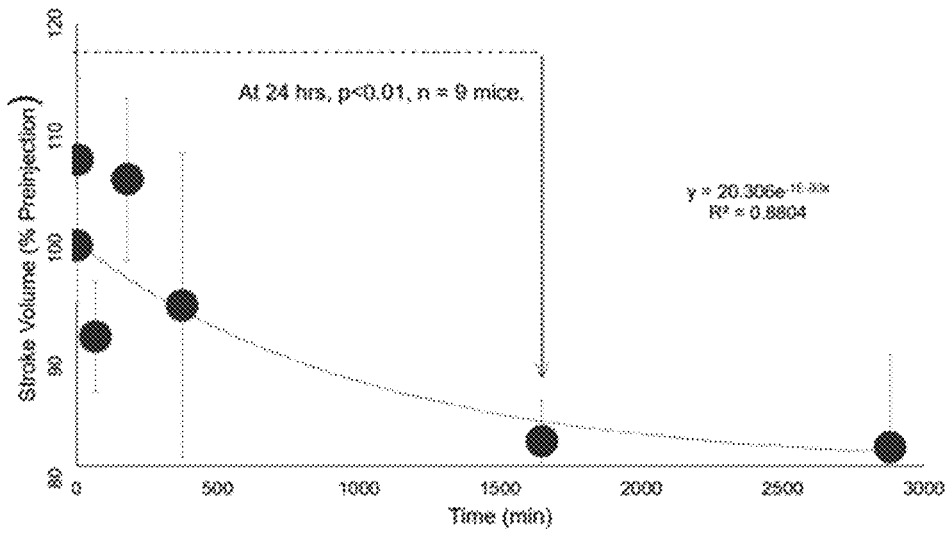

FIG. 58 graphically illustrates the kinetics of stroke volume response to TANNylated Stabilizer peptide injection in a mouse, as described in detail in Example 2, below.

Figure 59:
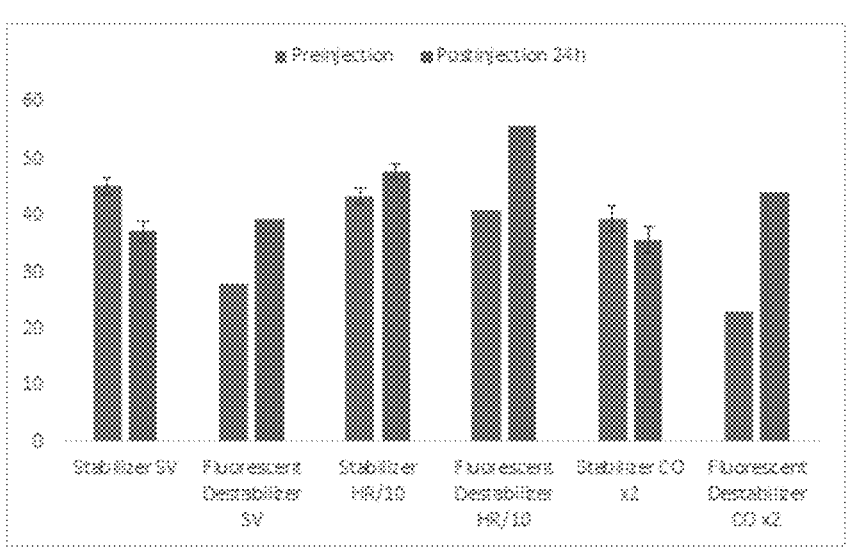

FIG. 59 graphically illustrates the response of the TANNylated fluorescent Destabilizer peptide compared to that of the TANNylated Stabilizer peptide at 24 hours post-injection, as described in detail in Example 2, below.

Figure 60:
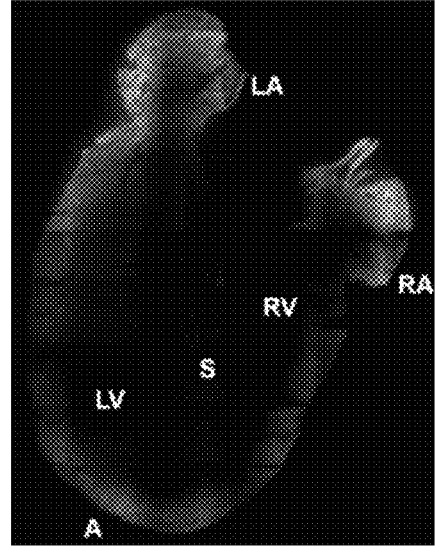

FIG. 60 illustrates an image of a central cryostat section of heart from mouse 24 hours post-injection of the TANNylated fluorescent peptide and imaged by epifluorescence microscopy, as described in detail in Example 2, below.

Figure 61:
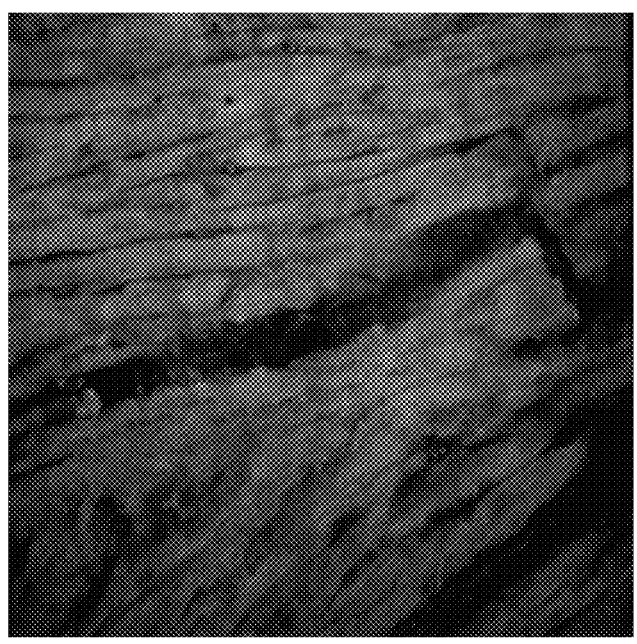

FIG. 61 illustrates an image of: confocal two color image of mouse heart cryostat section; green is the fluorescent peptide; blue is the DAPI counterstain for the nuclei, as described in detail in Example 2, below.

Figure 62:

FIG. 62 illustrates an image of: a confocal image of mouse heart cryostat section in the fluorescein channel, where striations indicating sarcomeric labeling are occasionally resolved, as described in detail in Example 2, below.

Figure 63:
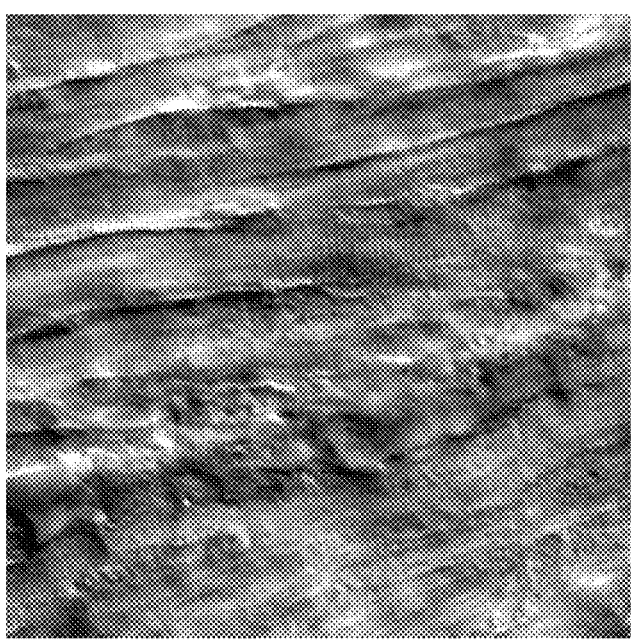

FIG. 63 illustrates an image of: corresponding differential interference contrast image to FIG. 62, as described in detail in Example 2, below.

Figure 64:
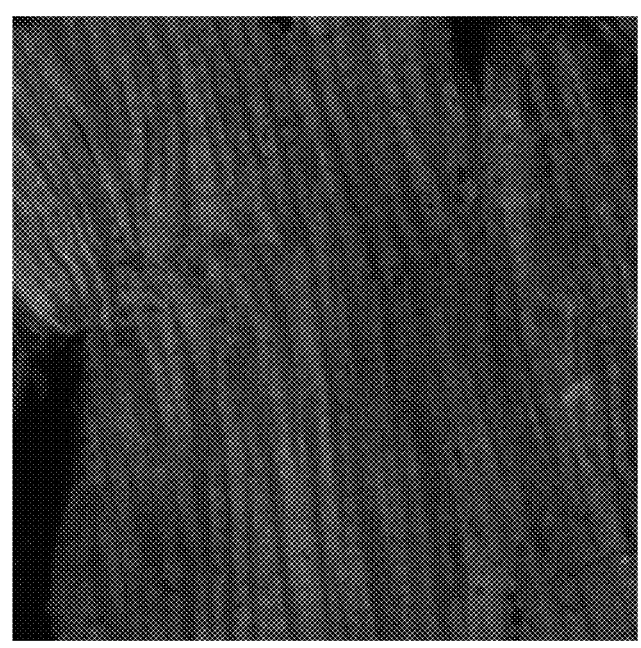

FIG. 64 illustrates an image of: a super-resolution ZEISS AIRYSCAN™ confocal image of mouse heart cryostat section, as described in detail in Example 2, below.

Figure 65:
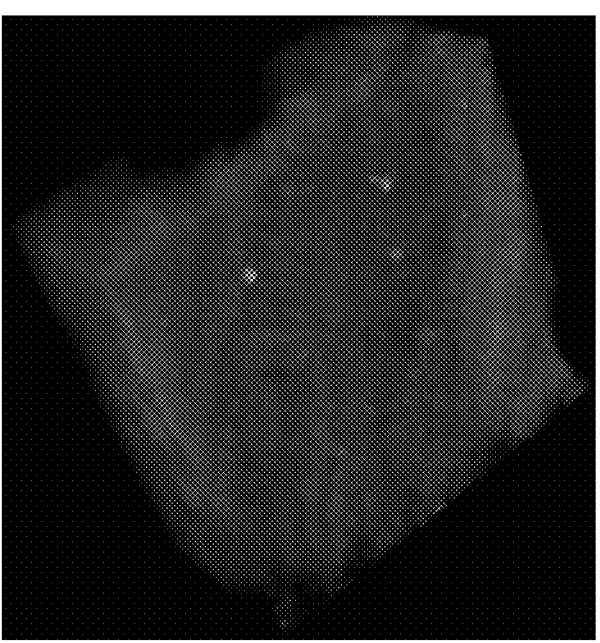

FIG. 65 illustrates an image of: a super-resolution ZEISS AIRYSCAN™ confocal 3D projection of a mouse heart cryostat section, as described in detail in Example 2, below.

Figure 66:
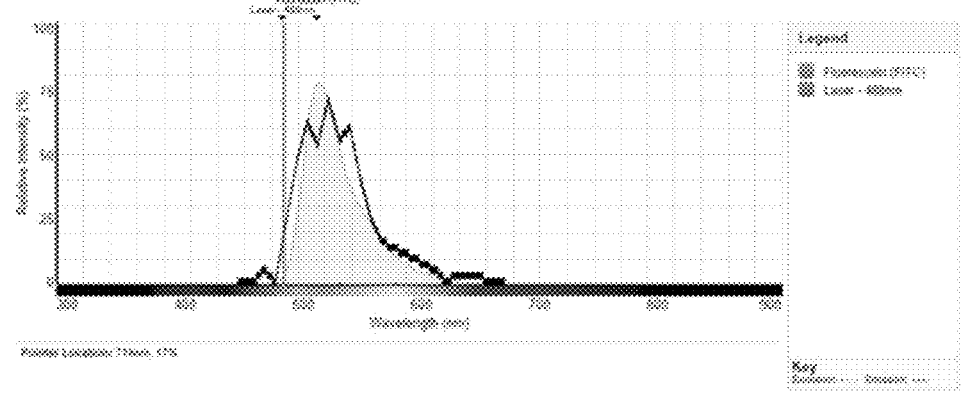

FIG. 66 graphically illustrates hyperspectral imaging emission spectrum confocal image of mouse heart cryostat section (black) compared to stock fluorescein emission spectrum (green), as described in detail in Example 2, below.

Like reference symbols in the various drawings indicate like elements.

DETAILED DESCRIPTION

In alternative embodiments, provided are compositions, including products of manufacture and kits, and methods, for treating, ameliorating or preventing a muscle disease, obesity and/or a heart disease, the method comprising: first identifying an individual (e.g., a patient) exhibiting one or more symptoms or manifestations of a heart or muscle disease, or obesity; followed by administering to the individual a modulator of myosin coiled coil stability. In alternative embodiments, the modulator is a peptide derived from a coiled coil trigger sequence for myosin (e.g., human myocin) subfragment-2, or the peptide is a de novo peptide sequence designed to interact, i.e., bind to, e.g., specifically bind to or with, a myosin subfragment-2 polypeptide sequence; and alternative embodiments the peptide sequence is no more than about 50 residues in length.

Provided herein are peptides that have been designed to modulate the stability of the coiled coil structure of myosin subfragment-2. The intent of these peptides is to regulate muscle contraction by influencing the ability of myosin to interact with actin. A peptide as provided herein that can reduce the contraction of cardiac muscle (a myosin subfragment-2 stabilizing peptide has the effect of decreasing muscle contraction) promises applications in treating the effects of hypertrophic cardiomyopathy (HCM). On the other hand, the effects of dilated cardiomyopathy (DCM), and chronic congestive heart failure (CHF) are alleviated by a peptide as provided herein that works to enhance muscle contraction (a myosin subfragment-2 destabilizing peptide has the effect of increasing muscle contraction).

In alternative embodiments, the destabilizing peptide that binds to the myosin subfragment-2 polypeptide comprises, consists essentially of or consists of: EMNERLEDEREM-KAELTAK (SEQ ID NO:1), with L or D amino acid isomers; or In alternative embodiments, the stabilizing peptide that binds to the myosin subfragment-2 polypeptide comprises, consists essentially of or consists of amino acids having the formula: $(K)_x$-FKA-$(K)_y$, or $(Lys)_x$-Phe-Lys-Ala-$(Lys)_y$ (SEQ ID NO: 2) wherein x and y are independently integers between 5 and 20, or x and y are independently 3, 4, 5, 6, 7, 8, 9, 10, 11, 12, 13, 14, 15, 16, 17, 18, 19 or 20, with L or D amino acid isomers, wherein optionally the peptide comprises or consists of an amino acid sequence: KKKKKKKKFKAKKKKKK (SEQ ID NO:3), with L or D amino acid isomers, with L or D amino acid isomers, and in alternative embodiments a peptide as provided herein is between about 8 to 50 amino acid residues in length, or alternatively the peptide is no more than 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues in length.

The stabilizing peptide is a modified version of poly-L-lysine (or poly-K). It wraps around the coiled coil of the S2 region, influencing the globular heads to fold back and enter the off-state. Since the modified poly-L-lysine is a positively charged peptide, it displays a strong affinity for the negatively charged glutamate side chains of the myosin.

Cell and Tissue Targeting and Penetrating

In alternative embodiments, a peptide as provided herein further comprises, or is linked to (e.g., conjugated or otherwise joined or linked to) a cell targeting or cell penetrating moiety or a chemical delivery system (CDS), for example, a peptide as provided herein can be conjugated or otherwise joined or linked to cell or a blood brain barrier (BBB) penetrating agent or moiety to accelerate or expedite delivery to the desired tissue or organ, e.g., CNS. In alternative embodiments, a peptide as provided herein, or a peptide used to practice methods provided herein, is contained within a particle, a nanoparticle, a liposome, a polyion complex micelle (PIC micelle) or equivalents thereof, that have displayed on their outer surfaces a cell penetrating or cell targeting moiety or a CDS (e.g., that can target the CNS and/or penetrate the BBB or CNS). These alternative embodiments can offer significant advantages in the treatments because a peptide as provided herein can be targeted to and/or concentrated in the desired cell, tissue or organ, thereby reducing the administered dose needed and toxicity.

In alternative embodiments, a peptide as provided herein further comprises a cell penetrating domain or motif or a tissue or organ targeting domain or motif. For example, in alternative embodiments, the cell penetrating domain or motif (or cell penetrating peptide (CPP)) comprises: a transactivating transcriptional activator (TAT) peptide from human immunodeficiency virus 1 (HIV-1); or, the CPP can comprise a Papillomaviridae CPP such as a human papillomavirus CPP; or, the CPP can be an amphipathic peptide such as MPG and Pep-1, or the amphipathic motif, Arg-Arg-Arg-Arg-Trp-Trp-Trp (SEQ ID NO:4); or penetratin, a 16-mer peptide derived from the third helix of the *Drosophila* Antennapedia homeodomain; or rabies virus glycoprotein (RVG); or prion peptide; or the L2 capsid protein of human papillomavirus. In alternative embodiments, the cell penetrating domain or motif is a non-peptidic moiety that is conjugated or otherwise attached to a myosin subfragment-2-binding peptide as provided herein; for example, the non-peptidic moiety can be an amphipathic cell-penetrating motifs comprising at least about four guanidinium groups and one or two or more aromatic hydrophobic groups (e.g., naphthalene) assembled through a central scaffold (e.g., a benzene ring).

In alternative embodiments, the tissue or organ targeting domain or motif comprises: the tripeptide Arg-Gly-Asp (RGD), which binds integrins; or the peptides CAR-SKNKDC (CAR) (SEQ ID NO:5) or CRKDKC (CRK) (SEQ ID NO:6) that selectively target injured tissues, for example, the CAR peptide binds to cell surface heparan sulfate proteoglycans (HSPGs), or any peptide that specifically binds to a tissue or organ specific cell surface polypeptide, e.g., receptor.

In one embodiment, peptides as provided herein are linked, joined or conjugated to a short peptide motif to create a penetration composition for specific transport across a biological barrier sealed by a tight junction, e.g., the BBB, e.g., as described in U.S. pat. App. Pub. no. 20060251713. In one embodiment, peptides as provided herein are linked, joined or conjugated to moiety, e.g., a peptide, which facilitates the entry of a linked molecule or particle, liposome and the like across the BBB, e.g., using a modified transit peptide as described in U.S. Patent Application No. 20160289276, or a peptide as described in U.S. patent application No. 20160287714, or a "Molecular NanoMotors (MNMs)" as described in U.S. patent application No. 20160129125.

Peptidomimetic and D-Amino Acid Forms

In alternative embodiments, a myosin subfragment-2-binding peptide as provided herein comprises some (e.g., at least about 5%, 10%, 20%, 30% or 40%) or all or substantially all (e.g., about 85%, 90% or 95%) "mimetic" or "peptidomimetic" forms, where the terms "mimetic" and "peptidomimetic" refer to a synthetic chemical compound which has substantially the same structural and/or functional characteristics of an amino acid residue in a peptide as provided herein, or in a peptide as provided herein. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

Peptides mimetic compositions as provided herein can contain any combination of non-natural structural components. In alternative aspect, mimetic compositions as provided herein comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a peptide can have all or some of its residues joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., $-C(=O)-CH_2-$ for $-C(=O)-NH-$), aminomethylene ($CH_2-NH$), ethylene, olefin ($CH=CH$), ether ($CH_2-O$), thioether ($CH_2-S$), tetrazole ($CN_4-$), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A mimetic peptide as provided herein can also comprise non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1,-2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole (alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'—N—C—N—R') such as, e.g., 1-cyclo-hexyl-3 (2-morpholinyl-(4-ethyl) carbodiimide or 1-ethyl-3 (4-azonia-4,4-dimetholpentyl) carbodiimide. Aspartyl or glutamyl can also be converted to asparaginyl and glutami-nyl residues by reaction with ammonium ions. Mimetics of basic amino acids can be generated by substitution with, e.g., (in addition to lysine and arginine) the amino acids ornithine, citrulline, or (guanidino)-acetic acid, or (guani-dino) alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by react-ing cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroac-etone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromer-curibenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing resi-due mimetics can also be generated by reaction with imi-doesters, such as methyl picolinimidate, pyridoxal phos-phate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be gener-ated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine;

methylation of main chain amide residues or substitution with N-methyl amino acids; or amidation of C-terminal carboxyl groups.

In alternative embodiments, a myosin subfragment-2-binding peptide as provided herein comprises some (e.g., at least about 5%, 10%, 20%, 30% or 40%) or all or substan-tially all (e.g., about 85%, 90% or 95%): D-amino acids, for example, one embodiment comprises an all D-amino acid peptide in a retro-inverso configuration; or, peptidomimetic residues. An amino acid of a peptide as provided herein can be replaced by an amino acid (or peptidomimetic residue) of the opposite chirality. Thus, any amino acid naturally occur-ring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

In alternative embodiments, peptides as provided herein comprise at least one, or comprise 1, 2, 3, 4, 5, 6, 7, 8, 9 or 10 or more conservative amino acid substitutions, where a conservative amino acid substitution has the same charac-teristics as the residue for which it is substituted, or the conservative substitutions are those that substitute a given amino acid in a peptide by another amino acid of like characteristics. Conservative substitutions can comprise any one of the following replacements: an aliphatic amino acid such as Alanine, Valine, Leucine and Isoleucine with another aliphatic amino acid; replacement of a Serine with a Threo-nine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. In alternative aspects, these con-servative substitutions can also be synthetic equivalents of these amino acids.

Peptide Administration In Vivo

In alternative embodiments, a peptide modulator of myo-sin subfragment-2 coiled coil stability as provided herein is administered to an individual in need thereof for: increasing exercise tolerance in a subject with heart failure; reducing hospitalization in a subject with heart failure; improving quality of life in a subject with heart failure; decreasing morbidity in a subject with heart failure; decreasing mor-tality in a subject with heart failure; modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies.

In alternative embodiments, administering of peptides as provided herein can be in the form of the peptide, or its mimetic form, or in the form of a nucleic acid that encodes the peptide.

In alternative embodiments, peptides as provided herein, or nucleic acids that encode peptides as provided herein, are administered intramuscularly, intravenously, sublingually or by direct injection into a tissue or organ, e.g., into a cardiac tissue.

In alternative embodiments, peptides as provided herein, or nucleic acids that encode peptides as provided herein, are administered as or are formulated as oral, transdermal, sustained release, controlled release, delayed release, sup-pository, oral, powder, aerosol or sublingual formulations.

Gene Therapy and Gene Delivery Vehicles

In alternative embodiments, methods as provided herein comprise use of nucleic acid delivery systems to deliver a payload of a peptide-encoding nucleic acid or gene, or a peptide-expressing nucleic acid, transcript or message, to a cell or cells in vitro, ex vivo, or in vivo, e.g., as gene therapy delivery vehicles.

In alternative embodiments, expression vehicle, vector, recombinant virus, or equivalents used to practice methods as provided herein are or comprise: an adeno-associated virus (AAV), a lentiviral vector or an adenovirus vector; an AAV serotype AAV5, AAV6, AAV8 or AAV9; a rhesus-derived AAV, or the rhesus-derived AAV AAVrh.10hCLN2; an organ-tropic AAV; and/or an AAV capsid mutant or AAV hybrid serotype. In alternative embodiments, the AAV is engineered to increase efficiency in targeting a specific cell type that is non-permissive to a wild type (wt) AAV and/or to improve efficacy in infecting only a cell type of interest. In alternative embodiments, the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid. It is well known in the art how to engineer an adeno-associated virus (AAV) capsid in order to increase efficiency in targeting specific cell types that are non-permissive to wild type (wt) viruses and to improve efficacy in infecting only the cell type of interest; see e.g., Wu et al., Mol. Ther. 2006 September; 14(3):316-27. Epub 2006 Jul. 7; Choi, et al., Curr. Gene Ther, 2005 June; 5(3):299-310.

For example, the rhesus-derived AAV AAVrh.10hCLN2 or equivalents thereof can be used, wherein the rhesus-derived AAV may not be inhibited by any pre-existing immunity in a human; see e.g., Sondhi, et al., Hum Gene Ther. Methods. 2012 October; 23(5):324-35, Epub 2012 Nov. 6; Sondhi, et al., Hum Gene Ther. Methods. 2012 Oct. 17; teaching that direct administration of AAVrh.10hCLN2 to the CNS of rats and non-human primates at doses scalable to humans has an acceptable safety profile and mediates significant payload expression in the CNS.

Also, for example, AAV vectors specifically designed for cardiac gene transfer (a cardiotropic AAV) can be used, e.g., the AAVM41 mutant having improved transduction efficiency and specificity in the myocardium, see, e.g., Yang, et al. Virol J. 2013 Feb. 11; 10(1):50.

Because adeno-associated viruses (AAVs) are common infective agents of primates, and as such, healthy primates carry a large pool of AAV-specific neutralizing antibodies (NAbs) which inhibit AAV-mediated gene transfer therapeutic strategies, the methods of the invention comprise screening of patient candidates for AAV-specific NAbs prior to treatment, especially with the frequently used AAV8 capsid component, to facilitate individualized treatment design and enhance therapeutic efficacy; see, e.g., Sun, et al., J. Immunol. Methods. 2013 Jan. 31; 387(1-2):114-20, Epub 2012 Oct. 11.

In alternative embodiments, provided are pharmaceutical formulations comprising a peptide or polypeptide as provided herein, or nucleic acids encoding peptides or polypeptides as provided herein, which can be formulated and administered using any formulations, protocols or techniques known in the art, for example, pharmaceutical formulations or vaccines as provided herein can be administered as peptides, or can be administered in the form of nucleic acids that encode the bioactive peptides or proteins.

For example, in alternative embodiments the bioactive peptide- or protein-encoding nucleic acid(s) can be a DNA encoding one or more peptides or proteins as provided herein, and/or the DNA can be carried in an expression vehicle such as a viral vector, for example an adenovirus vector such as an Ad5 or adeno-associated vector (AAV). In alternative embodiments, recombinant adenoviruses as used in vaccines as provided herein can be as described in U.S. patent application no. US 20200399323 A1, which describes for example recombinant adenoviruses including a deletion in or of the E1 region or any deletion that renders the virus replication-defective, for example, the replication-defective virus can include a deletion in one or more of the E1, E3, and/or E4 regions; or, can be as described in U.S. patent application no. US 20190382793 A1, which described how to make recombinant adenoviruses for gene therapy.

In alternative embodiments, bioactive peptide- or protein-encoding nucleic acid(s) as provide herein can be an RNA, for example, mRNA, which can be formulated in a lipid formulation or a liposome and injected for example intramuscularly (IM), for example using formulations and methods as described in U.S. patent application no. US 20210046173 A1, which describes delivering to a subject (for example, via intramuscular administration) a bioactive peptide- or protein-encoding nucleic acid(s) as provide herein that comprises a RNA (for example, mRNA) that comprises an open reading frame (ORF) that comprises (or consists of, or consists essentially of) a coding sequence for a bioactive peptide- or protein-encoding nucleic acid(s) as provide herein; wherein optionally the RNA (or the DNA-carrying expression vehicle) can be formulated in a liposome, or a lipid nanoparticle (LNP), or nanoliposome, that comprises: non-cationic lipids comprise a mixture of cholesterol and DSPC, or a PEG-lipid, or PEG-modified lipid, or LNP, or an ionizable cationic lipid; or a mixture of (13Z,16Z)—N,N-dimethyl-2-nonylhenicosa-12,15-dien-1-amine, cholesterol, DSPC, and PEG-2000 DMG. In alternative embodiments, the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA), or, the PEG-lipid is PEG coupled to dimyristoylglycerol (PEG-DMG). In alternative embodiments, the LNP comprises 20-99.8 mole % ionizable cationic lipids, 0.1-65 mole % non-cationic lipids, and 0.1-20 mole % PEG-lipid. In alternative embodiments, the LNP comprises an ionizable cationic lipid selected from the group consisting of (2S)-1-({6-[(3)]-cholest-5-en-3-yloxy]hexyl}oxy)-N,N-dimethyl-3-[(9 Z)-octadec-9-en-1-yloxy]propan-2-amine; (13Z, 16Z)—N,N-dimethyl-3-nonyldocosa-13,16-dien-1-amine; and N,N-dimethyl-1-[(1S,2R)-2-octylcyclopropyl]heptadecan-8-amine; or a pharmaceutically acceptable salt thereof, or a stereoisomer of any of the foregoing. In alternative embodiments, the PEG modified lipid comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In alternative embodiments, the ionizable cationic lipid comprises: 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), (13Z, 16Z)—N,N-dimethyl-3-nonyldocosa-13,16-dien-1-amine, (12Z,15Z)—N,N-dimethyl-2-nonylhenicosa-12,15-dien-1-amine, and N,N-dimethyl-1-[(1S,2R)-2-octylcyclopropyl] heptadecan-8-amine. In one embodiment, the lipid is (13Z,

19

16Z)—N,N-dimethyl-3-nonyldocosa-13,16-dien-1-amine or N,N-dimethyl-1-[(1S,2R)-2-octylcyclopropyl]heptade-can-8-amine, each of which are described in PCT/US2011/052328, the entire contents of which are hereby incorporated by reference. In some embodiments, a non-cationic lipid of the disclosure comprises 1,2-distearoyl-sn-glycero-3-phos-phocholine (DSPC), 1,2-dioleoyl-sn-glycero-3-phospho-ethanolamine (DOPE), 1,2-dilinoleoyl-sn-glycero-3-phos-phocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocho-line, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilino-lenoyl-sn-glycero-3-phosphoethanolamine, 1,2-diarachi-donoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

In alternative embodiments, peptides as provided herein, or nucleic acids that encode peptides as provided herein, are administered to individuals or patients at risk of heart disease, e.g., individuals or patients that exhibit one or more risk factors comprising: long-standing uncontrolled hyper-tension, uncorrected valvular disease, chronic angina, recent myocardial infarction, congenital predisposition to heart disease and/or pathological hypertrophy.

In alternative embodiments, peptides as provided herein, or nucleic acids that encode peptides as provided herein, are administered therapeutically or prophylactically (preventa-tively) to individuals or patients diagnosed as having a genetic predisposition to heart failure, and/or have a familial history of heart failure.

In alternative embodiments, methods as provided herein comprise administering to at least one second therapeutic or therapy, e.g., a second heart failure drug or therapy, such as e.g., a beta blocker, an ionotrope, a diuretic, ACE-I, AII antagonist, BNP, or a Ca++ channel blocker.

In alternative embodiments, peptides as provided herein, or nucleic acids that encode peptides as provided herein, are administered therapeutically or prophylactically (preventa-tively) to organ transplant recipients, e.g., heart transplant recipient.

Formulations and Pharmaceutical Compositions

In alternative embodiments, the invention provides phar-maceutical formulations or compositions comprising a pro-tein or a peptide as provided herein. In alternative embodi-ments, the invention provides pharmaceutical formulations or compositions for use in in vivo, in vitro or ex vivo methods for therapeutic or prophylactic (preventatively) administration to individuals or patients diagnosed as having a genetic predisposition to heart failure, and/or have a familial history of heart failure.

In alternative embodiments, the pharmaceutical compo-sitions used to practice methods as provided herein can be administered parenterally, topically, orally or by local administration, such as by aerosol or transdermally, or for example, a nucleic acid administered intramuscularly. These pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton PA ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formu-lations and/or carriers used to practice methods as provided herein can be in forms such as tablets, pills, powders, capsules, liquids, gels, syrups, slurries, suspensions, etc., suitable for in vivo, in vitro or ex vivo applications.

In alternative embodiment, compounds (e.g., formula-tions) used to practice methods as provided herein can comprise a solution of compositions (which include pep-tidomimetics, racemic mixtures or racemates, isomers, ste-reoisomers, derivatives and/or analogs) disposed in or dis-solved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglyc-erides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice methods as provided herein can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concen-tration of active agent in these formulations can vary widely, and can be selected primarily based on fluid volumes, viscosities and the like, in accordance with the particular mode of in vivo, in vitro or ex vivo administration selected and the desired results.

The compositions and formulations used to practice meth-ods as provided herein can be delivered by the use of liposomes. By using liposomes, particularly where the lipo-some surface carries ligands specific for target cells, or are otherwise preferentially directed to a specific tissue or organ type, one can focus the delivery of the active agent into a target cells in an in vivo, in vitro or ex vivo application.

Nanoparticles, Nanolipoparticle and Liposomes

Also provided are nanoparticles, nanolipoparticles, vesicles and liposomal membranes comprising peptides and polypeptides used to practice methods as provided herein.

Provided are multilayered liposomes comprising com-pounds used to practice methods as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice methods as provided herein.

Liposomes can be made using any method, e.g., as described in Park, et al., U.S. Pat. Pub. No. 20070042031, including method of producing a liposome by encapsulating an active agent (nucleic acids and polypeptides as provided herein), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice methods as provided herein comprise a substituted ammonium and/or polyanions, e.g., for targeting delivery of a nucleic acid, peptide or polypeptide as provided herein, as described e.g., in U.S. Pat. Pub. No. 20070110798.

The invention also provides nanoparticles comprising a nucleic acid, a peptide or polypeptide as provided herein used to practice methods as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice methods as provided herein to mammalian cells in vivo, in vitro or ex vivo, as described, e.g., in U.S. Pat. Pub. No. 20050136121.

Products of Manufacture and Kits

Provided are products of manufacture and kits for practicing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13% 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR-Basics: From Background to Bench, First Edition, Springer Verlag, Germany.

Example 1: Exemplary Peptides for Modulating
Myosin Subfragment-2 Coiled Coil Stability This example describes and demonstrates that methods and peptide compositions as provided herein when administered to an individual in need thereof are effective for: increasing exercise tolerance in a subject with heart failure; reducing hospitalization in a subject with heart failure; improving quality of life in a subject with heart failure; decreasing morbidity in a subject with heart failure; decreasing mortality in a subject with heart failure; modulating skeletal muscle activity for purposes of impacting patient weight; and/or, modulating skeletal muscle activity for purposes of ameliorating consequences of skeletal muscle diseases such as sarcopenia, muscular dystrophies, muscle cramps, and nemaline myopathies.

Myosin Regulation

Myosin and actin are the primary functional proteins involved in muscular contraction. In the contractile filament of muscle, these two proteins interact to allow muscle contraction (Kron et al., 1991). There are three major types of muscle: smooth, skeletal, and cardiac. An important aspect of the function of muscle is the regulation of muscle contraction. Typically, skeletal and cardiac muscle cells regulate contraction through calcium and the troponin-tropomyosin complex. When calcium ions are released by the sarcoplasmic reticulum, they bind to the troponin, thus causing tropomyosin to shift on the actin; this action exposes the myosin binding sites on the actin, allowing contraction to occur (Spudich & Watt, 1971). However, the smooth muscle uses a different mechanism to regulate actin-myosin interaction. The actin and myosin arrange themselves into functional units when contraction is required, but the myosin protein enters an off-state where the myosin heads fold back and become inactive (Campbell et al., 2019). The off-state of myosin that is seen in smooth muscle can also be observed in cardiac and skeletal muscle. Therefore, the folding back of myosin heads into an off-state is a secondary regulator of contraction in voluntary muscle.

Figure 1:
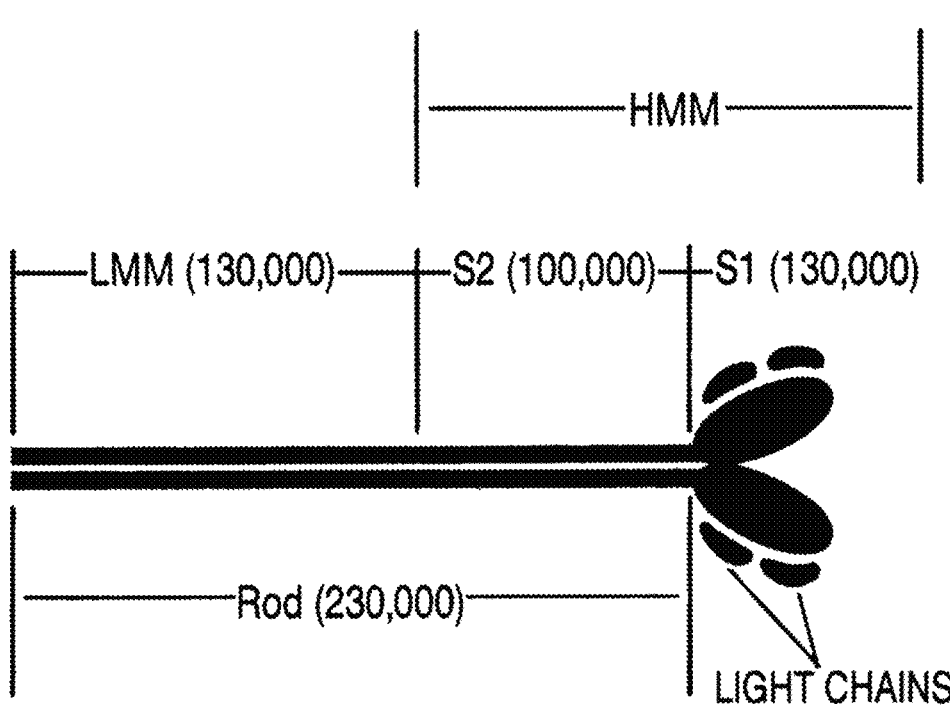
FIG. 1 schematically illustrates how the structure of myosin in skeletal muscle is divided into multiple regions, as described in detail in Example 1, below.

The structure of myosin in skeletal muscle is divided into multiple regions (FIG. 1). The long, tail-like portion of the myosin that is part of the thick filament is known as the light meromyosin (LMM), whereas the heavy meromyosin (HMM) consists of a protein chain terminating in two globular heads. The HMM can be further divided into subfragment-1 (S1) and subfragment-2 (S2). Myosin subfragment-2 links the LMM with the globular heads of the S1 region, and is responsible for the regulation of the on and off-states of myosin. When inactive, myosin bends at the S1-S2 hinge, and the heads bind to the S2 region (Singh et al., 2018).

Mutations in myosin subfragment-2 are known to cause conditions such as the aforementioned cardiovascular diseases of hypertrophic cardiomyopathy (HCM), dilated cardiomyopathy (DCM), and chronic congestive heart failure (CHF). For example, the deletion mutation delE930 in the S2 region of human beta-cardiac myosin is associated with a highly lethal form of hypertrophic cardiomyopathy (Waldmüller et al., 2003) While HCM results in an increased rate of contraction that causes arrhythmia and a possibility of embolic stroke, both DCM and CHF are characterized by a weakening in the heart's ability to pump blood (Reed & Sueta, 2015; Choudhry et al., 2019). The structural effects of certain mutations that cause these diseases can be reversed by controlling the contractile ability of the muscle at a biochemical level. By influencing the structural integrity of myosin subfragment-2, it is possible to either encourage myosin to enter the off-state or prevent myosin from folding back and binding to the S2 region (Singh et al., 2018).

Peptides to Modulate the Stability of the Coiled Coil Structure of Myosin Subfragment-2

Peptides have been designed to modulate the stability of the coiled coil structure of myosin subfragment-2 (Singh, 2017). The intent of these peptides is to regulate muscle contraction by influencing the ability of myosin to interact with actin. A peptide that can reduce the contraction of cardiac muscle (a stabilizing peptide has the effect of decreasing muscle contraction) promises applications in treating the effects of hypertrophic cardiomyopathy (HCM). On the other hand, the effects of dilated cardiomyopathy (DCM), and chronic congestive heart failure (CHF) could be alleviated by a peptide that works to enhance muscle contraction (a destabilizing peptide has the effect of increasing muscle contraction).

Figures 2, 3:
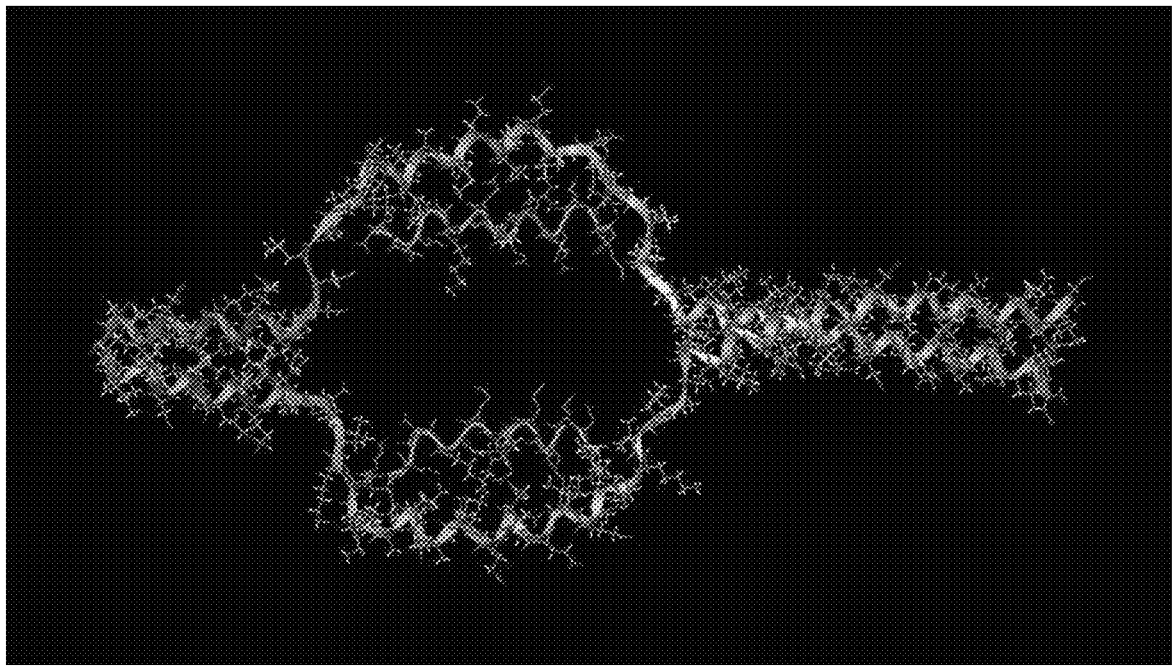
FIG. 2 illustrates an image showing how an exemplary stabilizing peptide wraps around the coiled coil of the S2 myosin region influencing the globular heads to fold back and enter the off-state, and that the polarity of the interaction allows the peptide to specifically target the S2 coiled coil, as described in detail in Example 1, below.
FIG. 3 illustrates an image showing how one myosin dimer will interact with two exemplary destabilizing peptides at once, and as a result the myosin heads are unable to bind to the S2 region, preventing them from ever entering the off-state, as described in detail in Example 1, below.

The stabilizing peptide is a modified version of poly-L-lysine. It wraps around the coiled coil of the S2 region, influencing the globular heads to fold back and enter the off-state. Since the modified poly-L-lysine is a positively charged peptide, it displays a strong affinity for the negatively charged glutamate side chains of the myosin. The polarity of the interaction allows the peptide to specifically target the S2 coiled coil (FIG. 2). Since the stabilized myosin dimer will be more likely to be in the off-state, the stabilizing peptide has the effect of decreasing muscle contraction (Taei, 2013).

The destabilizing peptide consists of a 19 amino acid sequence that is based on a modification of a section of myosin subfragment-2. The peptide was designed to destabilize the myosin S2 by competing with the intrinsic interactions of the coiled coil strands with each other. The peptide binds to one strand of the myosin dimer, outcompeting the bond of the coiled coil (Singh, 2017). Therefore, one myosin dimer will interact with two destabilizing peptides at once (FIG. 3). As a result, the myosin heads are unable to bind to the S2 region, preventing them from ever entering the off-state. In a destabilized myosin dimer, the heads are always available to bind to actin, leading to a significant increase in muscle contraction.

Fluorophores

A fluorophore is a fluorescent chemical compound that can emit light upon excitation. Typically, these compounds are used to label other peptides so they can be used in a variety of analytical methods such as fluorescent imaging and spectroscopy. The size and molecular mass of a fluorophore resembles that of some other peptides. If the fluorophore doesn't have an impact on functionality of the peptide, it can be hypothesized that other similar peptides could also be attached to the peptide without impeding its function. Fluorescein isothiocyanate (FITC) and tetramethylrhodamine (TRITC) are two commonly used fluorophores (Qadan, 2021).

Myosin Binding Protein C (MyBP-C)

Myosin binding protein C (MyBP-C) acts as another force regulator in muscle that binds to myosin subfragment-2. MyBP-C is anchored in the LMM, but interacts with myosin S2 to influence the attachment of myosin heads. In effect, the protein works similar to the stabilizing peptide, influencing the heads of myosin to enter the off-state by folding back (Singh et al., 2018). Certain monoclonal antibodies have been researched in relation to their abilities to regulate muscle contraction. Single molecule assays involving the MF 20 antibody (which binds to LMM) have shown no significant effect on percent contraction (Singh, 2017). However, these antibodies have not been tested in a whole myofibril that includes other components like MyBP-C.

Muscle and Sarcomere

Muscle is a soft tissue present in nearly all the metazoans. Contraction of the muscle imparts several important physiological functions such as locomotion, circulation and peristalsis of the digestive tract. Muscle is present in three forms namely skeletal, smooth and cardiac muscle. Contraction of these muscle types is achieved by the acto-myosin interaction between the myosin thick filament and actin thin filament upon enzymatic cleavage of the adenosine triphosphate (ATP) by ATPase activity of myosin subfragment S1 heads to provide energy (Huxley, A. F. 1964; Lymn, R. W. and Taylor, E. W. 1971; Huxley, A. F. and Niedergerke, R. 1954).

Figures 4, 5:
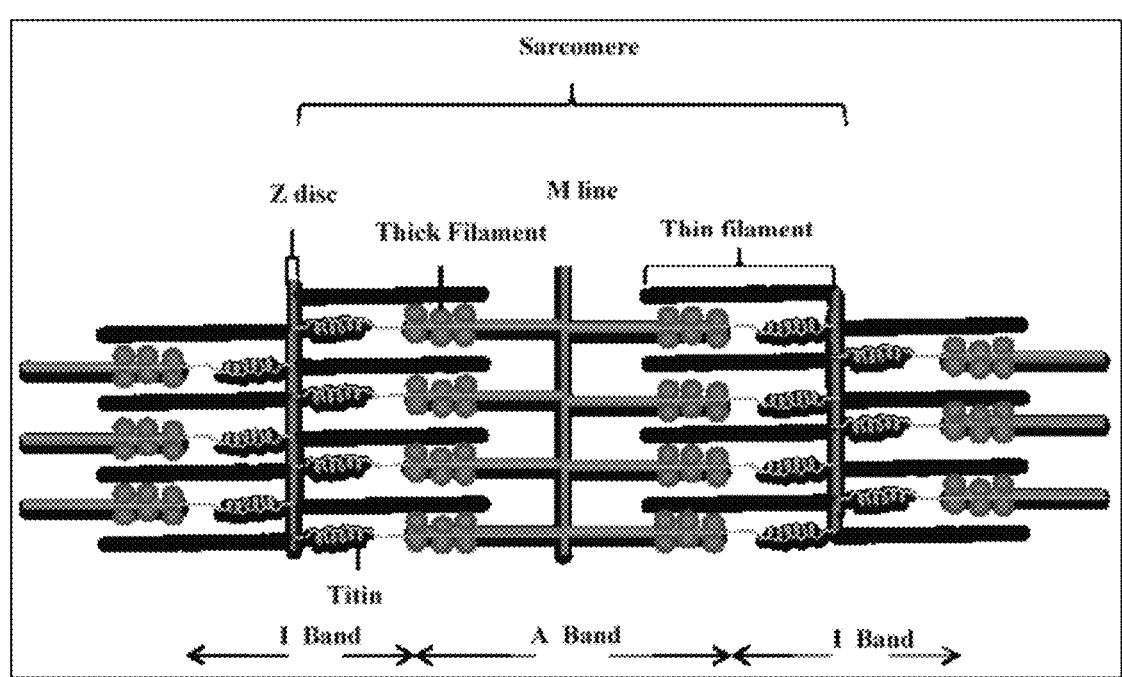
FIG. 4 schematically illustrates a schematic of a sarcomeric unit of muscle with all the parts labelled, as described in detail in Example 1, below.
FIG. 5 schematically illustrates a Myosin II coiled coil structure with different parts labelled from N terminal region to C terminal region (from right to left), as described in detail in Example 1, below.

FIG. 4 illustrates a schematic of a sarcomeric unit of muscle with all the parts labelled.

The sarcomere is a functional unit of muscle present in skeletal and cardiac muscle types but absent in smooth muscle type (Wang, K. 1985). The sarcomere is a precise arrangement of all the contractile proteins of a muscle in a repetitive manner. A schematic of the muscle sarcomere is detailed in figure (FIG. 4). The length of the sarcomere is measured between two I bands of a muscle myofibril. An I band is followed by an A band followed by another I band and so on in a repetitive manner. The I band contains Cap Z which is the anchor point of actin thin filaments, where the new actin monomers are added to form the filamentous thin actin filament. The A band contains the central H zone, and this H zone consists of an M line which is the anchor point of myosin thick filament. At M line the myosin filaments are anchored by the interaction of light meromyosin (LMM) of several myosin thick filaments. Spanning both the directions away from H zone in A band there is the overlap of myosin thick filament and actin thin filaments. Hence, when the myofibril is viewed under a microscope, there is a lighter I band followed by a dense A band (Price, H. M. 1963).

In skeletal muscles, the myofibrils are present in tight bundles, thus these sarcomeres appear in a more regular manner giving the skeletal muscles a much more striated appearance (Price, H. M. 1963). Even though sarcomeres are present in the cardiac muscle, the myofibrillar bundles are more branched rather than a neat stack compared to skeletal muscles, thus cardiac muscles do not have as regular striations (Challice, C. E. and Viragh, S. 1973; Muir, A. R. 1965). Smooth muscle has a spindle shaped association of actin and myosin, but they have a related contractile apparatus to skeletal and cardiac muscle (Cooke, P. 1976). The striated muscle contractile apparatus comprises of actin thin filaments, myosin thick filament, tropomyosin, troponin complex and myosin binding protein C.

Myosin

Myosin is a superfamily of ATP dependent motor protein, where hydrolysis of ATP drives the movement of the myosin on actin (Ruppel, K. M., and Spudich, J. A. 1996). Myosin is a large protein with a molecular weight of 220 kDa and comprises approximately 1936 amino acids in the heavy chain with variations due to different genes and alternative splicing. The myosin protein has an N-terminal globular head and a long α-helical tail towards the C-terminal end.

FIG. 5 illustrates a schematic representation of Myosin II coiled coil structure with different parts labelled from N terminal region to C terminal region (from right to left). The myosin thick filament comprises the majority of the contractile apparatus. Two heavy chains and four light chains form a dimeric subunit of the myosin filament. The dimers of myosin in thick filaments are formed by the coiled coil formation of long α-helical tail at the C-terminal end of the myosin thick filament, which results in two free and independent myosin globular heads at the N-terminal end (Warrick, H. M., and Spudich, J. A. 1987; Al-Khayat, H A. 2013). The myosin heavy chain is structurally classified into two parts heavy meromyosin and light meromyosin. Schematic of myosin II coiled coil structure is detailed in the figure (FIG. 5). Heavy meromyosin is further divided into two subfragments, namely myosin subfragment 1 (S1) and myosin subfragment 2 (S2) connected by the myosin S1-S2 hinge (Rayment, I., and Holden, H. M. (1994). Myosin S1 forms the two free globular heads of the myosin at its N-terminal end, each comprised of the ATP binding domain and actin binding site. Myosin S1 heads have the essential role of binding and hydrolysis of ATP at the ATP binding site and actin association at the actin binding site. The myosin S1 has two myosin light chains bound to them namely, myosin essential light chain and myosin regulatory light chain. Following the myosin S1-S2 hinge is the myosin S2 which is a coiled-coil linker between myosin subfragment 1 and light meromyosin. The light meromyosin is an extensive coiled coil which polymerizes with the light meromyosin of other myosin to form the thick filament backbone (Goodson, H. V. and Spudich, J. A. 1993).

Actin

Globular G-actin with bound ATP can polymerize to form the filamentous F-actin (Rees, M. K., and Young, M. 1967). Cap Z on I band of sarcomere marks the actin filament assembly center where new ATP bound G-actin monomers are added to maintain the F-actin assembly. G-actin has a molecular weight of 42 kDa. Every seventh actin on actin thin filament binds troponin and associated tropomyosin (Ebashi et al., 1969). The thin filament spans from the Cap Z of I band to the perimeter of H zone of A band of sarcomere.

Familial Hypertrophic Cardiomyopathy

Figures 6, 7:
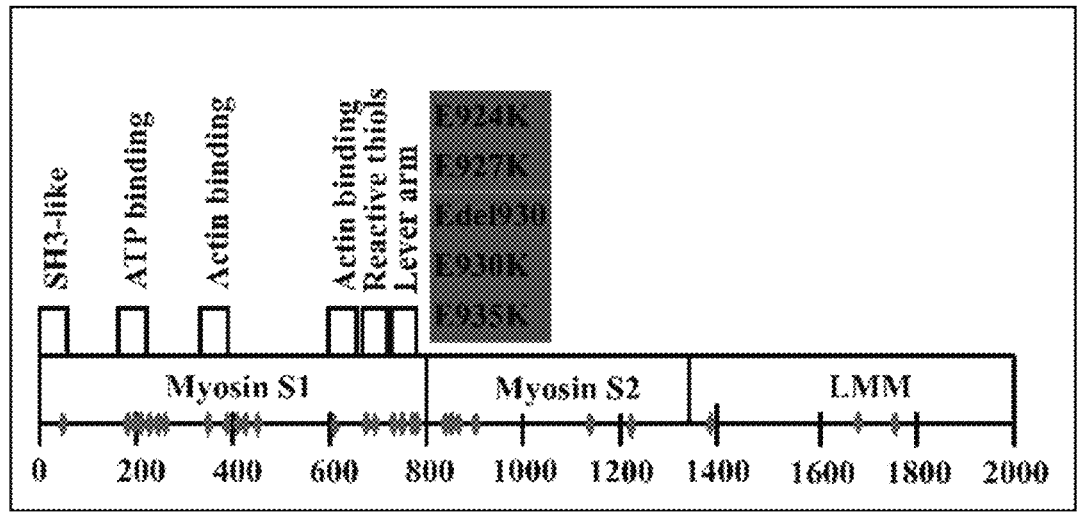
FIG. 6 illustrates an image of the anatomy of cardiomyopathic hearts: images from left to right: FHC human heart with asymmetrical thickening of ventricles leaves less blood volume for pumping; healthy heart with plenty of negative space in the left ventricle; heart with dilated cardiomyopathy phenotype, as described in detail in Example 1, below.
FIG. 7 schematically illustrates familial hypertrophic cardiomyopathy point mutations (blue diamonds) across MYH7 gene with point mutations highlighted at the proximal myosin S2 region, as described in detail in Example 1, below.

FIG. 6 illustrates an image of the anatomy of cardiomyopathic hearts. From left to right, FHC human heart with asymmetrical thickening of ventricles leaves less blood volume for pumping; healthy heart with plenty of negative space in the left ventricle; heart with dilated cardiomyopathy phenotype.

Familial hypertrophic cardiomyopathy (FHC) is an autosomal dominant genetic disorder of the heart muscles. FHC results in the enlargement of heart and potentially sudden death of the person (Semsarian et al., 2015). Mutations for FHC are mostly point mutations and missense mutations in proteins of contractile apparatus of cardiac muscle. Most mutations are found to be in the myosin heavy chain followed by cardiac myosin binding protein C and fewer mutations reported in myosin light chains, titin, actin, tropomyosin and troponin complex (Erdmann et al., 2003; Richard et al., 2003; McNally et al., 2015). Haploinsufficiency of mutant MyBPC is a reason for this disorder when a single allelic product is not enough to rescue the phenotype. A single mutation in protein of contractile apparatus of heart muscle would cause such a detrimental effect could be imagined, since the heart muscle undergoes constant cycles of contraction and relaxation to circulate the blood throughout the body of an organism. Any slight change in heart's contractile apparatus would throw off this tight regulation which would result in this severe disorder.

There are two types of more prevalent cardiomyopathies caused by mutations to contractile proteins, namely familial hypertrophic cardiomyopathy (FHC) and dilated cardiomyopathy (DCM). Anatomy of FHC and DCM heart compared to normal human heart in figure (FIG. 5). FHC results in the hypertrophy of the ventricles of the heart. Ventricles of FHC heart are thickened due to hypertrophy of ventricular muscles. Thickening of the ventricles of heart significantly reduces the negative space present in the ventricles of heart thus decreasing the amount of blood pumped through a FHC heart resulting in the sudden death of the person suffering from FHC. In DCM the ventricles of heart are loosened and thin, even though the negative space in ventricles of DCM heart is increased but the ventricular muscles of DCM are weak to pump the blood causing the death of the person by heart failure (Cho et al., 2016; Semsarian et al., 2015; Jean, M. 2003).

FIG. 7 schematically illustrates familial hypertrophic cardiomyopathy point mutations (blue diamonds) across MYH7 gene with point mutations highlighted at the proximal myosin S2 region.

FHC point mutations have been reported all along the cardiac muscle myosin protein (Richard et al., 2003). Mutation in the myosin S1 head would affect the binding of myosin S1 heads to actin thin filament upon muscle contraction, thus having a strong implication on the force output of the cardiac muscle. Mutations in the LMM region could be argued that it would interfere with bundling of LMM to each other at M line thus affecting the overall assembly of myosin thick filament on the M line of sarcomere. But there is a cluster of mutations in the proximal myosin S2 region reported for cardiomyopathy highlighted in the figure (FIG. 7). The families suffering from these myosin S2 cardiomyopathic mutations had 50% of their family dead by sudden cardiac arrests (Tesson et al., 1998; Waldmüller et al., 2003). The myosin S2 has not been assigned any functional role yet apart from being a coiled coil linker between myosin S1 heads and extensive coiled coil LMM. This begs the question if there is more functional role to myosin S2 rather than just being a coiled coil linker. Myosin S2 coiled coil might have a role in regulating the acto-myosin interaction and overall force produced.

Stabilizer Peptide is Specific to Myosin S2 Coiled Coil and Stabilizes the Myosin S2 Coiled Coil Stabilizer peptide is specific to myosin S2 coiled coil and stabilizes the myosin S2 coiled coil thus decreasing the amount of force produced. The stabilizer peptide designed earlier through computer simulations binds and wraps around the proximal myosin S2 coiled coil at amino acids 924-942. This peptide was designed to stabilize the myosin S2 coiled coil in the context of reducing the amount of myosin S1 heads available to bind actin.

The first test is to check the binding specificity and efficiency of stabilizer peptide to myosin S2 coiled coil. Competitive Enzyme Linked Immunosorbent Assay (cELISA) is performed to confirm the binding specificity and affinity of the stabilizer peptide to myosin S2 coiled coil. A site-specific polyclonal antibody raised against a single α-helix of myosin S2 is used to compete with the stabilizer peptide to bind myosin S2 in rabbit skeletal myosin molecule as well as human cardiac myosin S2 peptide. The wells are coated with rabbit skeletal myosin and to the well is added an appropriate amount of human cardiac myosin S2 peptide that binds the polyclonal antibody and when washed away there won't be enough polyclonal antibody to bind myosin S2 of rabbit skeletal myosin. This leads to low or no color development leading to lower OD. Expected result is to see the change in OD from lower OD with no stabilizer to higher OD with increasing amounts of stabilizer peptide and then again back to lower OD with higher amounts of stabilizer peptide would be able to confirm the binding efficiency of stabilizer peptide to myosin S2 as well convey the cross-specificity of stabilizer of myosin S2 of human cardiac and rabbit skeletal myosin.

After confirming the specificity and binding affinity of the stabilizer peptide to myosin S2, next is to check whether the stabilizer peptide has an effect over myosin S2 coiled coil stability. The gravitational force spectrometer (GFS) assay is performed to confirm the stabilization of myosin S2 coiled coil by binding of stabilizer peptide. In this assay, the actin and myosin S1 rigor binding is used to suspend the myosin molecule between the immobile edge and a mobile bead. The initial hypothesis is that to uncoil the myosin S2 in presence of stabilizer peptide requires more force than to uncoil the myosin S2 in absence of stabilizer peptide.

Next test is to check whether this stabilization of myosin S2 coiled coil has an effect over contraction of the myofibril. The myofibril contractility assay is performed to confirm the effect of the stabilizer peptide. In this assay length of sarcomere are measured before and after adding ATP to simulate contraction in myofibrils. Control would be to measure the shortening of sarcomeres without any stabilizer peptide and test the shortening of sarcomeres in the presence of stabilizer peptide. Expected result is to observe less contraction in the sarcomeres of myofibrils treated with stabilizer peptide to the myofibrils sans stabilizer peptide. This reduction in amount of contraction in sarcomeres of stabilizer treated myofibrils would confirm that stabilized myosin S2 coiled coil would reduce the amount of myosin S1 heads available to bind actin thus reducing the amount of force produced through acto-myosin interaction.

The in vitro motility assay of actin filaments over myosin AMM treated with stabilizer peptide confirms the effect of stabilizer peptide over amount of force produced through acto-myosin interaction. The control for this assay is purified rabbit skeletal myosin HMM immobilized on dichloromethylsilane treated coverslip and actin filaments allowed to slide over these immobilized myosin HMM. Test would be to allow the actin filament to slide over the same immobilized myosin HMM by adding stabilizer peptide to the same setup. Thus calculating sliding filament velocity of actin thin filaments over myosin HMM in absence and presence of stabilizer peptide confirms the effect of stabilizer peptide over the total force produced through acto-myosin interaction. The initial hypothesis is to observe a reduction in sliding filament velocity of actin filaments over myosin in presence of stabilizer peptide.

All of these experiments performed together validate the binding specificity and affinity of the stabilizer peptide to the myosin S2 region. These experiments also confirm the stabilizing effect by binding of stabilizer peptide to myosin S2 coiled coil. Its stabilization results in reduction of contractility in myofibrils along with the amount of force produced through acto-myosin interaction.

Destabilizer Peptide is Specific to Myosin S2 Coiled Coil and Destabilizes the Myosin S2 Coiled Coil The destabilizer peptide is specific to myosin S2 coiled coil and destabilizes the myosin S2 coiled coil thus increasing the amount of force produced.

The destabilizer peptide was designed through computer simulations to interfere with the formation of the myosin S2 coiled coil. The destabilizer peptide binds to one α-helix of the myosin S2 coiled coil and disrupts the natural coiled coil formation of two individual α-helices of myosin S2 molecule. The destabilizer peptide was designed against the same proximal myosin S2 region amino acid residues from 924-942 as the site-specific polyclonal antibody with the intention of producing a similar effect. This peptide was designed to destabilize the myosin S2 coiled coil in the anticipation of increasing the amount of contraction and force produced through acto-myosin interaction.

The first assay is to check the binding specificity and efficiency of destabilizer peptide to myosin S2 coiled coil. cELISA is performed as previously with the polyclonal antibody raised against myosin S2 competing with the destabilizer peptide to bind the myosin S2 region of rabbit skeletal myosin coated on the wells and human cardiac myosin S2 suspended in the wells. Similar effects are observed as explained earlier for the stabilizer peptide. The lower-higher-lower OD trend depending on increasing concentration of destabilizer peptide confirms the binding specificity and affinity of destabilizer peptide to myosin S2.

After confirming the binding specificity and affinity of the destabilizer peptide to myosin S2, the next assay is to test whether the destabilizer peptide destabilizes the myosin S2 coiled coil. Gravitational force spectrometer (GFS) confirms the effect of destabilizer peptide over the flexibility and stability of myosin S2 coiled coil. Again the actin myosin S1 binding property is used to suspend the myosin molecule between immobile edge and mobile bead. The GFS assay is performed with the myosin molecule in presence and absence of destabilizer peptide. Force distance curve of myosin molecule in presence and absence of destabilizer peptide establish the effect of the destabilizer peptide. The initial hypothesis is that the force required to pull apart the myosin coiled coil in the presence of the destabilizer peptide is less than when compared with the myosin molecule in absence of destabilizer peptide thus confirming the destabilizing effect of destabilizer on myosin S2 coiled coil.

After confirming the destabilization of myosin S2 coiled coil by destabilizer peptide, the next experiment is to see the effect of this destabilization on myofibril contraction. The myofibril contractility assay establishes the effect of the destabilizer. The length of the sarcomeres are measured in myofibrils before and after adding ATP to establish the control and next assay would be to measure the length of sarcomeres in myofibrils treated with destabilizer. The initial hypothesis is that the percent contraction observed in myofibrils treated with destabilizer is more than compared to that of sarcomeres in myofibrils without the destabilizer treatment. This assay confirms that destabilization of myosin S2 coiled coil increases contraction in myofibrils and thus causes a net increase in force production through acto-myosin interaction.

Increase in force production due to destabilization of myosin S2 coiled coil with destabilizer peptide could be tested by measuring the actin sliding velocity of myosin HMM treated with destabilizer peptide. The in vitro motility of actin filaments sliding over HMM in the presence and absence of destabilizer peptide is performed. The initial hypothesis is to observe a higher sliding velocity of actin over myosin HMM treated with destabilizer peptide compared to HMM without destabilizer peptide. This increase in actin sliding velocity confirms that destabilization of myosin S2 coiled coil increases the amount of force produced through acto-myosin interaction.

All these experiments performed together confirm the binding specificity and affinity of the destabilizer peptide to the myosin S2 region. Destabilization of myosin S2 coiled coil by destabilizer peptide would result in increase in amount of myofibril contraction and amount of force produced through acto-myosin interaction.

Competitive ELISA confirms the binding specificity and affinity of the stabilizer and the destabilizer peptide to the myosin S2 coiled coil. MyBPC has been already proven to bind myosin at LMM and myosin S2. Gravitational force spectroscopy verifies the stabilization of the myosin S2 coiled coil by binding of MyBPC and the stabilizer peptide by higher amount of force required to pull myosin S2 coiled coil apart in presence of these molecules. On the other hand, the gravitational force spectrometer (GFS) establishes the destabilization of myosin S2 coiled coil by destabilizer peptide by observing a lower amount of force required to pull myosin S2 coiled coil in presence of destabilizer peptide.

The myofibril contractility assay would confirm the effect of stability of myosin S2 over the myofibril contraction. Stabilizer peptide stabilizes the myosin S2 coiled coil and reduction in the percentage of sarcomere shortening in presence of stabilizer peptide compared to sarcomere shortening in absence of it and confirms that the stable myosin S2 reduces the amount of contraction in myofibrils. The destabilizer peptide makes the myosin S2 coiled coil unstable and increased sarcomere shortening in myofibrils treated with destabilizer peptide compared to myofibrils without the destabilizer peptide, thus confirming that unstable myosin S2 coiled coil increases the amount of contraction in the myofibril.

The in vitro motility assay confirms the effect of stability of myosin S2 coiled coil over amount of force produced through acto-myosin interaction. The MyBPC and the stabilizer peptide stabilize the myosin S2 coiled coil and the destabilizer destabilizes the myosin S2 coiled coil. Decreased sliding velocity of actin over myosin in presence of stabilizer peptide and MyBPC and increased sliding velocity of actin in presence of destabilizer peptide confirm that stable myosin S2 decreases the amount of force produced and unstable myosin S2 increase the amount of force produced through acto-myosin interaction.

All these experiments performed confirm that when the myosin S2 coiled coil is stabilized by MyBPC and the stabilizer peptide, the contraction in myofibrils and the amount of force produced by acto-myosin interaction decreases. When the myosin S2 coiled coil is destabilized by destabilizer peptide the contraction in myofibrils and the amount of force produced by acto-myosin interaction increases. Stable myosin S2 coiled coil decreases and unstable myosin S2 coiled coil increases the amount of contraction and net force produced which indirectly gives substantial support to the idea that myosin S2 stability regulates the amount of myosin S1 heads available to bind actin. Stable myosin S2 coiled coil reduces the amount of myosin S1 heads available thus reducing myofibril contraction and net force production and vice versa in case of unstable myosin S2 coiled coil.

Materials and Methods

Reagents and Tissue

Propionic acid, imidazole, and $Mg(C_2H_3O_2)_2$ were purchased from Sigma-Aldrich (St. Louis, MO). Boric Acid and KOH were purchased (EM Industries, Gibbstown, NJ). $CaCl_2$) were purchased from Avantor (Center Valley, PA). We used myofibrils previously extracted and prepared from rabbit skeletal muscle as described by Duong and Reisler (1989). Afterwards, we stored the myofibril suspension with glycerol in a 1:1 ratio at −10° C.

We created a buffer solution with 2.2 mM $Mg(C2H_3O_2)_2$, 10 mM imidazole, 130 mM propionic acid, 0.1 mM $CaCl_2$) and titrated the solution with 10 M KOH until the pH reached 7. We decided to combine these chemicals and target a pH of 7 in order to simulate regular cell conditions for the myofibrils.

Preparation of Assay Myofibril

In order to use the myofibril in a myofibrillar contractility assay, we first needed to separate the myofibrils from glycerol, which acts as a storage medium at −10° C. In addition, we wanted to separate the myofibril from extraneous cellular components.

We began by extracting 50 mg of the myofibril suspension and adding 1 mL of our buffer into a 2 mL microcentrifuge tube. Next, we centrifuged the tube three times at 5000 RPM for 5 minutes on an IEC Micromax microcentrifuge, thereby isolating the denser myofibril from the lighter glycerol and unnecessary cellular constituents. After each centrifugation, we disposed of the supernatant and filled the microcentrifuge tube to 1 mL again with our buffer. Furthermore, we used a Fisher Vortex Genie 2™ to dislodge the pellet from the bottom of the microcentrifuge tube, making the next centrifugation effective. Following the series of centrifugations, we stored the myofibrils with the buffer in a 4° C. fridge to maintain their biological function. Every 2 days, we prepared new myofibrils with the method described above because previous batches of myofibril would be subject to rigor mortis: muscle death where myofibrils are indefinitely contracted.

Myofibrillar Contractility Assays

A myofibrillar contractility assay tests the effect of certain chemical compounds on myofibril contraction. The assay involves the interaction of myofibrils with ATP, and we measured sarcomere length before and after the addition of ATP to determine percent contractility of myofibrils.

Figure 8:
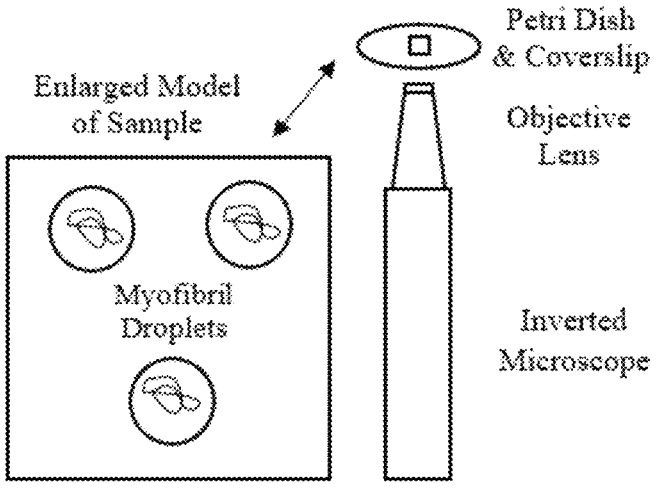
FIG. 8 schematically illustrates apparatus used that allowed precise adjusting of the field of view of a microscope, enabling efficient and quality imaging, as described in detail in Example 1, below.

We created an apparatus for myofibrillar contractility assays by attaching a coverslip to a modified petri dish using electrical tape. Each coverslip used on the apparatus can run three assays total. We placed the apparatus on a ZEISS IM35™ inverted microscope equipped with a CANON POWERSHOT A510™ connected to one of the microscope's ocular lenses. Our apparatus allowed us to precisely adjust the field of view of the microscope, enabling efficient and quality imaging (FIG. 8).

To run an assay, we first placed a 20 μL drop of our prepared myofibrils onto the coverslip. Then, we added chemical modifiers (peptides and antibodies) to each droplet as needed and used a CARL ZEISS PLAN 40/0.65 160/0.17™ objective lens to focus on the myofibrils with the microscope. Since the antibodies have a much larger molecular mass than the peptides, we determined that the antibodies would also require a longer period of time to diffuse throughout the myofibril droplet. We allowed the antibodies a minimum of 5 minutes to diffuse into the myofibril solution while we gave peptide modifiers 30 seconds to settle into the solution.

When viewing the droplet through the microscope, we searched for myofibrils that appeared uncontracted and displayed visible striations. These myofibrils would be likely to show evidence of contraction when they interacted with the ATP in the assay. We photographed the chosen myofibril before the addition of ATP. Then, we pipetted 2 μL of 18 mM ATP on the myofibril droplet, and we typically observed a visible contraction within 30 seconds. We needed to carefully watch the camera screen when adding the ATP because the addition of ATP solution onto the drop or the motion of the myofibril as it contracted would occasionally displace the myofibril. If the myofibril moved, we adjusted our field of view accordingly so that the myofibril was visible once again.

After the contraction concluded, we re-imaged the myofibril to compare the current sarcomere length with the initial sarcomere length. Using IMAGEJ™ (ImageJ), an image processing software developed by the National Institutes of Health (NIH), we measured the sarcomere lengths of myofibrils in microns through a pixels-per-micron scale in the software. We determined the percent contractility of the myofibril by measuring the percent change in the sarcomere length before and after the ATP-induced contraction.

Determining Concentration

We conducted the myofibrillar contractility assay at different concentrations for each peptide and antibody. The concentration of the unlabeled peptides and antibodies was previously determined, so we simply used the given concentration of the stock solution to calculate the dilution coefficient and dilute accordingly. On the other hand, we used an AGILENT 8453™ UV-Vis Spectrophotometer to measure the fluorophore-labeled peptides' absorbance of visible light. We recorded the absorbance and calculated the concentrations of the labeled peptides using the Beer-Lambert Law.

We realized when testing the labeled peptide that the concentration of peptide in the same microcentrifuge tube was decreasing on a day-to-day basis according to the readings of the spectrophotometer. Curious as to why this phenomenon was occurring, we did some research and consulted our mentor; we discovered that the peptides had an affinity for the inner surface of the tube. As a result, the concentration of peptide-containing solution decreased over a period of time. We decided to frequently measure the concentration of the labeled peptide to assure accurate data collection. In assays with the unlabeled peptide, we would immediately use the peptide solution following the dilution of the stock solution. By ensuring minimal time between the dilution and addition of the peptide to the myofibril droplet, the peptide would not have time to adhere to the tube.

Myosin

Myosin was extracted from rabbit skeletal muscles using the protocol from Scientist et al. Cold extraction buffer (0.3 molar (M) potassium chloride, 0.072 M sodium phosphate monobasic, 0.063 M potassium phosphate dibasic, and 0.001 M ethylene diamine tetra-acetic acid with pH 6.5) was used to extract myosin from ground rabbit skeletal back muscle. Three times the volume of ground rabbit back muscle the cold extraction buffer was added. For 15 minutes, the combination was stirred gently, followed by addition of distilled water at 4° C. to bring the volume 10 times the volume of ground rabbit muscle. Stirring was allowed for additional 20 minutes. Later the muscle slurry was filtered through the cheese cloth covered funnel in to a 28 flask. Distilled water was added to the filtered product (15× the volume) and was allowed to precipitate over night at 4° C. The clear supernatant was discarded and precipitate was centrifuged for 10 minutes in GSA rotor at 7000 rpm. To suspend the precipitate, 5 ml of 2 M potassium chloride was used. The final concentration of potassium chloride was diluted to 0.3 M with cold distilled water after measuring the volume of suspended precipitate. The next step was to precipitate the impurities, the product was centrifuged for 45 minutes to at 9000 rpm. Acquired supernatant was finally diluted to the concentration of 0.033 m potassium chloride with cold distilled water. Extinction coefficient of 0.55 $(mg/ml)^{-1}$ $cm^{-1}$ at 280 nm was used the obtain myosin concentration. Lastly, the rabbit skeletal myosin was flash frozen in liquid nitrogen and kept at −80° C. in aliquots for experimental use.

Actin

Acetone powder from the rabbit back muscle was used as described to obtain actin (Spudich & Watt, 1971). The filtered material obtained on the cheese cloth of myosin extraction was extracted and added to the two times the volume of cold buffer (0.6 M potassium chloride, 0.4 M sodium bicarbonate and 0.01 M sodium carbonate; pH=7.0). The same volume of distilled water and filtered through the cheese cloth was used to dilute the mixture. For 30 minutes at room temperature, the product was washed with 5× volume of 4% sodium bicarbonate solution and was further filtered through the cheese cloth again. For 5 minutes, the product was washed with 10× volume of distilled water and filtered again using cheese cloth. For 10 minutes, the product was washed with 3× volume of acetone and filtered through cheese cloth. Acetone was repeated two time and product acquired was dried at room temperature overnight. Acetone powder was scratch and stored at −20° C. To extract actin from the acetone powder, 5 gram of acetone powder was suspended in 30 ml of G-buffer (2 mM Tris hydrochloric acid, 0.2 mM adenosine triphosphate, 0.5 mM 2-mercapto-ethanol, and 0.2 mM calcium chloride with pH 7.6) for 120 minutes at 4° C. For 15 minutes the product was centrifuged at 15000 rpm later the supernatant was collected. 0.45 m Millipore filter was used to filter the supernatant. A final concentration of 50 mM potassium chloride and 1 mM magnesium chloride was added to the filtered supernatant to polymerize actin for 120 minutes at room temperature. Additionally, for 30 minutes, 0.6 M potassium chloride was added and stirred. For 30 minutes at 4° C. the product was centrifuged at 40,000 rpm. Pellet acquired was put in G-buffer and dialyzed against G-buffer with continuous stirring for 72 hours at 4° C. For dialysis, G-buffer was used every 24 hours. For 60 minutes, at 4° C., the dialyzed product was centrifuged at 40,000 rpm, the supernatant containing G-actin was removed. Extinction coefficient of 0.63 (mg/ml)-1 cm-1 at 290 nm was used to obtain actin concentration. G-actin was polymerized in 50 mM potassium chloride, flash frozen, and was stored in −80° C. in small aliquots for further use.

Human β-Cardiac Myosin S2 Peptide

A small region of myosin subfragment 2 (S2) region of human β-cardiac myosin (MYH7) was selected to be synthesized by BioSynthesis; Inc. The region was selected based on mutations found within this region causing Familial hypertrophic cardiomyopathy (FHC) (Richard et al., 2003). The mutations are located within proximal region of myosin S2 specifically region of 921-939 (FIG. 7). Myosin S2 is an intrinsically unstable coiled coil and the sequence of this region was acquired from Protein Data Bank (PDB). The 19 residue peptide was chemically synthesized. Generated amino acid sequence used is as follow:

Wild-type: NH2-EMNERLEDEEEMNAELTAK—COOH (SEQ ID NO:7) (E=glutamate, M=methionine, N=asparagine, R=arginine, L=leucine, D=aspartate, A=alanine, T=threonine, K=lysine)

FIG. 7 graphically illustrates a familial hypertrophic cardiomyopathy distribution hotspot on MYH7 gene, each blue box represents a HCM point mutation. Red highlights the HCM mutation studied throughout this study.

Human β-Cardiac Mutant Myosin S2 Peptide (E930Del)

Mutation hotspot region of human β-cardiac myosin S2 revealed that glutamate deletion at 930$^{th}$ residue (E930del) is one of the several point mutation that cause FHC (FIG. 7). This mutation cause mechanical instability and unstable coiled coil. Again the sequence of this mutation was obtained using PDB. An 18 residue peptide of this region was chemically synthesized. Generated amino acid sequence used is as follow:

E930del: NH2-EMNERLEDEEMNAELTAK—COOH (SEQ ID NO:8)

E=glutamate, M=methionine, N=asparagine, R=arginine, L=leucine, D=aspartate, A=alanine, T=threonine, K=lysine Human β-Cardiac Mutant Myosin S2 Peptide (E924K)

Mutation hotspot region of human β-cardiac myosin S2 revealed that glutamate substitution to lysine at 924$^{th}$ residue (E924K) is one of the several point mutation that cause FHC (FIG. 7). This mutation also causes mechanical instability and unstable coiled coil. Sequence of this mutation was obtained using PDB. A 19 residue peptide of this region was chemically synthesized. Generated amino acid sequence used is as follow:

E924K: NH2-EMNKRLEDEEEMNAELTAK—COOH (SEQ ID NO:9)

E=glutamate, M=methionine, N=asparagine, R=arginine, L=leucine, D=aspartate, A=alanine, T=threonine, K=lysine Human Skeletal Myosin S2 Peptide MYH2 gene codes for human skeletal muscle myosin expressed in fast type IIA muscle fibers. This myosin isoform can be found within extraocular muscle. A 19 residue peptide of the S2 region of MYH2 was matched to the previously synthesized S2 peptide of cardiac isoform and chemically synthesized residues 925 to 945. Generated amino acid sequence used is as follow: residues 925 to 945

Skeletal: NH2-EVTERAEDEEEINAELTAK—COOH (SEQ ID NO:10)

E=glutamate, V=Valine, N=asparagine, R=arginine, L=leucine, D=aspartate, A=alanine, T=threonine, K=lysine, I=Isoleucine Human Smooth Myosin S2 Peptide Human smooth muscle myosin heavy chain (MYH11) is a part of the non-striated muscle. This gene can be found within esophagus, endometrium, duodenum, etc. A 21 residue peptide of the S2 region of MYH11 was matched to the previously synthesized S2 peptide of cardiac isoform and chemically synthesized 926-946. Generated amino acid sequence used is as follow:

Smooth: NH2-EMEARLEEEEDRGQQLQAERK—COOH (SEQ ID NO:11)

Figure 9:
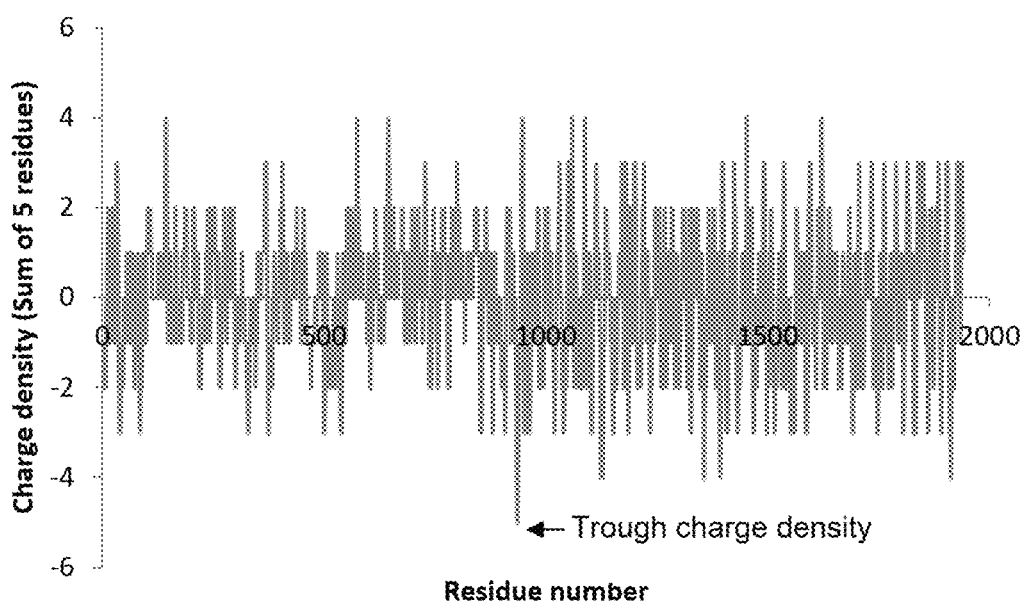
FIG. 9 illustrates plots of the charge distribution along primary sequence of MYH7 beta-cardiac myosin sequence demonstrating a trough at the location where the stabilizer peptide is designed to bind, as described in detail in Example 1, below.

E=glutamate, M=methionine, A=alanine, R=arginine, L=leucine, D=aspartate, G=Glycine, Q=Glutamine, K=lysine Stabilizer Peptide Stabilizer peptide is a poly-cation compound that was designed computationally to bind around cardiac muscle myosin (S2) region of 921-939. This specific region of myosin S2 is rich in glutamate. Thus the positive charge from stabilizer peptide and negative charge from myosin S2 peptide would allow for protein-protein interaction (FIG. 9). FIG. 9 plots the charge distribution along primary sequence of MYH7 beta-cardiac myosin sequence demonstrating a trough at the location where the stabilizer peptide is designed to bind.

Figure 10:
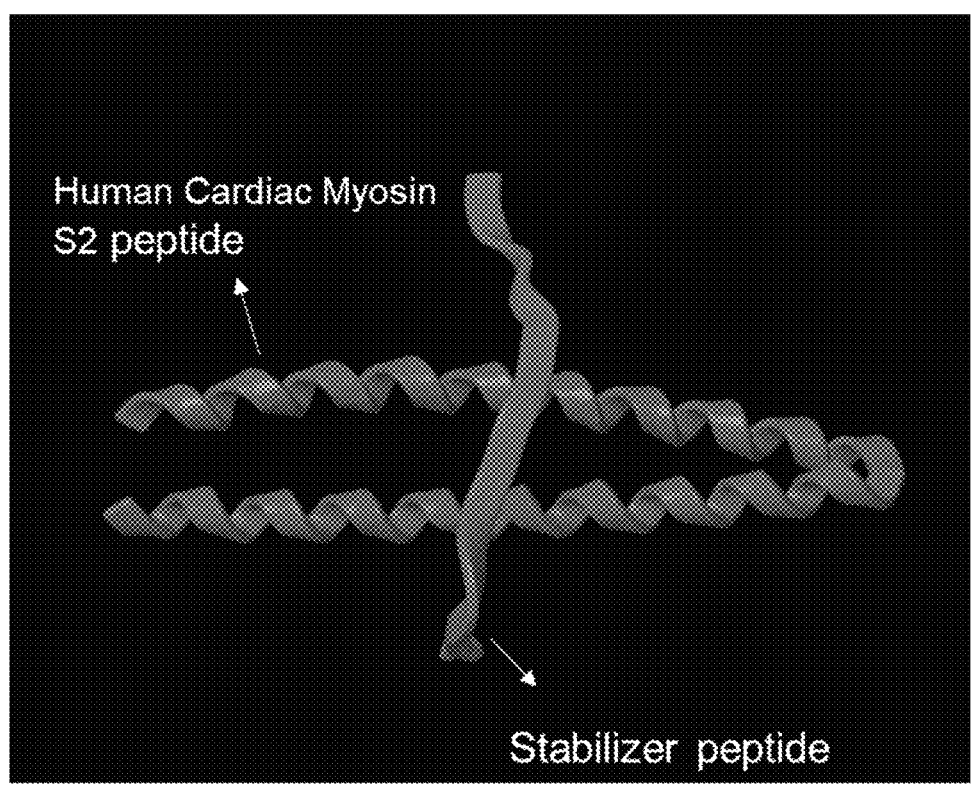
FIG. 10 illustrates an image of a molecular model generated from computer simulation illustrating a molecular representation of stabilizer peptide (red) bound around cardiac myosin S2 peptide (purple), as described in detail in Example 1, below.

A molecular model generated from computer simulation of a MACROMODEL™ (Schrödinger, Inc.) program is shown below (FIG. 10).

FIG. 10 schematically illustrates a molecular representation of stabilizer peptide (red) bound around cardiac myosin S2 peptide (purple).

Destabilizer Peptide

Destabilizer peptide is a 19 residue peptide against human cardiac muscle myosin S2 region of 921-939. This peptide has high binding affinity to a single helix of the myosin S2. One molecule of this destabilizer peptide would bind to one alpha helix of cardiac muscle myosin S2 coiled coil and disrupts the natural coiled coil formation. Molecular model representation is shown below (FIG. 11).

Figure 11:
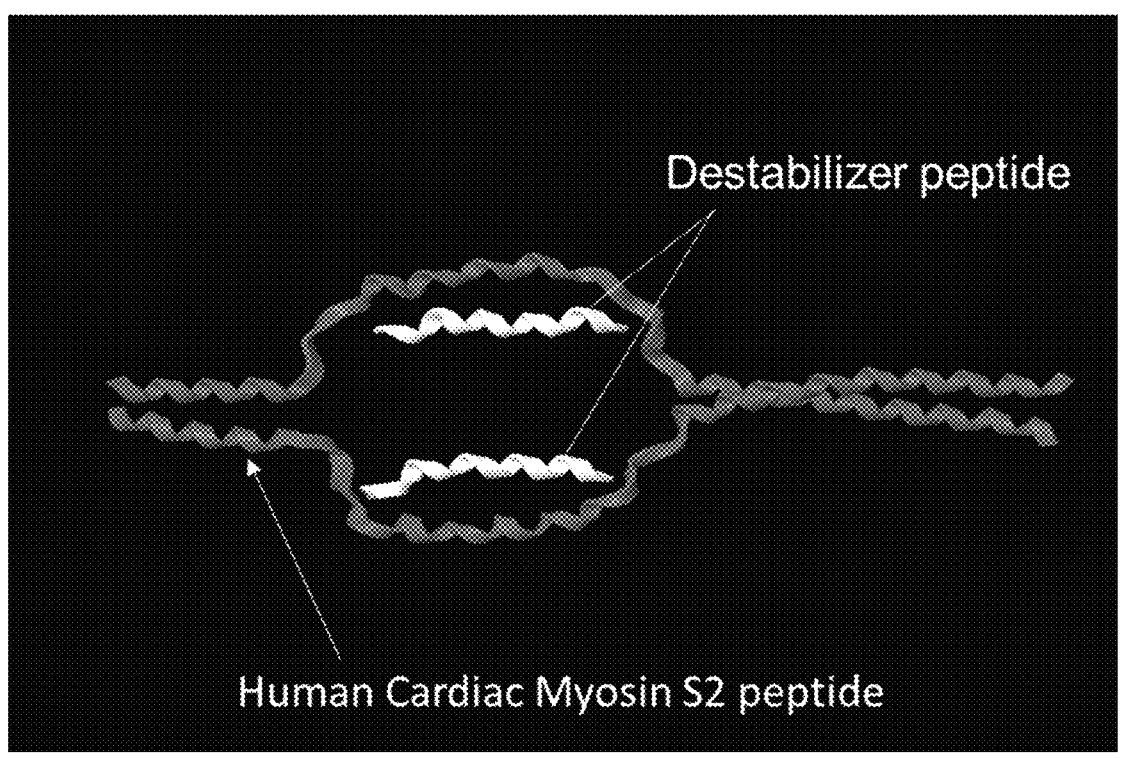
FIG. 11 illustrates an image of a molecular model representation of a destabilizer peptide (white) pulling human cardiac myosin S2 peptide dimer (red) apart, as described in detail in Example 1, below.

FIG. 11 schematically illustrates a molecular representation of destabilizer peptide (white) pulling human cardiac myosin S2 peptide dimer (red) apart.

Fluorescence Resonance Energy Transfer Acceptor and Donor Probes

Chelate-lanthanide complex was utilized as the donor probe, which is composed of a lanthanide, an antenna, and a chelate. Organic chromophore antenna (cytosine) will absorb a photon of light, and it will transfer energy to lanthanide ion (terbium III). This probe excites at 248 nm and emits at 547 nm.

Fluorescein was used as the acceptor probe. Fluorescein isothiocyanate (FITC) is composed of a xanthene ring and a reactive thiol group. Xanthene ring has fluorescent characteristics and the reactive thiol group will bind to the biomolecules at their free amino (—NH$_2$)group. This probe has excitation peak at 495 nm and emits at 520 nm.

Resonance energy probes (donor and acceptor) were covalently attached to synthetic myosin S2 peptides of cardiac muscle, E930del cardiac muscle, E924K cardiac muscle, smooth muscle, and skeletal muscle (Aboonasrshiraz, N., 2020).

Figure 12:
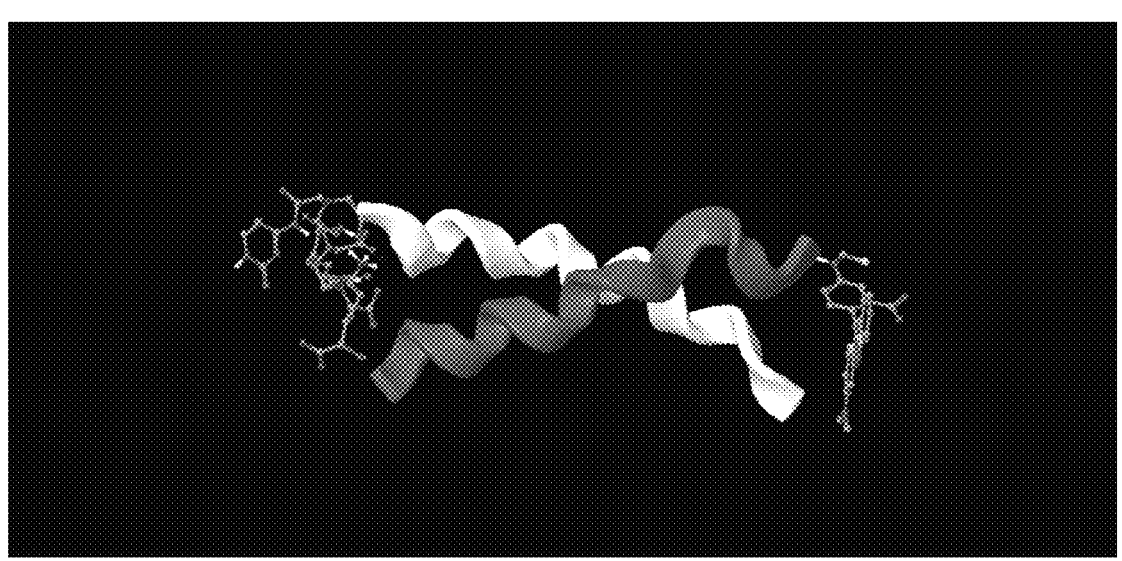
FIG. 12 illustrates an image of a molecular model representation of amino acid sequences of muscle peptides attached to resonance energy transfer probes that were selected through dynamic simulation experiments, as described in detail in Example 1, below.

Amino acid sequences of muscle peptides were attached to the resonance energy transfer probes that were selected through dynamic simulation experiments (FIG. 12). The same method was used to conjugate probes to mutant peptides (E924K and E930del). Muscle myosin S2 peptide synthetic peptide sequences are as follow:

```
Wild-type
                            (SEQ ID NO: 7)
NH2-EMNERLEDEEEMNAELTAK-COOH

E924K
                            (SEQ ID NO: 8)
NH2-EMNKRLEDEEEMNAELTAK-COOH

E930del
                            (SEQ ID NO: 9)
NH2-EMNERLEDEEMNAELTAK-COOH

Skeletal
                            (SEQ ID NO: 10)
NH2-EVTERAEDEEEINAELTAK-COOH Smooth
                            (SEQ ID NO: 11)
NH2-EMEARLEEEEDRGQQLQAERK-COOH
```

Acceptor probe was conjugated to muscle myosin S2 peptides at N-terminus. Muscle myosin S2 peptides were dissolved in 20 mM HEPES buffer at pH 8.0. And FITC was dissolved in few drops of N, N dimethyl formamide. Lastly, FITC and muscle myosin S2 peptide was reacted together in 1 to 1 molar ratio and was let to react for 120 minutes at room temperature. The FITC conjugated S2 peptides were purified using (write a sentence about the chromatography).

Donor probe was conjugated to muscle myosin S2 peptides at the C-terminus. Chelate was attached to a reactive site of cytosine and muscle myosin S2 peptide was attached to another reactive site of cytosine in dimethylsulfoxide (DMSO) as a solvent at room temperature (Aboonasrshiraz, N., 2020). Chelate and cytosine were reacted together in 1 to 1 molar ratio. Later, muscle myosin S2 peptide was reacted with chelate-cytosine mixture in 1 to 1 molar ratio conjugating to primary amine group of lysine. For lanthanide, terbium ion with a longer life-time was used. Titration of terbium ion to chelate labeled peptide was done in 1 to 1 ratio prior to FRET assay.

FIG. 12 schematically illustrates an atomic model of myosin S2 peptide where FTIC conjugated to one monomer (red) and terbium chelate complexed conjugated to another monomer (white).

Florescence Resonance Energy Transfer

Instrumentation

In this experiment, luminescence spectrometer, AMNICO-BOWMAN SERIES 2 SPECTROMETER™, was used to detect resonance energy transfer. This instrument is composed of two light sources: continuous lamp and flash lamp (UV excitation source) and sensitive detectors for time-resolved detection. Specific experimental settings will be controlled through a connected computer system to the instrument. The connected computer system also enables data storage. Built in gates and filters for further control and monitoring will control intensity of light that will pulse through and emit from the sample. Emission signal generated from decay of molecules was detected by a photomultiplier tube, which contains proper color filters to detect the emitted photons.

Monochromators

Emission and excitation lights require wavelength and bandpass values. These values were selected using monochromators. Diffraction gratings, mirrors, and slits make up monochromators. Monochromators allowed continuous ranges of an untainted narrow band of excitation and emission light. Monochromators measured fast multiple wavelengths. This was possible with a fast-slewing monochromators that is 12,000 nm per minute, and a bandpass that is controlled through a computer.

Bandpass

Bandpass is the width of the slit that has a huge impact on intensity and resolution of light, which merges together. Bandpass was used to bring balance between intensity and resolution. It is usually between 0.5 to 16 nanometers. Opening of the bandpass causes more light to pass to the sample, thus an increase in sensitivity.

Photomultiplier Tube (PMT)

Luminescence spectrometer is connected to a computer system to collect the data during the experiment. Light from the sample emerges, goes to the emission monochromator, and then into the PMT. The emitted photons energized the photocathode of the PMT and converts the energy to an amplified DC current. Computer measured an amplified DC current as fluorescent intensity. PMT can be gated to accommodate different wavelengths of light.

The alternative set up will be used as well. In this set up, there is an external PMT placed closer to the light that comes out from the sample to avoid light expansion and loss of more light. Instead of emission monochromator, we will have filters to select the wavelength.

Proximity of collecting light into external PMT is higher compared to internal PMT, which is further away from the sample and there is the possibility of losing light. This alternative set up is hooked on to an amplifier and sensitivity is controlled. The emission output goes through an amplifier, which is converted to voltage. The data is stored in digital oscilloscope and used for further calculations and analysis.

Fast Protein Liquid Chromatography (FPLC)

Fast protein liquid chromatography is a common technique to purify and separate protein mixtures. FPLC has two main phases: stationary and a mobile. Beads with pores or conjugated with adjuvant to trap the proteins make up the stationary phase, and any buffer that flows through stationary phase is considered mobile phase. Stationary phase consists of resin beads where the protein of interest binds to with the help of buffer promoting this binding. While the mobile phase is the buffer will dissociate the bound protein of the beads based on the decreasing affinity of protein to the beads. A FPLC contains one or two pumps, computer system, detection units, and a fraction collector. The pumps within the FPLC run the buffers through stationary phase or the resin beads. UV absorbance and conductivity of the protein mixtures are measured using UV and conductivity detectors attached to the end of the column as sample elutes from the column. Computer system allows modification of methods, manage ongoing run, and collect and evaluate chromatograms (Robyt and White, 1987).

Reverse Phase Chromatography (RPC)

Reacted and unreacted FITC-conjugated peptide was separated from each other using a pepRPC column of reverse phase chromatography. Binding of FITC-conjugated peptide to the column was increased using Trifluoroacetic acid (TFA). The TFA enhances the ion paring of FITC-conjugated peptide to the column. There were two buffers used: Buffer A containing 0.05% TFA in water to promote the ion-pairing of FITC-conjugated peptide to pepRPC column. While buffer B containing 0.05% TFA in acetonitrile with gradient of 0% to 100% allowed to elute the FITC-conjugated peptide of the column. The flow rate of buffers through the column was maintained at 0.5 mL/minute.

Collected fractions from the pepRPC column run were purified further to remove TFA. To remove TFA from the fractions, divilobenzene (DVB) column was used. Buffers used during DVB column purification was water as buffer A and methanol as buffer B with gradient set to 0% to 100% to elute the FITC-conjugated peptide After collecting the fractions, methanol was evaporated with help of centrifuge and the sample was later dissolved in appropriate assay buffer of choice.

Methodology

Reverse Phase Chromatography like any other chromatographies consists of two phases: nonpolar stationary and polar mobile. This column elutes protein mixture based on its increasing hydrophobicity. Therefore, polar proteins elute before nonpolar proteins do. Computer system allows setting the gradient from 0% to 100% of the nonpolar solvent for elution to take place. To increase ion-paring of protein mixtures to the column trifluoroacetic acid (TFA) was used. TFA is used to increase binding of protein mixture to the nonpolar stationary phase by allowing the hydrophobic interaction between stationary phase and the protein mixture. Long narrow column with greater number of theoretical plates can be used to improve separation of protein mixture. In addition, acidic conditions improve with high resolution. However, acidic conditions and environments only work for short peptides and if used with nucleic acids or proteins they undergo denaturation. Backpressure that is the result of protein mixture and column interaction is a main issue associated with RPC. Performing RPC at a very low flow rate would decreases the chances of facing backpressure. However, a very slow flow rate would decrease the resolution due diffusion along the column (Amersham Pharmacia Biotech AB., 2001).

Anion-Exchange Chromatography

Reacted and unreacted chelate-conjugated peptide were separated from each other using Q-Sepharose column of anion exchange chromatography. There were two buffers used: Buffer A contained 10 mM imidazole at pH 7 and Buffer B contained 10 mM imidazole and 1 M KCL at pH with flow rate of 1 mL/minute with 0% to 100% gradient.

Methodology

Anion—exchange chromatography allows protein mixture separation based on molecular charge. This type of chromatography attracts anions that are negatively charged to the stationary phase comprised of positively charged beads. This technique works based on attraction between analyte and stationary phase. Stationary phase and oppositely charged analyte bind together and mobile phase alters the binding of analyte to the column with charged ions (salt). There should be at least one pH unit difference between eluent buffer and analytes isoionic point (Principles and techniques of Biochemistry and Molecular Biology). The right type of buffer allows maximum number of impurities to stay on the column or elute last. Net surface charges of interested compound plays a big role on media selection. Protein mixture binds to the matrix. Alterable interaction of charged molecule with oppositely charged column matrix separates the protein mixture. Increase in salt concentration of mobile phase, alters ionic strength within the column, results in compound elution. Salt ions race with bound biomolecules to binding to the matrix leading to elution of protein from the column based on the molecular charge (Amersham Pharmacia Biotech AB., 2001).

Spectroscopy and Chromatograms

Figure 13:
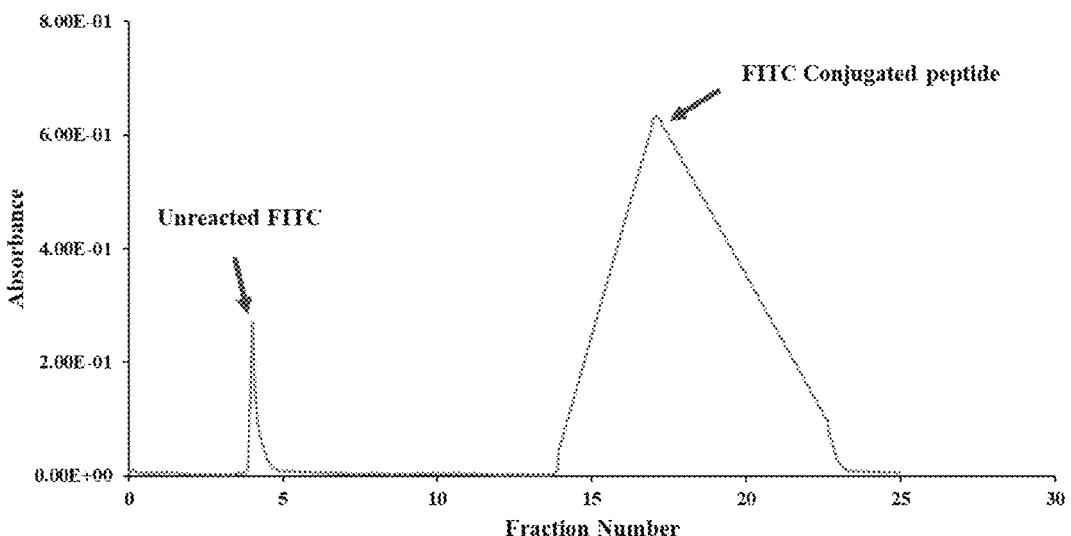
FIG. 13 graphically illustrates that absorbance readings of FITC conjugated peptide fractions had two main chromatographic elution peaks; this is an example of absorbance spectrometer reading of fractions from the pepRPC column, as described in detail in Example 1, below.

UV-vis spectrometer was used throughout the experiments to measure the concentration of compounds based on the absorbance of a respective wavelength of light. A spectrometer (Hewlett-Packard) was used to obtain concentration of the peptides conjugated to the acceptor or donor probe from FRET. FITC conjugated peptide had an absorbance peak at 495 nm. The absorbance readings of FITC conjugated peptide fractions had two main chromatographic elution peaks (FIG. 13, graphically illustrating an example of absorbance spectrometer reading of fractions from the pepRPC column). The first peak signifies the unreacted FITC and the second peak signifies FITC conjugated peptide. Beer-Lambert's law was used find out the concentration of FITC conjugated peptide. In Beer-Lambert's law, "A=$\alpha$ C l", A is absorbance read by spectrometer at 495 nm, $\alpha$ is the extension coefficient which is 5900 $M^{-1}$ $cm^{-1}$ for FITC and I distance that light travel through the sample which is 1 cm.

Figures 14, 15:
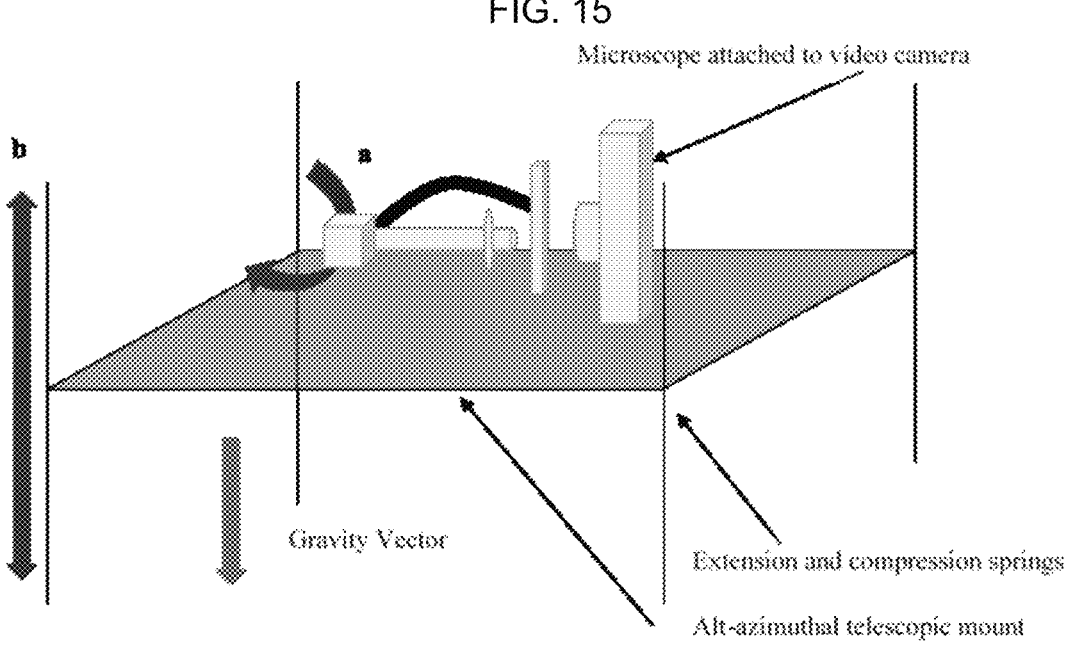
FIG. 14 graphically illustrates that the absorbance reading of peptide-conjugated chelate complex had four main elution peaks in the chromatograph of the Q Sepharose column, as described in detail in Example 1, below.
FIG. 15 is a schematic diagram of a gravitational force spectrometer (GFS) which has two modes, where this illustration shows the free-fall mode, as described in detail in Example 1, below.

Chelate complex conjugated peptide had an absorbance peak at 290 nm. The absorbance reading of peptide conjugated chelate complex had four main elution peaks in the chromatograph of the Q Sepharose column in FIG. 14. The first peak corresponds to unreacted cytosine, the second and third peaks correspond to unreacted DTPA and unreacted DTPA with cytosine, and the last peak corresponds to chelate complex conjugated peptide. Concentration of chelate complex conjugated peptide was measured using the same Beer-Lambert's law with $\alpha$=9300 $M^{-1}cm^{-1}$ and l of 1 cm.

Gravitational Force Spectroscopy

Materials 3-aminopropyltriethoxysilane, acetone, coupling buffer (0.01 M pyridine in water with pH 6.0), 5% glutaraldehyde, quenching solution (1 M glycine in water with pH 7.0), blocking buffer (0.01 M Tris, 0.1% sodium azide, 0.1% bovine serum albumin, 0.15 M sodium chloride, and 0.001 M ethylenediaminetetraacetic acid with pH 7.0), wash buffer (0.01 M Tris, 0.1% sodium azide, 0.15 M sodium chloride, and 0.001 M ethylenediaminetetraacetic acid with pH 7.0) low salt buffer (0.1 M potassium chloride, 0.02 M imidazole, 5 mM magnesium chloride, with pH 7.0), 1-ethyl-3-(3-dimethyaminopropyl) carbodiimide, N-hydroxysuccinamide, iodoacetamide-succinimidyl ester, 8M urea solution (50 mM imidazole and 0.1 mM tris (2-carboxyethyl) phosphine with pH 7.0) monodisperse silica beads, glass slides, glass coverslips, vacuum grease, rabbit skeletal myosin, purified actin (G-actin), 1 μM human β-cardiac myosin S2 peptide, 1 μM human β-cardiac mutants myosin S2 peptide (E930del and E924K), 1 μM human skeletal myosin S2 peptide, 1 μM human smooth myosin S2 peptide, stabilizer peptide, and destabilizer peptide. A light microscope with an objective lens of 10× was mounted on an alt-azimuthal mount. A digital video camera of Sony, XCD-V60 was replaced with the ocular lenses. Extension springs on steel bracket held the alt-azimuthal mount suspended.

The muscle myosin S2 synthetic peptides were as follow:

```
                                         (SEQ ID NO: 12)
KIQLEAKVKEMNERLEDEEEMNAELTAKKRKLEDEC  (MYH7)

(SEQ ID NO: 13)
KIQLEAKVKEMNERLEDEEMNAELTAKKRKLEDEC  (MYH7 E930del)

(SEQ ID NO: 14)
KQELEEILHEMEARLEEEEDRGQQLQAERKKMAQQC  (MYH11)

(SEQ ID NO: 15)
KIQLEAKIKEVTERAEDEEEINAELTAKKRKLEDEC  (MYH2)
```

Methodology

Gravitational force spectroscopy (GFS), is a single molecule force spectroscopy that utilizes gravitational force to measure absolute length of a single molecule at the given force calculated by the density of the bead suspending the molecule. This technique was discovered and developed in Root lab, which measures the forces in piconewton and sub-piconewton levels. Other than absolute length of a molecule, GFS measures force range required to uncoil, stretch or extend the molecule yielding a force-distance profile for the suspended molecule. Besides that, based on the force-distance profile, number of amino acids within the molecule can be calculated. Also the other advantage of GFS was that it did not require any prior force calibration step up (Dunn & Root, 2011). Hence, GFS was an ideal choice to test the mechanical stability of all the myosin S2 coiled-coil. The GFS allowed to test the flexibility or stability of a single molecule of myosin S2 peptide and also for the S2 peptides treated with anti-S2 peptides. Flexibility of myosin S2 is not dependent on assembly myosin as a thick filament or myosin in its single molecule form. The flexibility of myosin S2 region was reported to be similar in single molecule form or myosin in a thick filament assembly thus it could be conceived that the changes seen on flexibility of myosin S2 in presence of anti-S2 peptides would correlate to changes in myosin S2 flexibility for myosin in a thick filament form (Singh et al., 2018). The schematic diagram of GFS is shown below (schematic diagrams of GFS which has two modes: (FIG. 15) free-fall mode, (FIG. 16) rotational mode.

GFS set up assembly contains a light microscope that is horizontally mounted on an alt-azimuthal which is suspended with help of extension springs on a steel bracket. To capture both images and videos of suspended molecule, a digital video camera has been placed instead of the ocular lenses. The molecule of interest is tethered between an immobile edge of glass coverslip placed on a glass slide and mobile silica or glass bead. Slide with the molecule of interest in inserted into the light microscope component of GFS. The bead with molecule of interest is imaged through the microscope and then oriented to the direction of gravity vector to allow the maximal gravitation force exerted on to the bead. GFS has two modes, one is called rotational mode or an equilibrium mode which measures the absolute length of a single molecule and the second one is called free fall mode which measures the force required to unwind, uncoil, stretch or extend the molecule of interest.

Rotational Mode

Figure 16:
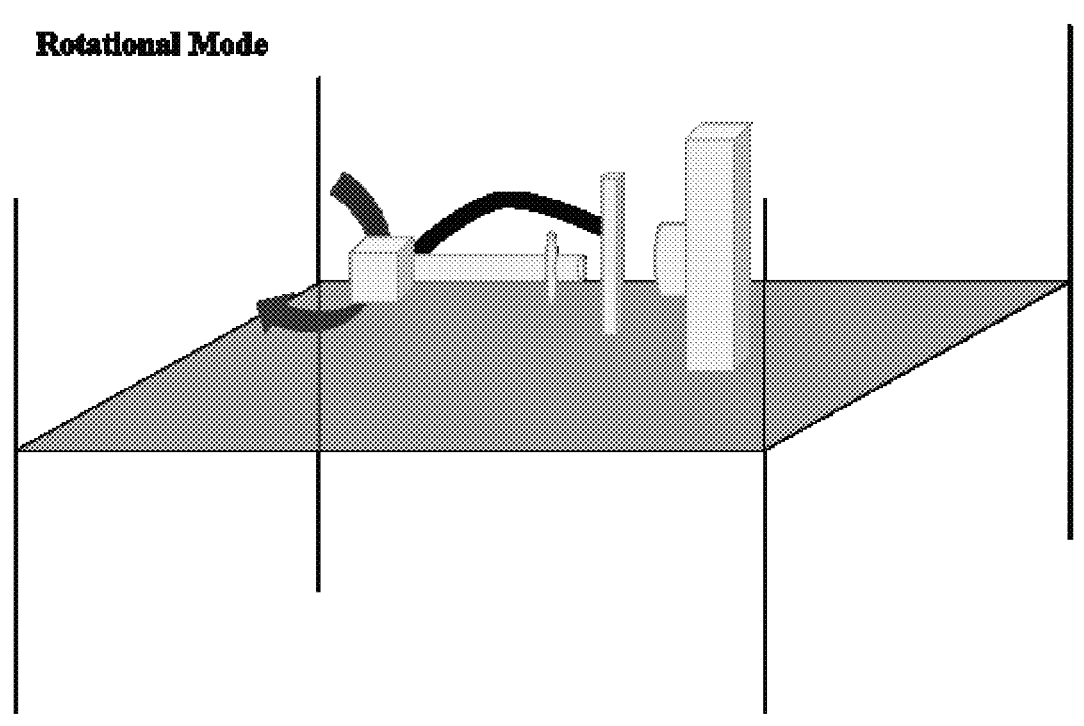
FIG. 16 is a schematic diagram of a GFS which has two modes, where this illustration shows the rotational mode, as described in detail in Example 1, below.
Figure 17:
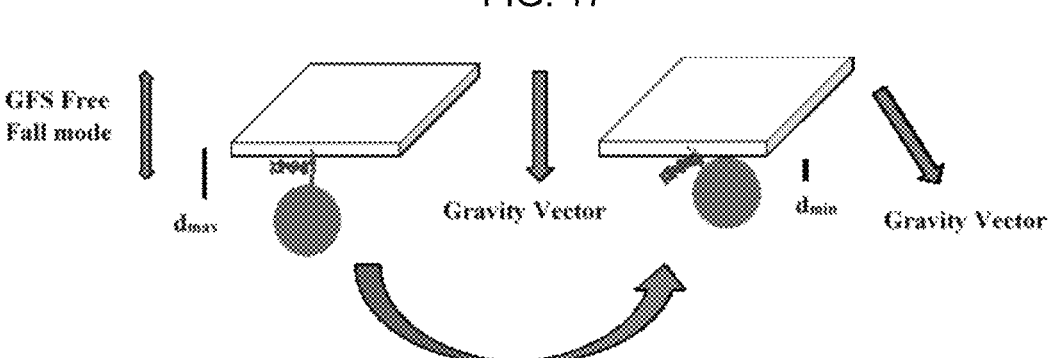
FIG. 17 illustrates a schematic diagram of rotational mode bound to immobile edge. In rotational mode, the molecule is suspended within mobile and immobile edge on a glass slide and placed on the light microscope; the bead with molecule of interest is tethered to immobile edge and oriented in the direction of gravity vector, as described in detail in Example 1, below.

Length of molecule suspended between an immobile edge and mobile bead is measured using rotational mode; FIG. 16, a schematic diagram of rotational mode setup. Red arrow indicates rotation of microscope; FIG. 17, a schematic diagram of rotational mode bound to immobile edge. In rotational mode, the molecule is suspended within mobile and immobile edge on a glass slide and placed on the light microscope. The bead with molecule of interest is tethered to immobile edge and oriented in the direction of gravity vector. To begin the measurement, orientation of the slide was rotated to 45 degrees clockwise or counterclockwise from starting position (gravity vector). After positioning the start point, 45 degrees clockwise or counterclockwise, rotation of microscope began in opposite direction, counterclockwise or clockwise.

Figure 18:
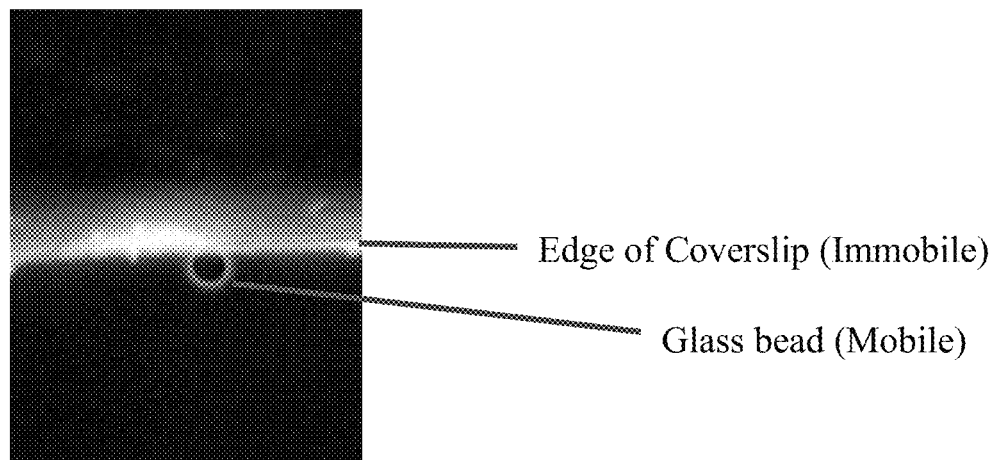
FIG. 18 illustrates an image of a mobile bead bound to an immobile edge of a microscope coverslip, as described in detail in Example 1, below.
Figure 19:
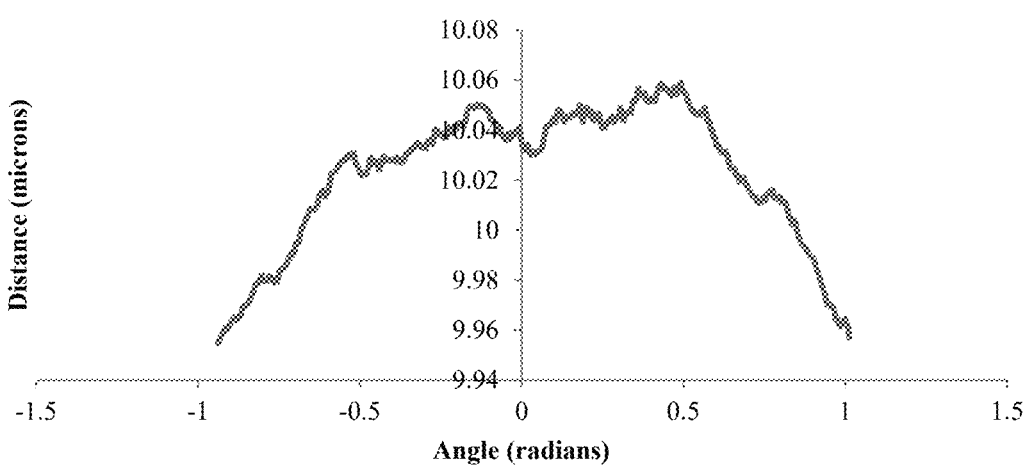
FIG. 19 graphically illustrates an example of a bell shaped curve used to get coordinates for the center of a bead, where the length of the molecule suspended by the bead is measured based on maximum and minimum length of the curve, as described in detail in Example 1, below.

Rotation was stopped when microscope rotated 90 degrees from the starting point, either counterclockwise or clockwise. For example, if the start point was set in a direction 45 degrees clockwise to the gravity vector, rotation was stopped 45 degrees counterclockwise to the gravity vector. Duration of the rotation was recorded using the mounted video camera and was later analyzed using Image J. Image J is an image processing software for analyzing images and videos. The speed at which the microscope was rotated for measurement purposes was half a degree per second. By analyzing the video an x and y coordinate was measured for each frame of the video; which is the coordinate for the center of bead. Later, this coordinates are further used to determine the length of the molecule suspended by the bead (FIG. 18, an example of mobile bead bound to immobile edge) (FIG. 19, graphically illustrating an example of bell shaped curve used to get coordinates for the center of the bead. Length of the molecule suspended by the bead is measured based on maximum and minimum length of the curve.).

The exact length of suspended molecule is obtained from analyzing a line equation parallel to the immobile edge and the center of the mobile bead for each video frame. A bell shaped curve is acquired from the distance between the mobile bead and the line plotted versus rotational angel. At the start of the rotation, the molecule has a conformation with minimum length ($d_{min}$) and during rotation when the mobile bead is parallel to gravity vector the length would be at maximum ($d_{max}$) and lastly the length would go back to minimum position again. To get the absolute length of the molecule, $d_{min}$ was subtracted from $d_{max}$. The force exerted on the bead was calculated by the product of mass of the bead and acceleration by gravity where mass of bead was rectified for its buoyancy. Mass of the bead was calculated as follows, radius of the bead was used to calculate the volume of the bead, later the volume was multiplied with the known density of the bead leaving us with the mass of the bead.

Free-Fall Mode

Free fall mode, another measurement variant of GFS which allows the user to get a force distance profile on a single molecule experiencing the gravitational force. Free fall mode allows a variable force by the virtue of gravity to be exerted on a single molecule. The GFS setup, light microscope with mounted camera on spring on alt-azimuthal platform, can be dropped. The start of free-fall mode force applied to the bead is zero or close to zero. The platform dropped during free fall mode experiences an acceleration due to gravity which results in an acceleration trace for GFS, which is the function of spring constant possessed by the spring holding the GFS platform. As the platform goes towards equilibrium, trace of the acceleration decays. During the free fall mode, GFS has a single molecule which is suspended within an immobile edge and mobile bead will now experience the variable force which would be calculated by the product of mass of the bead and the acceleration of the GFS.

Measurement in free fall mode begins with setting orientation of the bead molecule in the direction of gravity vector and then simultaneously dropping the platform while starting the video recording of bead. Recording was stopped as the platform reached steadiness. The video frames were later processed using Image J to get the x and y coordinates of the center of the mobile bead and stationary spot on the immobile edge. Rotational mode data and free fall data work hand in hand. Using the information from both assays, the length of the molecule for every single frame was calculated; later, these information yielded to force-distance graph which distance is indication of the length of the actual molecule.

The product of the GFS acceleration and the mass of the bead will provide a force trace for the single molecule tethered between the immobile edge and mobile bead. The image processing would provide distance trace for the single molecule experiencing the free fall by the GFS. When this force trace is aligned with distance trace will yield the extension or the stretch experience by the single molecule under variable forces. In this case, a coiled coil myosin S2 peptide will have one end of the monomer trapped by immobile edge and the other monomer is tethered to mobile bead. The myosin S2 molecule undergoing the free fall mode will result in a force distance trace giving the information about amount of force required to uncoil the dimer along its length. Stability and flexibility of myosin S2 peptide coiled coil can be measured by measuring the amount of force required to uncoil the coiled coil. A stable coiled coil would require greater force compared to a much more flexible coiled coil to unwind.

To test stability and flexibility of myosin S2 peptide two different types of conjugation was performed to tether the molecule between the immobile edge and mobile edge. First conjugation was crosslinking the muscle myosin S2 peptides to immobile edge and mobile bead. A different conjugation was benefiting from the binding property of actin to myosin S1. Rabbit skeletal myosin molecule at myosin S1 position was bound with G-actin treated immobile edge and mobile bead.

Conjugation with Myosin S2 Peptides

To bind the muscle myosin S2 peptide between immobile edge and mobile bead, both this edge and the mobile bead have to be treated with muscle myosin S2 peptide. Glass coverslips represent the immobile edge and silica beads represent the mobile bead. Both the glass coverslips and silica beads are treated with 0.04% 3 aminopropyltriethoxylsilane in acetone to add aminosilane groups to hydroxyl groups on the surface of both the glass coverslips and silica beads. Both glass coverslip and aminosilanate beads were rinsed with distilled water. To the aminosilane groups, 1 mg/1 ml iodoacetamide-succinimidyl ester was added; this chemical is a biofunctional crosslinker. The surfaces were rinsed with the wash buffer. 1 μM interested muscle myosin S2 peptide was added to both the surfaces in 8 M urea solution (50 mM imidazole and 0.1 mM TCPE with pH 7.0) in separate tubes. The mixture was kept in urea solution to allow muscle myosin S2 in its monomer status. Low salt buffer was exchanged with the urea solution in the slide chamber so the monomers could form a dimer molecule ready for measurement.

Conjugation of G-Actin

This conjugation was done by first, treating glass coverslips and silica beads with 0.04% 3-aminopropyltriethoxylsilane in acetone to add the aminosilane groups to both glass coverslips and silica beads. To cross link G-actin to the aminosilanated glass coverslips and silica beads 740 mM 1-ethyl-3-(3 dimethyaminopropyl) carbodiimide was used with help of 60 μM N-hydroxysuccinamide. To block any unreacted group, glycine quenching solution was added.

Lastly, both glass coverslips and silica beads went over several washes with low salt buffer and were stored in the same low salt buffer for GFS experiments.

Figure 20:
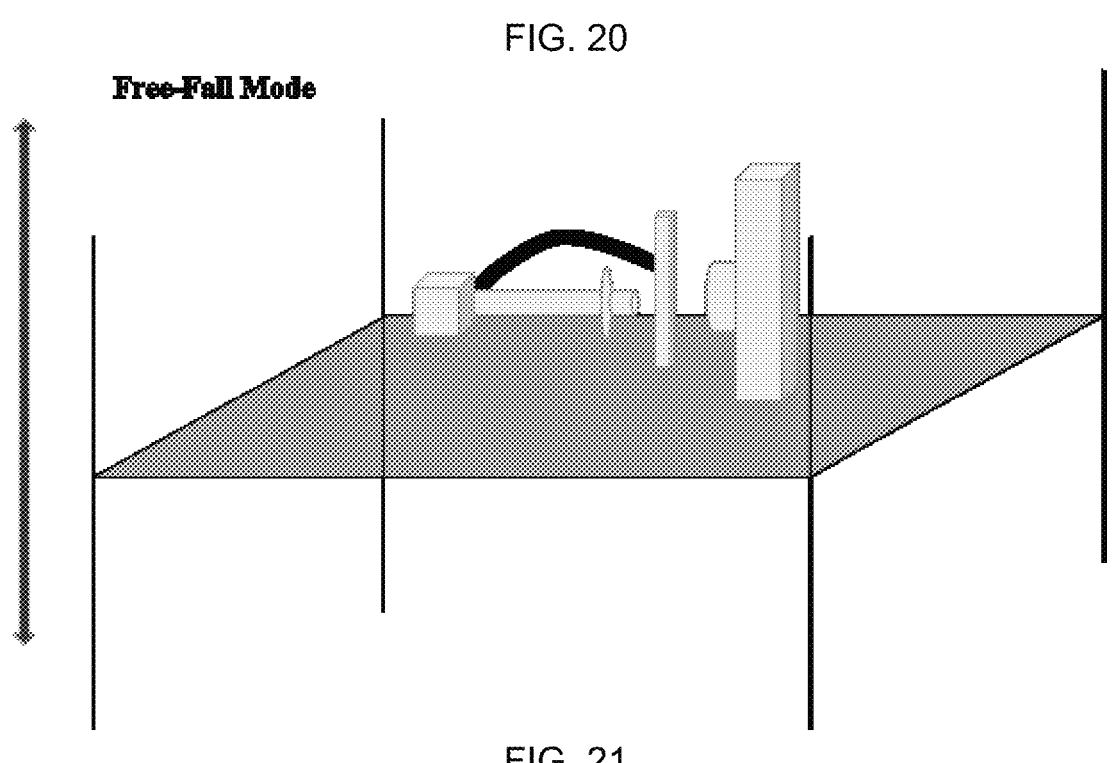
FIG. 20 a schematic illustration of a free-fall mode (red arrow), where a platform surface is dropped in direction of gravity vector, as described in detail in Example 1, below.

FIG. 20 is a schematic illustration of free-fall mode (red arrow). Platform surface is dropped in direction of gravity vector.

Oscillation of the dropped platform was matched to the gravitational acceleration experienced by the GFS platform to yield force acceleration trace using the formula bellow:

$$X(t) = a\, e^{-(\gamma t)/2}\cos(wt - Q)$$

Where Q is the phase, w is oscillation frequency, a is a proportionality constant, and $\gamma$ is damping constant.

If Q is set to zero $$X(t) = a\, e^{(\gamma/2)t}\cos t\, w\, t$$

$$\gamma(t) = -\gamma/2a\, e^{-(\gamma/2)t}\cos t\, w\, t - w\, a\, e^{-(\gamma/2)t}\sin w\, t$$

$$A(t) = (\gamma/2)^2\, a^{-(\gamma/2)t}\cos t\, w\, t + \gamma/2a\, e^{-(\gamma/2)t}\sin w\, t + w\, a(\gamma/2)\, e^{-(\gamma/2)t}\sin w\, t - w^2 a\, e^{-(\gamma/2)t}\cos t\, w\, t$$

$$A(t) = ((\gamma/2)^2 - w^2)a\, e^{-(\gamma/2)t}\cos t\, w\, t + (1+w)a\gamma/2\, e^{-(\gamma/2)t}\sin g\, w\, t$$

If $\gamma \cong 0$ $$A(t) = -w^2 a\, \cos t(w\, t)$$

And $X(t) = a\, \cos t(w\, t)$

Slide Preparation

Figure 21:
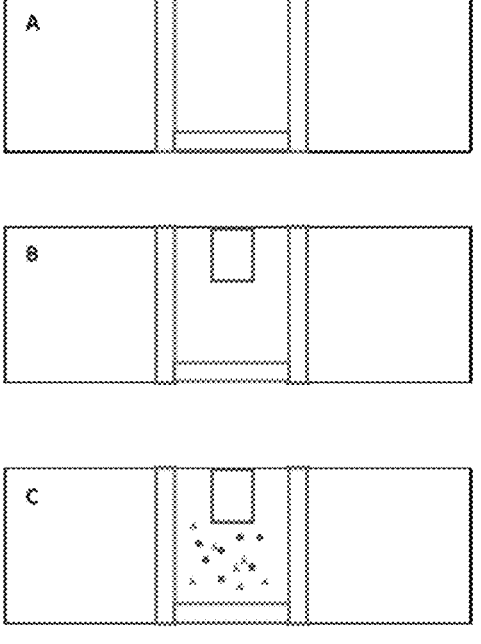
FIG. 21A-D are schematic illustrations of slide preparations for GFS measurements.

FIG. 21 is a schematic illustration of slide preparation for GFS measurements. GFS experimental slide was prepared by first selecting a clean glass slide and making a four walled chamber with edges of coverslip and vacuum grease. (FIG. 21A). One side of the chamber being the glass coverslip treated with G-actin or the interested muscle myosin S2 peptide. Second, peptide treated or G-actin treated coverslip was placed in the chamber, facing the center of the slide with vacuum grease (FIG. 21B). Third, within the chamber, around 50 μL of anticipated myosin S2 peptide or actin coated silica beads was added followed by 100 μL low salt buffer, and 5 μL anti-S2 peptide (FIG. 21C). Lastly, the chamber was sealed with another clean coverslip and vacuum grease leaving the center of the chamber with suspension buffer, treated bead and molecule of interest untethered (FIG. 21D). To let molecule of interest to be bound to the edge of the coverslip and mobile bead, the slide was rotated for 120 minutes at room temperature. After 120 minutes, the slide is ready for measurement. By uncoiling the myosin S2 peptides, the stability and flexibility of this region was measured with free fall mode in conjunction with rotational mode of GFS. In addition, impact of anti-S2 peptides on the stability of myosin S2 peptide were tested using the same technique.

Methods

Competitive Enzyme Linked Immunosorbent Assay

Materials

Phosphate buffer saline (PBS) contained 0.14 M sodium chloride, 2.7 mM potassium chloride, 1.5 mM potassium phosphate monobasic, and 8.1 mM sodium phosphate dibasic with pH 7.4. Detergent buffer was made with 0.05% triton X-100 in PBS, blocking buffer was made with 3% powdered milk in detergent buffer. Assay buffer contained 100 mM potassium phosphate dibasic, 100 mM potassium phosphate monobasic, 1 M potassium chloride and 10 mM magnesium chloride with pH 7.0. Stocks of primary antibody (polyclonal antibody anti-S2), rabbit skeletal myosin, human cardiac myosin S2 peptide, stabilizer and destabilizer peptide. Secondary antibody conjugated with alkaline phosphatase was anti-guinea pig immunoglobulin G (IgG)-alkaline phosphatase (Sigma-Aldrich, catalog number A5062) produced in goat and isolated by affinity chromatography. Substrate was 5-Bromo-4-chloro-3-indolyl phosphate (BCIP) tablets dissolved in 10 ml of distilled water per tablet and 96 well microtiter plate.

Methodology

Competitive Enzyme Linked Immunosorbent Assay (cELISA) is a classical immunochemical test to validate the binding efficiency and specificity in lower molar concentrations (Yorde et al., 1976; Voller et al., 1978; Walker, J. M. 1996). In this assay the polyclonal antibody anti-S2 raised against single alpha helix of myosin S2 would be used to compete with stabilizer or destabilizer peptide to bind myosin S2 in rabbit skeletal myosin molecule as well as small human cardiac myosin S2 peptide. This cELISA, thus have two molecules polyclonal anti-S2 and stabilizer peptide which have two binding sites one on rabbit skeletal myosin and the other one being on small human cardiac myosin S2. Since both polyclonal anti-S2 and stabilizer peptide were designed against human β-cardiac myosin S2 they both would have a stronger affinity towards the smaller human β-cardiac myosin S2 peptide against the myosin S2 on rabbit skeletal myosin.

Figure 22:
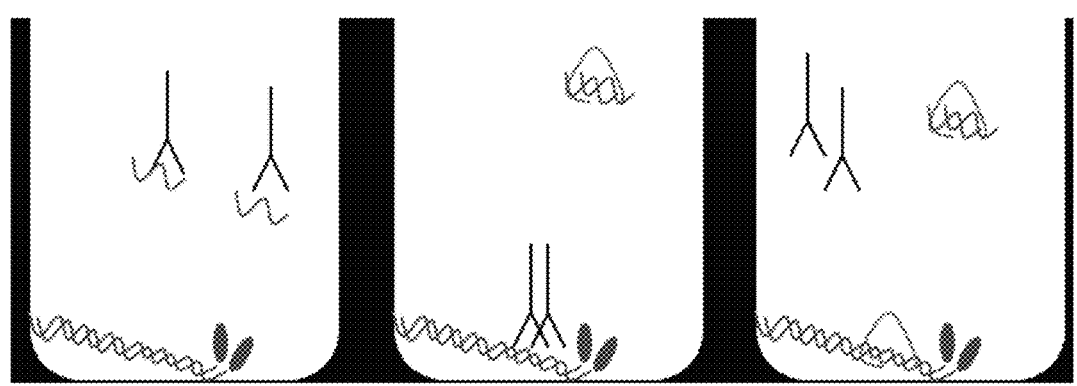
FIG. 22 illustrates a sketch of an exemplary cELISA setup: Left image shows rabbit whole skeletal myosin (red) coated on to the wells with human β-cardiac myosin S2 peptide (purple) with primary polyclonal anti-S2 antibody (black); Middle image shows lower amounts of stabilizer or destabilizer peptide (green) added will bind human cardiac myosin S2 peptide (purple) and primary polyclonal anti-S2 antibody (black) will bind rabbit skeletal myosin (red); and, Right image shows that higher amounts of stabilizer or destabilizer peptide (green) added will bind both human cardiac myosin S2 peptide (purple) and rabbit skeletal myosin (red) allowing the dissociation of primary polyclonal anti-S2 antibody (black) from the assay, as described in detail in Example 1, below.

FIG. 22 illustrates a sketch of cELISA setup. (Left) Rabbit whole skeletal myosin (red) coated on to the wells with human β-cardiac myosin S2 peptide (purple) with primary polyclonal anti-S2 antibody (black). (Middle) Lower amounts of stabilizer or destabilizer peptide (green) added will bind human cardiac myosin S2 peptide (purple) and primary polyclonal anti-S2 antibody (black) will bind rabbit skeletal myosin (red). (Right) Higher amounts of stabilizer or destabilizer peptide (green) added will bind both human cardiac myosin S2 peptide (purple) and rabbit skeletal myosin (red) allowing the dissociation of primary polyclonal anti-S2 antibody (black) from the assay.

To test the binding specificity and efficiency of stabilizer or destabilizer peptide the following setup was used. Start of the setup would be to coat the wells with rabbit skeletal myosin molecule and add appropriate amount human cardiac myosin S2 peptide that would bind the primary polyclonal anti-S2 antibody and when washed there won't be enough primary polyclonal anti-S2 antibody to bind myosin S2 of rabbit skeletal myosin adsorbed on the wells. When alkaline phosphatase conjugated secondary antibody is added on to the wells, it won't have enough or none primary polyclonal anti-S2 antibody to bind. After addition of color developing BCIP substrate to the wells it would lead to low or no color development leading to lower optical density (OD).

Next would be to add increasing amounts of stabilizer or destabilizer peptide to the above setup, if stabilizer or destabilizer peptide is specific and has higher binding efficiency to myosin S2, observed results would be that at lower concentration of stabilizer peptide, the stabilizer or destabilizer peptide would bind to human cardiac myosin S2 and block the binding of primary polyclonal anti-S2 antibody to human cardiac myosin S2 peptide. Thus polyclonal anti-S2 antibody would bind to myosin S2 in rabbit skeletal myosin coated on wells, this in turn would allow enzyme conjugated secondary antibody to bind this polyclonal antibody on wells leading to color development and increase in OD after addition of BCIP substrate.

As the concentration of stabilizer or destabilizer peptide increases, it would saturate by binding to all the human cardiac S2 peptide available, next available myosin S2 would be on rabbit skeletal myosin and this stabilizer or destabilizer peptide would bind to this myosin S2 on the wells. Thus polyclonal anti-S2 antibody won't have any other myosin S2 sites to bind, leading to no sites available to bind enzyme linked secondary antibody consequently causing low color development or lower OD upon addition of BCIP substrate. This change in OD from lower OD with no stabilizer or destabilizer to higher OD with increasing amounts of stabilizer or destabilizer peptide and then again back to lower OD with higher amounts of stabilizer or destabilizer peptide would be able to confirm the binding efficiency of stabilizer peptide to myosin S2 as well convey the cross-specificity of stabilizer or destabilizer peptide to myosin S2 of human cardiac and rabbit skeletal myosin.

To perform this specific set up of cELISA two values had to be determined, first being the minimal amount of primary polyclonal anti-S2 antibody required to bind myosin S2 on rabbit skeletal myosin coated on to the wells of microtiter plates thus giving a response by color development upon addition of enzyme linked secondary antibody following BCIP substrate. Second being the minimal concentration of human cardiac myosin S2 that would bind all the primary polyclonal anti-S2 antibody leading to no color development or low OD upon addition of enzyme linked secondary antibody following BCIP substrate. These two values determined will confirm that no or low OD at the beginning when there is no stabilizer or destabilizer added is because human cardiac myosin S2 peptide is bound to all available primary antibody, thus no sites for enzyme linked secondary antibody to bind. After addition of increasing amounts of stabilizer and destabilizer peptides, these peptides bind human cardiac myosin S2 peptide first allowing primary polyclonal anti-S2 to bind myosin S2 of rabbit skeletal myosin causing a rise in OD. With increasing amounts of stabilizer and destabilizer peptides added comes a stage when they saturate all the available human cardiac myosin S2 peptide available thus progressing towards to bind next available myosin S2 which is on rabbit skeletal myosin. As a result primary polyclonal anti-S2 antibody won't be have any myosin S2 region available leading to low OD or decline in OD when enzyme linked secondary antibody with BCIP are added.

In Vitro Motility Assay

Materials

Fluorescent microscope with 100× glycerol immersion lens and temperature regulated stage, Intensified charged couple device (ICCD), Rabbit skeletal myosin, purified G-actin, purified MyBPC, stabilizer peptide, destabilizer peptide, potassium chloride, imidazole, magnesium chloride, dithioerythritol, bovine serum albumin,α chymotrypsin, catalase, glucose oxidase, glucose, methyl cellulose, phenylmethylsulfonylfluoride, methanol, adenosine triphosphate, dichlorodimethylsilane, chloroform, rhodamine phalloidin, glass slides, glass coverslips and vacuum grease.

Method

Figure 23:
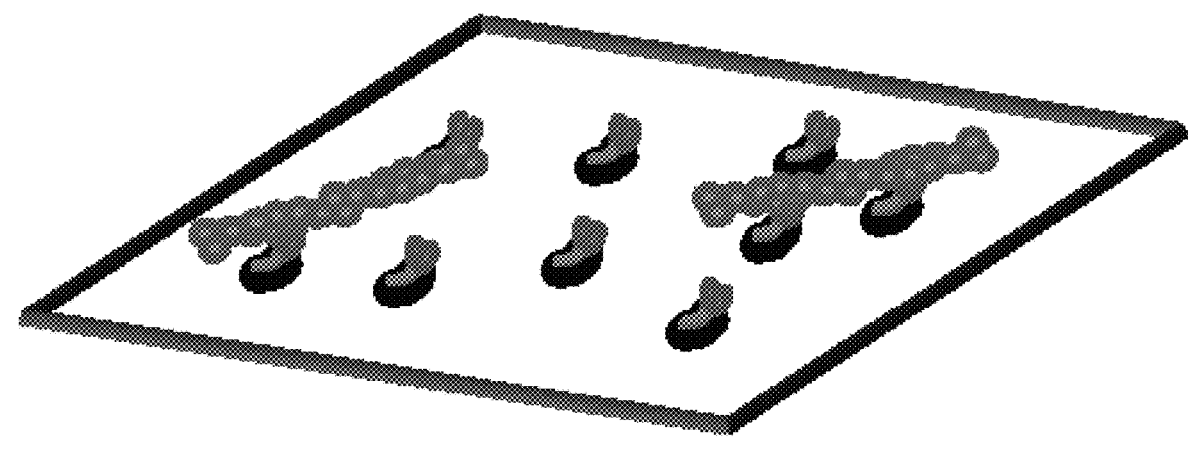
FIG. 23 is a schematic of a typical in vitro motility assay, where fluorescently labelled actin thin filaments (blue) sliding over coverslip coated with myosin molecules (red), as described in detail in Example 1, below.

FIG. 23 is a schematic of a typical in vitro motility assay. Fluorescently labelled actin thin filaments (blue) sliding over coverslip coated with myosin molecules (red).

In vitro motility assay a classic method to determine the sliding velocity of actin thin filaments over immobilized myosin in the presence of ATP (Kron et al., 1991). The assay involves the immobilization of myosin either in thick filament assembly or through individual myosin molecule on a nitrocellulose or dichlorodimethylsilane treated coverslip. Fluorescently labelled actin thin filament is allowed to slide across the bound myosin molecule upon addition of ATP. Sliding of actin over myosin treated with myosin S2 binding proteins would establish their effect over acto-myosin interaction and overall force produced. Myosin heavy meromyosin would be enough to test the effect of stabilizer and destabilizer over the acto-myosin interaction, however to test the effect of MyBPC over myosin reconstituted in its thick filament form would be required since MyBPC binds to both light meromyosin and myosin S2. Myosin in its thick filament form will improve the binding of MyBPC to a myosin molecule rather than a single myosin molecule immobilized on a glass surface.

Purification of Myosin Heavy Meromyosin with ATP Sensitive Heads

Rabbit skeletal myosin is dialyzed against buffer containing 0.5 M potassium chloride and 10 mM imidazole with pH 7.0 overnight to remove the impurities. Dialyzed myosin undergoes trypsin digestion with 1 mM magnesium chloride and α-chymotrypsin, digestion was stopped after addition of phenylmethylsulfonylfluoride in methanol at room temperature. Tryptic digest of myosin is dialyzed overnight at 4° C. against buffer containing 0.04 M potassium chloride and 10 mM imidazole with pH 7.0. Dialyzed tryptic digest of myosin is centrifuged at 21000 g for 60 minutes at 4° C. to yield myosin heavy meromyosin in the supernatant. This myosin heavy meromyosin achieved has a mixture of ATP sensitive and ATP insensitive heads. To purify myosin heavy meromyosin with ATP sensitive myosin S1 heads, F actin is added at an equimolar concentration to the unpurified myosin heavy meromyosin extract along with 1 mM ATP and magnesium chloride. Low salt assay buffer (25 mM potassium chloride, 10 mM imidazole, 2 mM magnesium chloride and 10 mM dithioerythritol with pH 7.0) was used as mixing solvent for the myosin heavy meromyosin purification step. Purified myosin heavy meromyosin with ATP sensitive heads are suspended in the supernatant when unpurified myosin heavy meromyosin with F actin, ATP and magnesium chloride is centrifuged with the speed of 21000 g at 4° C. ATP insensitive heads will bind F actin irreversibly thus forming the precipitate in the centrifugation step. Purified myosin heavy meromyosin with ATP sensitive heads are ready for the in vitro motility assay.

Purification of Myosin Thick Filament with ATP Sensitive Heads

Rabbit skeletal myosin is diluted in high salt buffer (0.3 M potassium chloride, 2 mM magnesium chloride, 10 mM imidazole and 10 mM dithioerythritol with pH 7.0) to around 10 μM. Equimolar concentration of F actin along with 1 mM ATP and magnesium chloride is added to the diluted skeletal myosin. Myosin molecule with ATP insensitive heads will bind to F-actin and gets precipitated out upon centrifugation with speed of 21000 g at 4° C., while myosin molecules with ATP sensitive heads will form the supernatant. High salt will help to maintain the skeletal myosin in its single molecular form thus allowing to purify myosin molecules with ATP sensitive heads from insensitive heads. Exchanging this purified myosin molecule with ATP sensitive heads from high salt buffer to low salt assay buffer allows the myosin thick filament formation with ATP sensitive myosin S1 heads.

Myosin Thick Filaments Thus Formed are Ready for In Vitro Motility Assay.

Rhodamine phalloidin labelling of F-actin F-actin and rhodamine phalloidin are mixed in 1:5 micro molar concentration ratio with low salt assay buffer. Rhodamine phalloidin binds in between the grooves of actin subunits of F-actin. The mixture of F-actin and rhodamine phalloidin is allowed to incubate overnight at 4° C. to allow maximal labelling of F-actin.

Figures 24, 25A:
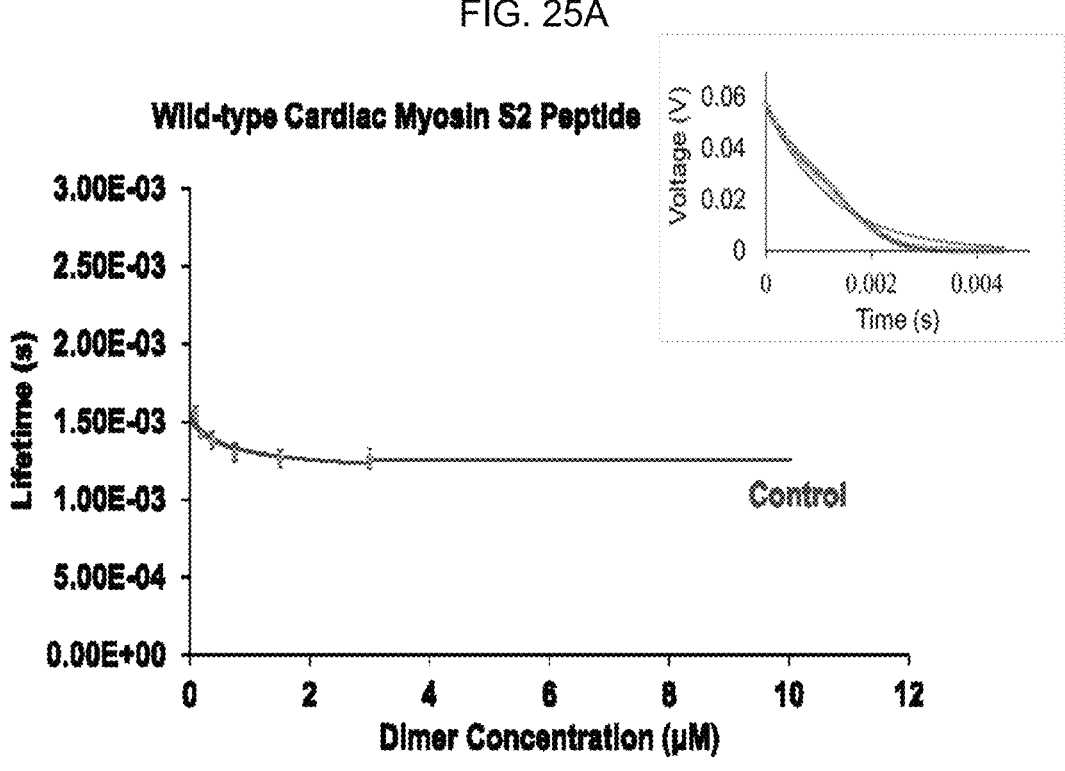
FIG. 24 illustrates a perfusion chamber for in vitro motility assay: pieces of glass coverslips (blue) attached on to a glass slide (black) and coverslip treated with myosin (red) added to create a chamber; buffer and solution added from one side (green arrow point) and wicked through other end with tissue paper (brown), as described in detail in Example 1, below.
FIG. 25A graphically illustrates lifetime of cardiac wild-type muscle myosin S2 donor probe.

FIG. 24 illustrates a perfusion chamber for in vitro motility assay. Pieces of glass coverslips (blue) attached on to a glass slide (black) and coverslip treated with myosin (red) added to create a chamber. Buffer and solution added from one side (green arrow point) and wicked through other end with tissue paper (brown).

Glass coverslips are coated with freshly prepared 2% dichlorodimethylsilane in chloroform. Perfusion chamber is created by two halves of glass coverslips on a clean glass slide with help of vacuum grease. The perfusion chamber is then sealed with dichlorodimethylsilane treated coverslip with two side open to allow perfusion of buffer from one end and wicking on the opposite end. First step in preparation of slide is to immobilize either purified myosin heavy meromyosin or myosin thick filaments. These purified products are diluted with low salt assay buffer to achieve a final concentration of 0.1 μM before adding them in to perfusion chamber. Myosin heavy meromyosin or myosin thick filaments are allowed to immobilize on dichloro-dimethylsilane treated coverslip for a minute. Unbound myosin is washed away by low salt assay buffer once and multiple washes with assay buffer mixed with 0.5 mg/ml bovine serum albumin (AB-BSA) blocks the unbound protein. Next step is to add 10 μM worth of F actin diluted in AB-BSA to the chamber to bind F-actin to myosin S1 heads. After this step ATP diluted in AB-BSA is added to allow F-actin to dissociate from active myosin S1 heads while F-actin would stay bound to inactive myosin S1 heads. This is an additional step to select the ATP sensitive myosin S1 heads. Next step is to give multiple washes with AB-BSA to block the unbound proteins. Following this washing step is addition of rhodamine phalloidin labelled F-actin diluted thousand times with AB-BSA. Fluorescently labelled F-actin is allowed to bind myosin S1 heads for few minutes. Later is the addition of ATP diluted to 1 mM in low salt buffer containing 0.5 mg/ml bovine serum albumin, 25 μg/ml glucose oxidase, 45 μg/ml catalase, 10 mg/ml glucose and 0.5% methyl cellulose (AB-BSA-GOC).

After this step, slide is placed on to the stage of fluorescent microscope maintained at 37° C. to allow efficient movement of fluorescently labelled actin thin filaments over myosin S1 of myosin heavy meromyosin and myosin thick filament. Slide is viewed through Intensified charged couple device (ICCD) to image fluorescently labelled actin thin filaments and video is recorded for few minutes to record the sliding of actin thin filaments. Final step is to add ATP diluted to 1 mM in AB-BSA-GOC along with myosin S2 binding proteins to check their effect over acto-myosin interaction. Again the video is recorded to measure the actin sliding over myosin bound to myosin S2 binding proteins. The video recorded is analyzed by Image J software and manual tracking plugin of the software allows to track the movement of actin filament and yield the velocity of actin in microns per second.

Thus measuring the actin sliding velocity over myosin S1 heads of myosin heavy meromyosin in presence of destabilizer and stabilizer peptide, as well as sliding velocity of actin over myosin S1 heads of myosin thick filament in presence of MyBPC would reveal the effect of these myosin S2 binding proteins over acto-myosin interaction and overall force produced.

Results

Fluorescence Resonance Energy Transfer (FRET)

Anti-S2 Peptides have an Impact on MYH7

FRET measured the dissociation constant (binding affinity) between the myosin S2 dimers and the anti-S2 peptides. The anti-S2 peptides were designed computationally to target S2 region of cardiac muscle β-myosin (MYH7). Anti-S2 peptides were specifically designed against cardiac muscle myosin S2 peptides region 921 to 939. Impact of these peptides were further tested on the other two muscle myosin isoforms namely skeletal (MYH2) and smooth (MYH11). Result indicated that anti-S2 peptide had an effect on skeletal and cardiac muscle isoforms. Of the two peptides, one peptide was designed to bind across the dimer of S2 region and other was designed to associate with a monomer of S2. Anti-S2 peptides were designed with the purpose of binding and further stabilizing or destabilizing the myosin S2 coiled coil.

In FRET assay, Fluorescein Isothiocyanate (FITC) functioned as fluorescent acceptor probe and Terbium Diethylene Triamine Pentaacetic Acid-Cytosine (Lanthanide-DTPA-Cytosine) functioned as donor probe. Donor probe was conjugated to C-terminus of a myosin S2 peptide monomer and acceptor probe was conjugated to N-terminus of another myosin S2 peptide. In FRET as lanthanide of the donor probe decays, energy goes to fluorescein and it emits out energy in form of light. In addition, as the monomers come closer to each other, lifetime of donor decreases indicating a decrease in distance between donor and acceptor probe; an opposite effect is observed, with an increase in distance between the probes, distance increases. Lifetime of donor probe was measured in milliseconds.

Number of factors impacted the efficiencies of resonance energy transfer as mentioned before (Aboonasrshiraz, 2020). Experimental measurements of these factors are summarized as follow:

TABLE 1

| Calculated Critical Transfer Distance Parameters | | | | | | | | | |
|---|---|---|---|---|---|---|---|---|---|
| Probe | J | $K^2$ min | $K^2$ avg | $K^2$ max | Q | η | $R_0$min (nm) | $R_0$avg (nm) | $R_0$max (nm) |
| FITC $^{MYH7}$ | $1.05 \times 10^{15}$ | 0.66 | 0.67 | 0.69 | 0.47 | 1.4 | 4.42 | 4.43 | 4.45 |
| FITO $^{MYH2}$ | $1.05 \times 10^{15}$ | 0.66 | 0.67 | 0.69 | 0.40 | 1.4 | 4.30 | 4.31 | 4.33 |
| FITC $^{MYH11}$ | $1.05 \times 10^{15}$ | 0.66 | 0.67 | 0.69 | 0.40 | 1.4 | 4.30 | 4.31 | 4.33 |

Figure 25B:
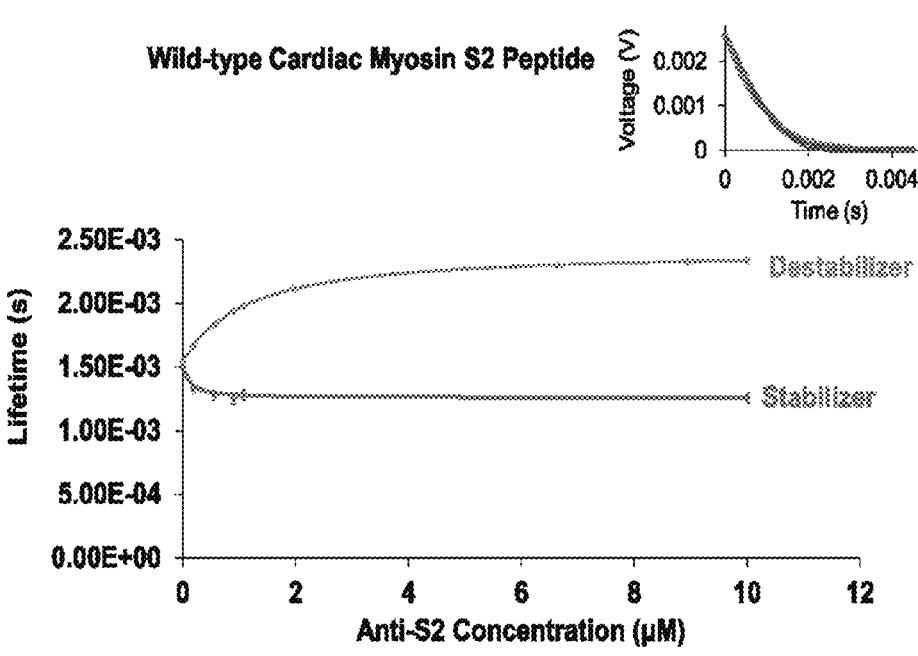
FIG. 25B graphically illustrates lifetime of cardiac wild-type muscle myosin S2 donor probe treated with the stabilizer (green) and the destabilizer (blue), as described in detail in Example 1, below.

During FRET assay, cardiac muscle myosin S2$^{pep}$ was treated with increasing concentrations of anti-S2 peptides. The test indicated the dissociation constant of cardiac muscle myosin S2$^{pep}$ control and treated with anti-S2 peptides (Table 3). Dilution to decrease the concentration of dimer cardiac muscle myosin S2$^{pep}$ was performed to measure binding affinity of coiled-coil peptide and in turn to measure minimal concentration for stable dimer formation (FIG. 25A). Concentration of dimer cardiac muscle myosin S2$^{pep}$ used to treat with anti-S2 peptides was 0.1 M. When treated with the stabilizer peptide, as the concentration of the stabilizer peptide increased, lifetime decreased; which states that it took less amount of time for energy to transfer from donor to acceptor probe thus a decrease in distance between donor and acceptor probe with increase in concentration of the stabilizer. An opposite effect was observed, in presence of the destabilizer peptide, as the concentration of the destabilizer peptide increased, lifetime increased as well. This states that it took longer amount of time for energy to transfer from donor to acceptor probe thus an increase in distance between donor and acceptor probe with increase in concentration of the destabilizer. (FIG. 25B)

The test indicated $K_d$ of cardiac muscle myosin S2$^{pep}$ control to be $3.08 \times 10^{-1} \pm 6.21 \times 10^{-2}$ μM with R value of 0.97. In presence of the stabilizer peptide $K_d$ was $2.12 \times 10^{-2} \pm 6.61 \times 10^{-3}$ μM with R value of 0.96 and in presence of the destabilizer peptide $K_d$ was $1.33 \pm 1.47 \times 10^{-1}$ μM with R value of 0.96. Our results strongly suggest that anti-S2 peptides have an impact on cardiac muscle myosin S2$^{pep}$ (Table 3). As mentioned before, anti-S2 peptides are specific to myosin S2 region, decrease or increase in distance between donor and acceptor probe is due to the binding of stabilizer and destabilizer peptide to the myosin S2 peptide.

FIG. 25(A): Lifetime of cardiac wild-type muscle myosin S2 donor probe. FIG. 25 (B) Lifetime of cardiac wild-type muscle myosin S2 donor probe treated with the stabilizer (green) and the destabilizer (blue). *Graph on top right hand corner is an example of exponential graph that was used to measure lifetime at each concentration.

TABLE 2

| Experimental measurement of separation distance between the acceptor probe and the donor probe | | | | | | |
|---|---|---|---|---|---|---|
| Muscle Peptides with Stabilizer | $T_D$ | $T_{DA}$ | EET | $R_{min}$ (nm) | $R_{avg}$ (nm) | $R_{max}$ (nm) |
| Cardiac | 1.73E−03 | 7.87E−04 | 5.45E−01 | 4.29 | 4.30 | 4.32 |
| | | 7.69E−04 | 5.56E−01 | 4.26 | 4.27 | 4.29 |
| | | 7.52E−04 | 5.66E−01 | 4.23 | 4.24 | 4.26 |
| Skeletal | 1.73E−03 | 4.82E−04 | 7.21E−01 | 3.67 | 3.68 | 3.69 |
| | | 4.29E−04 | 7.52E−01 | 3.57 | 3.58 | 3.60 |
| | | 3.76E−04 | 7.82E−01 | 3.47 | 3.48 | 3.50 |
| Smooth | 1.73E−03 | 8.69E−04 | 4.98E−01 | 4.31 | 4.32 | 4.34 |
| | | 3.09E−04 | 8.21E−01 | 3.33 | 3.34 | 3.36 |
| | | 0.00E+00 | 1.00E+00 | 0.00 | 0.00 | 0.00 |

TABLE 2-continued

| Experimental measurement of separation distance between the acceptor probe and the donor probe | | | | | | |
|---|---|---|---|---|---|---|
| Muscle Peptides with Stabilizer | $T_D$ | $T_{DA}$ | EET | $R_{min}$ (nm) | $R_{avg}$ (nm) | $R_{max}$ (nm) |
| E924K | 1.94E−03 | 6.08E−04 | 6.86E−01 | 3.88 | 3.89 | 3.91 |
| | | 4.61E−04 | 7.62E−01 | 3.64 | 3.65 | 3.67 |
| | | 3.14E−04 | 8.38E−01 | 3.36 | 3.37 | 3.38 |
| E930del | 1.89E−03 | 4.33E−04 | 7.71E−01 | 3.61 | 3.62 | 3.64 |
| | | 3.10E−04 | 8.36E−01 | 3.37 | 3.38 | 3.39 |
| | | 1.87E−04 | 9.01E−01 | 3.06 | 3.07 | 3.08 |

The distance between the donor and the acceptor probe, separation distance (R), was calculated using the formula below (Aboonasrshiraz, 2020):

$$E = R_0^6 / \left( R_0^6 + R^6 \right)$$

The formula uses critical transfer distance ($R_0$) and efficiency of energy transfer (E) to calculate separation distance (Aboonasrshiraz, 2020). Efficiency of energy transfer was measured using lifetime of the donor in presence and absence of the acceptor probe as in $$E = 1 - (\tau_{ad}/\tau_d)$$

Critical transfer distance was measured using summarized formula below:

$$R_0 = [8.785 \times 10^{-11} \kappa^2 J \eta^{-4} Q_D]^{1/6} \text{ nm}$$

Where Q is the quantum yield of the donor, $\eta$ is the refractive index of the medium between the donor and the acceptor probes, $\kappa^2$ is orientation factor, and J is the overlap integral (Aboonasrshiraz, 2020). Experimentally estimation of these parameters are summarized in Table 1.

Average of calculated separation distance of cardiac muscle myosin $S2^{pep}$ in presence of the stabilizer was 4.27 nm (Table 2). This distance is comparable to reported distance using computational simulation of about 4 nm (Taei, 2013). The value from separation distance of cardiac muscle myosin $S2^{pep}$ also suggests that monomers represent an equal population of both homodimers and heterodimers. Table 2 summarizes three values for $T_{DA}$, which are minimum, average, and maximum $T_{DA}$ and corresponding efficiency of energy transfer, and minimum, average, and maximum critical transfer distance.

Stabilizer Peptide has an Impact on MYH7 Mutant Peptide.

Figure 26A:
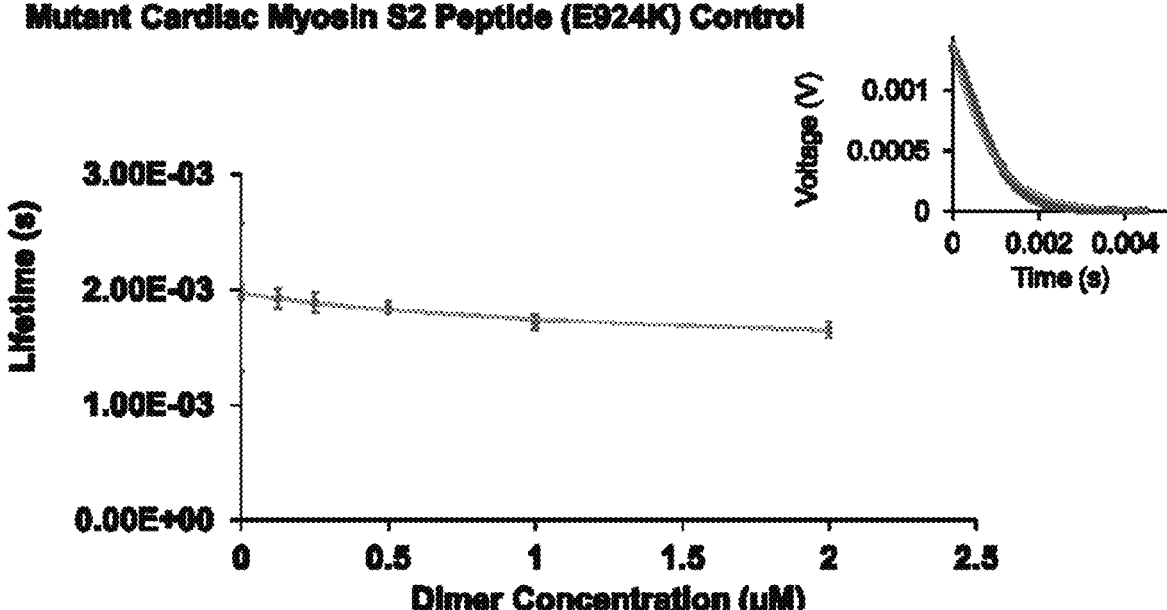
FIG. 26A graphically illustrates lifetime of cardiac E924K muscle myosin S2 donor probe.
Figure 26B:
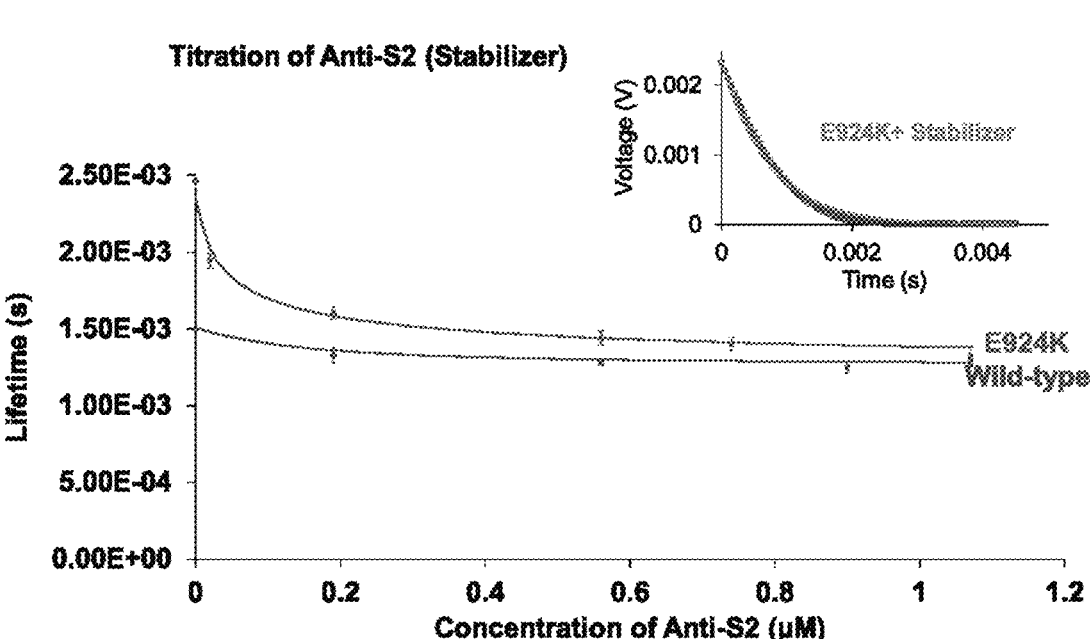
FIG. 26B graphically illustrates lifetime of cardiac E924K muscle myosin S2 donor probe treated with the stabilizer peptide (blue) compared to cardiac wild-type muscle myosin S2 donor probe treated with the stabilizer peptide (red), as described in detail in Example 1, below.

E924K and Edel930; the myosin S2 HCM mutants, form unstable dimers. Binding affinity of the dimer mutant peptides are lower compare to the dimer wild-type peptide (Table 3). Similar to cardiac muscle myosin $S2^{pep}$ wild-type, dilution by decreasing the concentration of both dimer cardiac muscle myosin $S2^{pep}$ mutant was performed (FIG. 26A). Concentration of dimer cardiac muscle myosin $S2^{pep}$ mutants used to treat with the stabilizer peptide was 0.1 µM. Impact of the stabilizer peptide was tested on both the mutants. E924K was treated with different concentrations of the stabilizer. Increase in concentration of the stabilizer lead to decrease of lifetime (FIG. 26B). The test indicated $K_d$ E924K control to be 2.54±1.72 µM with R value of 0.96. In presence of the stabilizer peptide $K_d$ was $3.62 \times 10^{-2} \pm 5.59 \times 10^{-3}$ M with R value of 0.98. Additionally, graph of treated E924K and cardiac muscle myosin $S2^{pep}$ wild type with the stabilizer peptide were compared (FIG. 26B). The calculated separation distance in presence of the stabilizer peptide was 3.65 nm. The results strongly suggest that the stabilizer peptide had an impact on E924K mutant muscle myosin S2 peptide by decreased lifetime of donor observed. (Table 3).

In FRET assay, like E924K, Edel930 was treated with different concentrations of the stabilizer. Increase in concentration of the stabilizer lead to decrease of lifetime. The test indicated $K_d$ of Edel930 control to be 3.24±2.25 µM with R value of 0.99. In presence of the stabilizer peptide $K_d$ was $2.38 \times 10^{-1} \pm 4.14 \times 10^{-2}$ µM with R value of 0.93. Additionally, graph of treated Edel930 and cardiac muscle myosin $S2^{pep}$ wild type with the stabilizer peptide were compared. Calculated separation distance in presence of the stabilizer peptide was 3.38 nm. The results state that stabilizer peptide had an impact on Edel930 HCM mutant of cardiac muscle myosin $S2^{pep}$ (Table 3) by decreasing the distance between the HCM mutant dimer.

FIG. 26(A): Lifetime of cardiac E924K muscle myosin S2 donor probe. FIG. 26(B): Lifetime of cardiac E924K muscle myosin S2 donor probe treated with the stabilizer peptide (blue) compared to cardiac wild-type muscle myosin S2 donor probe treated with the stabilizer peptide (red).

Figure 27A:
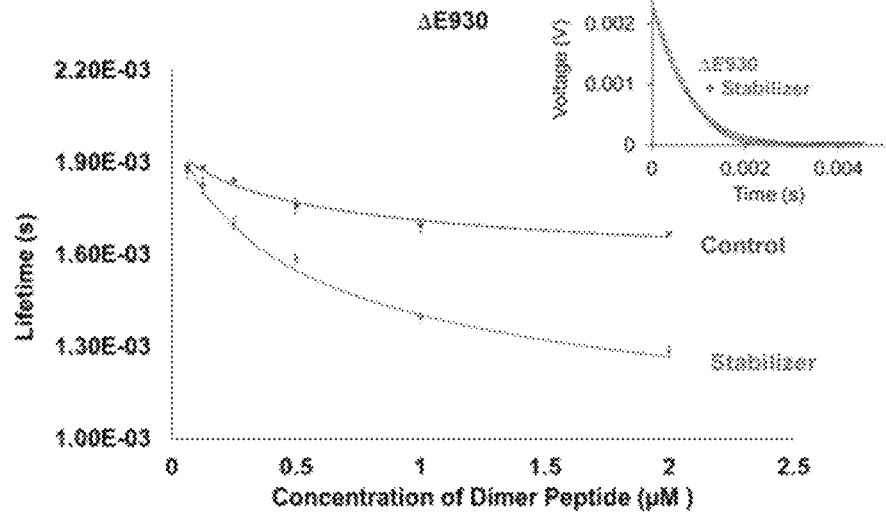
FIG. 27A-B illustrate the FRET results of mutant MYH7 isoform (ΔE930)
Figure 27B:
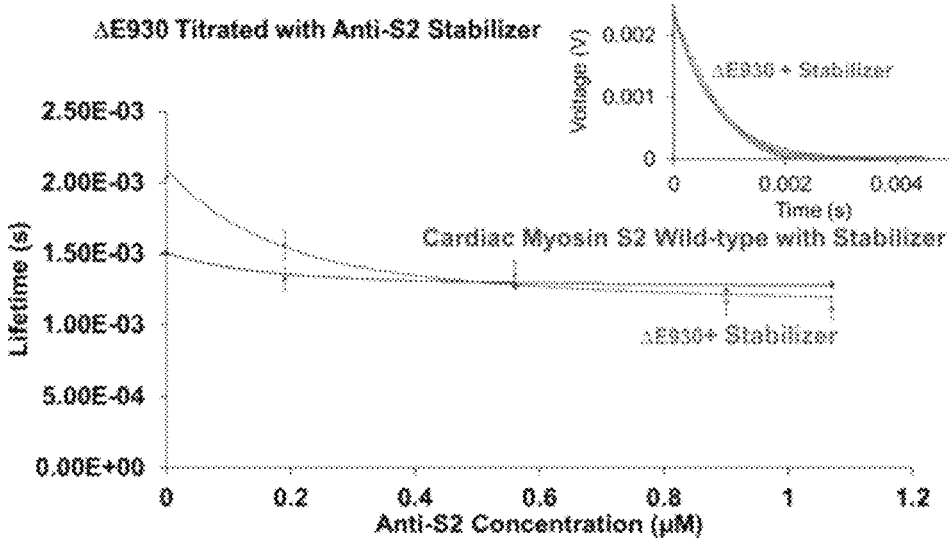

FIG. 27A-B illustrates the FRET results of mutant MYH7 isoform (ΔE930): (A) Lifetime of cardiac ΔE930 muscle myosin S2 donor probe treated with the stabilizer peptide (green) compared to control (red); (B) Lifetime of cardiac ΔE930 muscle myosin S2 donor probe treated with the stabilizer peptide (green) compared to cardiac wild-type muscle myosin S2 donor probe treated with the stabilizer peptide (red).

Anti-S2 Peptides have an Impact on MYH2

Figure 28A:
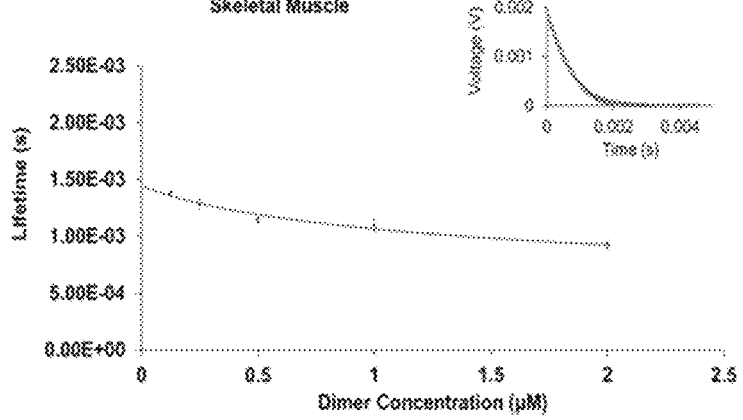
FIG. 28A graphically illustrates lifetime of skeletal muscle myosin S2 donor probe.
Figure 28B:
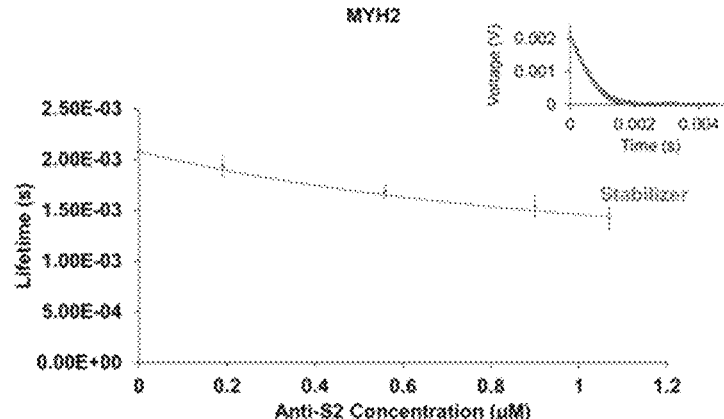
FIG. 28B graphically illustrates lifetime of skeletal muscle myosin S2 (0.1 uM) donor probe treated with the stabilizer; and, FIG. 28C graphically illustrates lifetime of skeletal muscle myosin S2 (2 uM) donor probe treated with the destabilizer, as described in detail in Example 1, below.
Figure 28C:
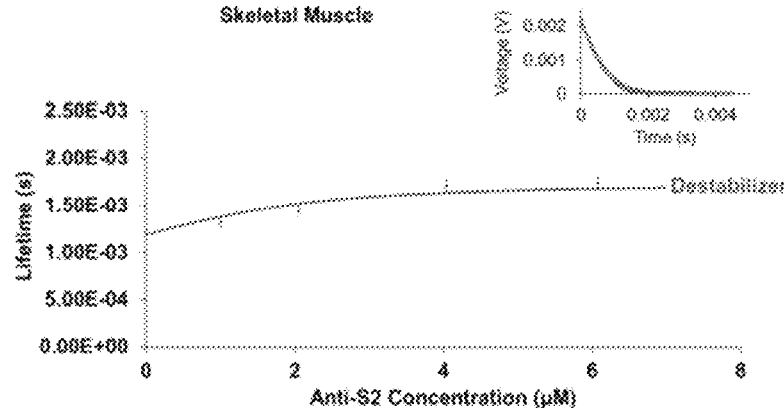

Like cardiac muscle myosin $S2^{pep}$, dilution by decreasing the concentration of dimer skeletal muscle myosin $S2^{pep}$ was performed and further was treated with different concentrations of anti-S2 peptides (FIG. 28A, 28B). Different concentrations of dimer skeletal muscle myosin $S2^{pep}$ was used with anti-S2 peptides. To treat skeletal muscle myosin $S2^{pep}$ with the stabilizer peptide, dimer concentration of 0.1 µM was used; in presence of the destabilizer peptide dimer concentration of 2 µM was used. Similar results as cardiac muscle myosin $S2^{pep}$ was observed when skeletal muscle myosin $S2^{pep}$ was treated with anti-S2 peptides. Increase in concentration of the stabilizer lead to decrease in lifetime (FIG. 28B). Oppositely, increase in concentration of the destabilizer lead to increase in lifetime (FIG. 28C). The test indicated $K_d$ of skeletal muscle myosin $S2^{pep}$ control to be $3.41 \times 10^{-1} \pm 2.91 \times 10^{-2}$ µM with R value of 0.98. In presence of the stabilizer peptide $K_d$ was $1.97 \times 10^{-2} \pm 2.87 \times 10^{-3}$ µM with R value of 0.98 and in presence of the destabilizer peptide $K_d$ was $4.69 \times 10^{-1} \pm 5.55 \times 10^{-3}$ µM with R value of 0.98. Calculated separation distance in presence of the stabilizer peptide was 3.58 nm. Our results strongly suggest that anti-S2 peptides had an impact on skeletal muscle myosin S2 peptide (Table 3).

FIG. 28(A) Lifetime of skeletal muscle myosin S2 donor probe. (B) Lifetime of skeletal muscle myosin S2 (0.1 uM) donor probe treated with the stabilizer. (C) Lifetime of skeletal muscle myosin S2 (2 uM) donor probe treated with the destabilizer.

Anti-S2 Peptides have No Impact on MYH11

Figure 29A:
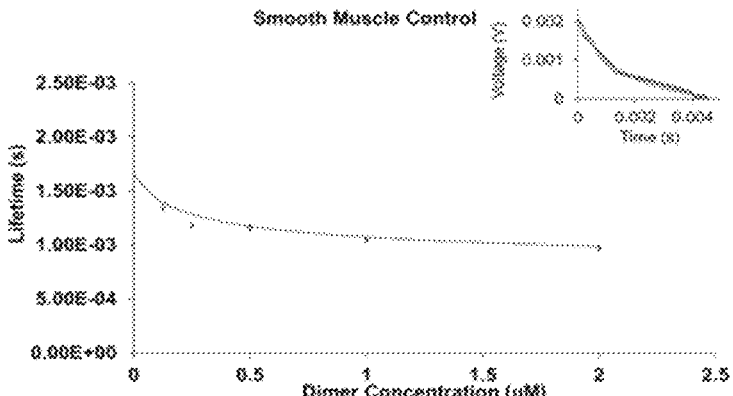
FIG. 29A-B illustrate a concentration-lifetime graph of smooth muscle myosin $S2^{pep}$ isoform (MYH11) in presence of anti-S2 peptides.

The specificity of peptides were later tested on the myosin S2 of the smooth muscle (MYH11). Dilution by decreasing the concentration of smooth muscle myosin $S2^{pep}$ dimer revealed that 0.1 M of the peptide was sufficient enough to form a stable dimer (FIG. 29A). Smooth muscle myosin $S2^{pep}$ was treated with different concentrations of anti-S2 peptides. The test indicated $K_d$ of smooth muscle myosin $S2^{pep}$ control to be $3.02 \times 10^{-1} \pm 2.02 \times 10^{-1}$ µM with R value of 0.98 and was not able to determine dissociation constant of smooth muscle myosin $S2^{pep}$ treated with anti-S2 peptides (Table 3). Calculated separation distance in presence of the stabilizer peptide was 3.34 nm. The data suggested that stabilizing and destabilizing effect of the anti-S2 peptides had no impact on smooth muscle myosin S2 peptide (FIG. 29B).

Figure 29B:
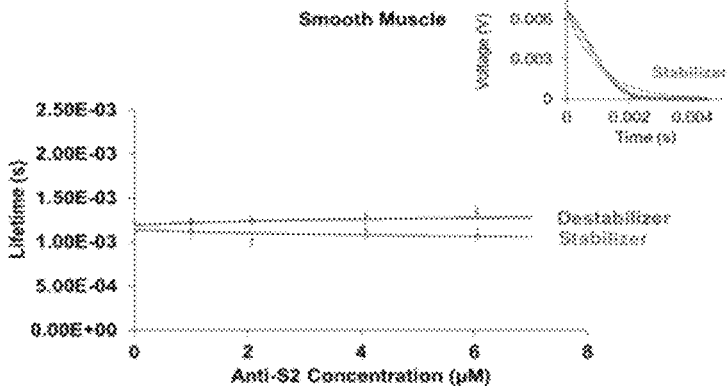

FIG. 29A-B illustrates a concentration-lifetime graph of smooth muscle myosin $S2^{pep}$ isoform (MYH11) in presence of anti-S2 peptides: (A) Lifetime of smooth muscle myosin S2 donor probe; (B) Lifetime of smooth muscle myosin S2 donor probe treated with the stabilizer (green) and the destabilizer (blue).

TABLE 3

Summary of dissociation constant and correlation
coefficient of FRET experiments.

| Experiment | Dissociation Constant ($\mu$M) ± SEM | Correlation Coefficient (R) |
|---|---|---|
| Smooth Myosin S2 | 3.02E–01 ± 2.02E–01 | 0.78 |
| Skeletal Myosin S2 | 3.41E–01 ± 2.91E–02 | 0.89 |
| Skeletal Myosin S2 with Stabilizer | 1.97E–02 ± 2.87E–03 | 0.99 |
| Skeletal Myosin S2 with Destabilizer | 4.69E–01 ± 5.55E–03 | 0.88 |
| Cardiac Myosin S2 | 3.03E–01 ± 4.42E–02 | 0.97 |
| Cardiac Myosin S2 with Stabilizer | 2.12E–02 ± 4.68E–03 | 0.96 |
| Cardiac Myosin S2 with Destabilizer | 1.33E+00 ± 1.47E–01 | 0.96 |
| Cardiac Myosin S2 Mutant, E930del | 1.11E+00 ± 1.15E–01 | 0.96 |
| Cardiac Myosin S2 Mutant, E930del with Stabilizer | 2.38E–01 ± 4.14E–02 | 0.92 |
| Cardiac Myosin S2 Mutant, E924K | 9.42E–01 ± 1.24E–01 | 0.96 |
| Cardiac Myosin S2 Mutant, E924K with Stabilizer | 3.40E–02 ± 4.50E–03 | 0.98 |

Summary of student's test on each compared pair of the curve fitted parameters is shown (Table 4). The stabilizer and the destabilizer tests detected a statistically significant difference ($p<0.05$). This indicates that the myosin S2 isoforms treated with anti-S2 peptides were significantly different.

TABLE 4

Summary of Student's test for FRET experiments

| | | P-value (t-test) |
|---|---|---|
| Controls | | |
| | Smooth vs. Skeletal | 8.56E–01 |
| | Smooth vs. Cardiac | 9.96E–01 |
| | Smooth vs. E924K | 5.37E–02 |
| | Smooth vs. E930del | 2.57E–02 |
| | Skeletal vs. Cardiac | 5.09E–01 |
| | Skeletal vs. E930del | 2.97E–03 |
| | Skeletal vs. E924K | 9.06E–03 |
| | Cardiac vs. E924K | 8.19E–03 |
| | Cardiac vs. E930del | 2.85E–03 |
| | E924k vs. E930del | 3.86E–01 |
| Skeletal | | |
| | Control vs. Stabilizer | 4.55E–04 |
| | Control vs. Destabilizer | 1.23E–02 |
| | Stabilizer vs. Destabilizer | 2.32E–06 |
| Cardiac | | |
| | Control vs. Stabilizer | 3.18E–03 |
| | Control vs. Destabilizer | 5.87E–03 |
| | Stabilizer vs. Destabilizer | 2.29E–03 |
| E924K | | |
| | Control vs. Stabilizer | 1.83E–03 |
| E930del | | |
| | Control vs. Stabilizer | 2.07E–03 |

Gravitational Force Spectroscopy

Anti-S2 Peptides have an Impact on MYH7

The specificity and activity of the anti-S2 peptides were further tested using GFS. GFS measured the mechanical stability of myosin S2 coiled-coil peptides treated with or without anti-S2 peptides. Anti-S2 peptides were designed with the purpose of binding and stabilizing or destabilizing the myosin S2 coiled coil and increase or decrease the amount of force produced during acto-myosin interaction. The designed anti-S2 peptides are specific to the myosin S2 regions. The peptides were designed computationally to target S2 region of cardiac muscle β-myosin (MYH7). Of the two peptides, one peptide was designed to increase mechanical stability of S2 region and one was designed to decrease.

The mechanical stability of the cardiac muscle myosin S2 coiled coil could be altered when treated with anti-S2 peptides. GFS was performed to uncoil the single molecule of myosin S2 peptide dimer in a direction perpendicular to the coiled coil axis. The myosin S2 molecule was further treated with anti-S2 peptides and mechanical stability was measured. The mechanical stability of coiled coil was measured by the amount of force required to uncoil the coiled coil structure along the length of the molecule.

The control was performed by tethering G-actin to the edge of both the cover slip and silica beads. The S1 heads of a myosin molecule was suspended by the actin treated coverslip and silica heads. From the force-distance curve fit (Aboonasrshiraz, 2020), the force required to uncoil the myosin molecule for a length of 60 nm was 2.67±0.23 pN with R value of 0.99 (FIG. 30). Shown result is as observed before (Singh, 2017).

FIG. 30 illustrates a force-distance graph of uncoiling a single molecule of cardiac myosin S2 peptide (n=10).

Next experiment was performed by treating both the coverslip and silica beads with the monomers of cardiac muscle myosin S2$^{pep}$, further allowing dimerization of the monomers to allow the suspension of myosin S2$^{pep}$ between coverslip and silica bead of GFS. Later these S2 dimers were treated with anti-S2 peptides. From the force-distance graph, the force required to uncoil cardiac muscle myosin S2 molecule for a length of 10 nm in absence of anti-S2 peptides was $8.63\times10^{-1}\pm7.45\times10^{-2}$ pN with R value of 0.98 (FIG. 31). In presence of anti-S2 peptides (stabilizer and destabilizer respectively) the force required was $1.55\pm1.46\times10^{-1}$ pN with R value of 0.98 and $4.36\times10^{-1}\pm3.30\times10^{-2}$ pN with R value of 0.98 (FIG. 31). The stabilizer anti-S2 peptide increased the amount of force required to uncoil the myosin S2 coiled coil by 1.80 times and an opposite effect observed with the treatment with the destabilizer peptide, the amount of force required decreased by 1.98 times (Table 5).

The force-distance data is fit to the equation as described previously (Singh, 2017). The deviation in the force fit for the myosin molecule with the stabilizer and the destabilizer was expected since the binding of the stabilizer to the myosin coiled coil would alter the entropy change in parameter a and binding of the destabilizer to the myosin S2 coiled coil would alter the enthalpy change in parameter c of the logarithmic force fit. The results confirmed that mechanical stability of MYH7 peptide is increased and decreased with respective anti-S2 peptides.

Fitted parameters in $F=a \ln(x+b)+c$ for the GFS data can be interpreted as $a=vkT$ in which k is Boltzmann's constant (the ideal gas law constant divided by Avogadro's number), T is absolute temperature (typically in Kelvin), and v is a proportionality constant (it appears to be equal to the inverse of the persistence length). The persistence length is a measure of stiffness, but the persistence length extracted from the "a" term is measured perpendicular to the length of the polymer which might make it somewhat different from normal persistence length measurements. Parameter "a" is inversely proportional to this stiffness. The "b" parameter is the linker length in attaching the peptides to the surfaces. The "c" parameter is a measure of change in enthalpy (H) with extension (x) such that $c=-\int dH/\int dx$, and is assumed to be constant with extension. This term would most closely be related to the number of hydrogen bonds that break during extension.

FIG. 31 illustrates a force-distance graph of uncoiling a single molecule of cardiac muscle myosin S2 wild-type isoform, MYH7, in presence of anti-S2 peptides. (Green) Force-distance graph of uncoiling a single molecule in presence of the stabilizer peptide (n=19). (Blue) Force-distance graph of uncoiling a single molecule (control; n=21). (Red) Force-distance graph of uncoiling a single molecule in presence of the destabilizer peptide (n=17).

Stabilizer Peptide has an Impact on MYH7 Mutant Peptide

GFS assay was further performed to test the mechanical stability of cardiac muscle myosin S2 carrying an HCM mutant E930del. The mechanical stability of cardiac muscle myosin S2 with E930del mutant was found to be 2.10 times unstable compared to wild type cardiac muscle myosin S2 (Table 5). Later the E930del dimer were treated with the stabilizer peptide to increase the stability of an unstable E930del dimer. The force required to uncoil the E930del in presence of stabilizer was greater compared to that in absence of stabilizer (FIG. 32).

From the force-distance graph, the force required to uncoil E930del myosin S2 molecule for a length of 10 nm in absence of the stabilizer peptide was $4.11 \times 10^{-1} \pm 2.97 \times 10^{-2}$ pN with R value of 0.98 (Table 5). In presence of the stabilizer peptide the force required was $1.07 \pm 8.28 \times 10^{-2}$ pN with R value of 0.98 (Table 5). The stabilizer peptide increased the amount of force required to uncoil the myosin S2 coiled coil by 2.60 times. The results indicate the mechanical stability of E930del dimer is increased in presence of the stabilizer peptide.

FIG. 32 illustrates a force-distance graph of uncoiling a single molecule of cardiac myosin S2 mutant peptide isoform, MYH7, in presence of anti-S2 peptide: (Green) Force-distance graph of uncoiling a single molecule in presence of the stabilizer peptide (n=27); and, (Blue) Force-distance graph of uncoiling a single molecule (control; n=28).

Anti-S2 Peptides have an Impact on MYH2

Furthermore, the skeletal muscle myosin $S2^{pep}$ (MYH2) molecule was treated with anti-S2 peptides. GFS was performed to uncoil the myosin dimer as a single molecule treated with or without anti-S2 peptides. The force required to uncoil the skeletal muscle myosin S2 molecule in presence of the stabilizer and the destabilizer was greater and smaller respectively compared to that in absence of the stabilizer or the destabilizer (FIG. 33).

From the force-distance graph, the force required to uncoil the skeletal muscle myosin S2 molecule for a length of 10 nm in absence of anti-S2 peptides was $4.50 \times 10^{-1} \pm 5.56 \times 10^{-2}$ pN with R value of 0.98 (Table 5). In presence of the stabilizer peptide the force required was $6.28 \times 10^{-1} \pm 4.32 \times 10^{-2}$ pN with R value of 0.98 and in presence of the destabilizer peptide force required was $1.84 \times 10^{-1} \pm 4.00 \times 10^{-2}$ pN with R value of 0.99 (Table 5). The stabilizer anti-S2 peptide increased the amount of force required to uncoil the skeletal muscle myosin S2 coiled coil by 1.40 times and an opposite effect was observed with the treatment of destabilizer peptide, the amount of force required decreased by 2.45 times. The results indicate that mechanical stability of skeletal muscle myosin S2 can also be altered in similar trend as that of cardiac muscle myosin $S2^{pep}$ with the anti-S2 peptides.

FIG. 33 illustrates a force-distance graph of uncoiling a single molecule of the skeletal myosin S2 peptide isoform (MYH2) in presence of anti-S2 peptides. (Green) Force-distance graph of uncoiling a single molecule in presence of the stabilizer peptide (n=24). (Red) Force-distance graph of uncoiling a single molecule in presence of the destabilizer peptide (n=23) (Blue) Force-distance graph of uncoiling a single molecule (control; n=22).

Anti-S2 Peptides have No Impact on MYH11

In GFS assay, the results similar to FRET experiments were observed. GFS was performed to uncoil the myosin dimer as a single molecule treated with or without of anti-S2 peptides. This test compared the stability and instability of smooth muscle myosin $S2^{pep}$ to control force distance curve. The results indicate an insignificant change in the force distance curve for a single molecule of smooth muscle myosin S2 dimer and smooth muscle myosin S2 dimer treated with anti-S2 peptides (FIG. 34). The force required to uncoil the smooth muscle myosin S2 to a length of 10 nm was similar (Table 5), and student's test on each compared pair of the curve fitted parameters did not detect a statistically significant difference (p>0.05). Therefore, it could be concluded that the stabilizer and the destabilizer do not have an impact on mechanical stability of smooth muscle myosin S2 peptide.

FIG. 34 illustrates a force-distance graph of uncoiling a single molecule of smooth myosin S2 peptide isoforms (MYH11) belonging to myosin heavy chain family in presence of anti-S2 peptides. (Green) Force-distance graph of uncoiling a single molecule in presence of stabilizer peptide (n=19). (Red) Force-distance graph of uncoiling a single molecule in presence of destabilizer peptide (n=19) (Blue) Force-distance graph of uncoiling a single molecule (control; n=14).

TABLE 5

Summary of myosin S2 molecular uncoiling length measured with GFS in presence and absence of anti-S2 peptidesfor all myosin S2 Isoforms and HCM mutant.

| Experiment | Length (nm) | Force (pN) ± SEM | No. of molecules | Correlation Coefficient (R) |
|---|---|---|---|---|
| Smooth Myosin S2 | 10 | 4.61E−01 ± 4.258−02 | 14 | 0.99 |
| Smooth Myosin S2 with Stabilizer | 10 | 4.96E−01 ± 7.60E−02 | 19 | 0.92 |
| Smooth Myosin S2 with Destabilizer | 10 | 4.51E−01 ± 2.98E−02 | 19 | 0.93 |
| Skeletal Myosin S2 | 10 | 4.50E−01 ± 5.56E−02 | 22 | 0.98 |
| Skeletal Myosin S2 with Stabilizer | 10 | 6.28E−01 ± 4.32E−02 | 24 | 0.98 |
| Skeletal Myosin S2 with Destabilizer | 10 | 1.84E−01 ± 4.00E−02 | 23 | 0.99 |
| Cardiac Myosin S2 | 10 | 8.63E−01 ± 7.45E−02 | 21 | 0.98 |
| Cardiac Myosin S2 with Stabilizer | 10 | 1.55E+00 ± 1.46E−01 | 19 | 0.98 |
| Cardiac Myosin S2 with Destabilizer | 10 | 4.36E−01 ± 3.30E−02 | 17 | 0.98 |
| Cardiac Myosin S2 Mutant, E930del | 10 | 4.11E−01 ± 2.97E−02 | 28 | 0.98 |
| Cardiac Myosin S2 Mutant, E930del with Stabilizer | 10 | 1.07E+00 ± 8.28E−02 | 27 | 0.98 |

Stabilizer peptide is specific to cardiac muscle myosin S2 and skeletal muscle myosin S2 peptides. Striated muscles are 87% identical and cardiac muscle myosin S2 and smooth muscle myosin S2 peptides are only 40% identical. Difference of 60% in amino acid sequences is the reason stabilizer has no effect on smooth muscle myosin $S2^{pep}$. It seems like the stabilizer increased the stiffness and had a little effect on H-bonds. Thus, cardiac muscle myosin S2 sequence is stiffer than the skeletal and smooth muscle peptides. The destabilizer also increases stiffness, but greatly reduces the number of H-bonds that need to be broken during extension. Statistical significance were measured using Wilcoxon-Mann-Whitney test; which is a nonparametric test of t-test (Table 6).

TABLE 6

Summary of P-values of t-test and Wilcoxon-Mann-Whitney test.

| | P-value (t-test) | P-value (Wilcoxon-Mann-Whitney) |
|---|---|---|
| Skeletal | | |
| Control vs. Stabilizer | <0.001 | 0.0001 |
| Control vs. Destabilizer | 0.0001 | <0.0001 |
| Stabilizer vs. Destabilizer | <0.0001 | <0.0001 |
| Cardiac | | |
| Control vs. Stabilizer | <0.0001 | 0.0001 |
| Control vs. Destabilizer | <0.0001 | <0.0001 |
| Stabilizer vs. Destabilizer | <0.0001 | <0.0001 |
| E930del | | |
| Control vs. Stabilizer | <0.0001 | <0.0001 |
| Smooth | | |
| Control vs. Stabilizer | 0.7595 | 0.0821 |
| Control vs. Destabilizer | 0.4895 | 0.3147 |
| Stabilizer vs. Destabilizer | 0.9049 | 0.7543 |

Stabilizer Peptide and Myosin Subfragment 2
Introduction and Idea Behind the Design and Use of Stabilizer Peptide The design of stabilizer peptide to stabilize the myosin S2 coiled coil came with the idea from an earlier study, where antibody raised against the whole myosin S2 coiled coil reduced the isometric force produced by the myosin molecule with no hindrance to myosin S1 activity to bind actin thin filaments and its ATPase activity (Sugi et al., 1992; Tsuchiya et al., 1998). Hence a molecule which can wrap around the myosin S2 coiled coil like an antibody against the whole myosin S2 should be able to replicate the effects of the antibody and reduce the isometric force produced. Along with this there were FHC mutation hotspots identified in the glutamate rich region in the proximal myosin S2 region (924-942), these mutations result in the hypertrophy of heart due to hypercontraction.

To alleviate the hypercontraction of heart muscles with the effect same as that of antibody raised against myosin S2, came the idea to use positively charge lysine residues which can bind to the glutamate rich myosin S2 region. Several computer simulations of different length of poly lysine residues along with variating the lysine residue with other amino acids to find the optimal length poly lysine residues which will wrap around the same glutamate rich region (924-942) of human β-cardiac myosin S2 with higher binding efficiency. Final stabilizer peptide obtained was, 17 poly 1 (levo) lysine residues linked together with phenyl alanine at 9th position and alanine at 11th position.

Stabilizer peptide thus designed through computer simulations to bind and wrap around the myosin S2 coiled coil in the glutamate rich region with the practical use to stabilize the myosin S2 coiled coil and decrease the amount of force produced through acto-myosin contraction. Next step was to check whether the stabilizer peptide binds to the same glutamate rich region of myosin S2 region it was designed against, cELISA was performed to check the specificity and binding efficiency of stabilizer peptide to myosin S2 region. GFS experiments was performed to evaluate the proposed stabilizing effect of stabilizer peptide over the myosin S2 region. Myofibrillar contractility assay was performed to verify that binding of stabilizer peptide to myosin S2 decreases the amount of shortening in myofibrils with the stabilizer peptide. In vitro motility assay was performed to confirm that binding of stabilizer peptide to myosin S2 would reduce the amount of force produced through acto-myosin interaction observed through reduced motility of actin thin filaments.

Competitive ELISA of Stabilizer Peptide to Myosin S2
Minimum Dilution of Primary Polyclonal Anti-S2 Antibody to Bind Rabbit Skeletal Myosin To perform successful cELISA of stabilizer peptide for myosin S2 against primary polyclonal anti-S2 antibody, two values were evaluated to setup the experiment. First was the minimum dilution of antibody with assay buffer that would give a positive optical density. Second was the amount of cardiac myosin S2 peptide would compete with rabbit skeletal myosin S2 to bind polyclonal anti-S2 antibody.

The wells of microtiter plate were coated with approximately, 200 nanograms of rabbit skeletal myosin diluted with cELISA assay buffer overnight. Several dilution of primary polyclonal anti-S2 antibody was prepared in assay buffer. The primary antibody dilutions created with assay buffer were in the increasing exponential order of 2 for example; $1:2^1$, $2^2$, $2^3$, $2^4$, . . . , $2^9$. This series of diluted primary polyclonal anti-S2 antibody were added in replicates to the wells of microtiter plates. After incubation for an hour, the unbound primary polyclonal anti-S2 antibody was washed with PBS and blocking buffer. Enzyme linked secondary antibody diluted 30,000 times in blocking buffer was added to all the wells and incubated at room temperature for an hour. After incubation, the plates were washed with detergent buffer, later BCIP substrate was added. The microtiter plate was place under a camera to record the color development in plates. The video was analyzed by Image J to acquire the optical density in the wells. The lowest dilution of primary polyclonal anti-S2 antibody which gave a positive OD was at $1:2^6$ or 1:64 times diluted primary polyclonal anti-S2 antibody (FIG. 35).

FIG. 35 graphically illustrates optical density versus dilutions of primary anti-S2 antibody. Mapped on x-axis is the exponential dilution for primary polyclonal anti-S2 antibody; where $1=1:2^1$, $2=1:2^2$ and so on.

Concentration of Human Cardiac Myosin S2 Peptide Required to Bind Primary Polyclonal Anti-S2 Antibody To evaluate the amount of cardiac myosin S2 peptide that would compete with rabbit skeletal myosin S2 to bind primary polyclonal anti-S2 antibody, the microtiter plate was coated with rabbit skeletal myosin first to that was added two fold dilutions of human cardiac myosin S2 peptide from 1000 nanomolar (nM) to 1 nM. Following this 1:64 diluted primary polyclonal antibody was added. After the washing step, secondary antibody is added followed by BCIP and development of color or OD was recorded and the video was analyzed by Image J. The OD will decrease as the concentration of human cardiac myosin S2 increases. With increasing amount of human cardiac myosin S2, it would bind to primary polyclonal anti-S2 antibody and get washed away, hence there won't be any primary antibody left for enzyme conjugated secondary antibody to bind thus there will be no or really low color development upon addition of BCIP substrate. The minimum amount of human cardiac myosin S2 peptide that would bind primary polyclonal anti-S2 antibody was at 62.5 nM (FIG. 36). Such a high binding efficiency was expected, since primary polyclonal anti-S2 antibody was raised against the same human cardiac myosin S2.

FIG. 36 graphically illustrates cELISA for competitive binding of polyclonal anti-S2 antibody to human β-cardiac myosin S2 and rabbit skeletal myosin S2.

Stabilizer Peptide Versus Polyclonal Anti-S2 Antibody

The cELISA performed to determine the specificity of stabilizer peptide to myosin S2 begins with the 96 well microtiter plate coated with rabbit skeletal myosin and adding to it, previously determined 1:64 diluted primary polyclonal antibody along with 62.5 nM human cardiac myosin S2 to all the wells. Following this two fold dilutions of stabilizer peptide from 0 to 250 nm was added in replicates to the well. Unbound protein complexes are washed off by PBS and blocking buffer. Enzyme conjugated secondary antibody is added to the wells and allowed to conjugate for an hour. After washing with detergent buffer, color developing substrate BCIP is added and development of color in the wells is recorded. The video is analyzed by Image J to get the OD in the wells.

The trend in the OD observed was from low to high and back to low OD with increasing concentrations of stabilizer peptide (FIG. 37A). In the wells in which there were no stabilizer peptide added the primary polyclonal antibody would bind to human cardiac myosin S2 peptide and gets washed away, hence secondary antibody would not have enough primary antibody left to bind thus resulting in a low OD.

As the amount of stabilizer peptide is increased in the consequent wells the OD kept on increasing. With the increasing amounts of stabilizer peptide, it would bind to available human cardiac myosin S2 peptide, thus primary polyclonal anti-S2 antibody won't have enough human cardiac myosin S2 peptide to bind to, hence primary antibody would bind to the next available myosin S2 site, which is on the rabbit skeletal myosin molecule coated on to the wells. Hence the primary antibody would remain stuck on to the wells after the washing step, thus allowing the development of color and OD upon addition of secondary antibody and BCIP substrate.

With the increasing amounts of stabilizer peptide comes a stage where the stabilizer peptide would saturate all the available human cardiac myosin S2 peptide and later would go and bind to the myosin S2 region available on the rabbit skeletal myosin coated on to the wells. As a result the primary polyclonal anti-S2 antibody won't have enough sites available to bind neither the human cardiac myosin S2 peptide nor the rabbit skeletal myosin molecule. Once again the enzyme conjugated secondary antibody won't have enough primary antibody left to bind, causing a sharp decline in the OD.

The curve fit gave the binding efficiency of stabilizer peptide to human cardiac myosin S2 peptide at 1.37 nM±0.023 (FIG. 37B). cELISA results established that stabilizer peptide designed has high binding efficiency to human cardiac myosin S2 peptide. The stabilizer peptide is also cross specific; since it was able to bind to both human cardiac myosin S2 and rabbit skeletal myosin S2.

FIG. 37A graphically illustrates OD versus increasing amounts of stabilizer peptide concentration. The low-high-low OD trend observed states the specific binding of stabilizer peptide to human cardiac myosin S2 peptide. FIG. 37B graphically illustrates curve fit to determine the binding efficiency of stabilizer peptide to human cardiac myosin S2 peptide.

Gravitational Force Spectroscopy with Stabilizer Peptide

The stabilizer peptide was designed with the aim to bind and stabilize the myosin S2 coiled coil and reduce the amount of contraction and overall force produced through acto-myosin interaction. cELISA experiment confirmed the specificity of the stabilizer peptide to myosin S2 region. Next was to verify the stabilization of myosin S2 coiled coil by the stabilizer peptide. This verification was done by performing the GFS assay with rabbit skeletal myosin in the presence of stabilizer peptide.

The point of attachment to tether myosin molecule between immobile edge of the coverslip and mobile beads, was at the acto-myosin S1 binding region. The edge of the coverslips and silica beads are coated with G-actin molecules. The slide thus prepared would have myosin molecule suspended by its myosin S1 heads binding to G actin molecule on edge of the coverslip and silica beads. Polyclonal anti-S2 antibody was not used to tether the myosin molecule for GFS assay, since the stabilizer peptide designed was specific to the same region where the polyclonal anti-S2 would bind, hence judging the stability of myosin S2 at the region of its antibody binding in presence of stabilizer peptide will be needless since there won't be any myosin molecule treated with stabilizer peptide, tethered with polyclonal anti-S2 antibody coated edge of coverslips and silica beads.

The control for this assay was setup by tethering rabbit skeletal myosin sans stabilizer peptide between G-actin coated immobile edge and mobile beads. To assay the effect of stabilizer peptide binding to myosin S2 region, GFS was performed with myosin molecules incubated with stabilizer peptide and tethering these treated myosin molecules at its myosin S1 heads with immobile edge and mobile beads coated with G-actin molecule. From the force distance curve fits, the force required to uncoil the myosin molecule for a length of 50 nm in absence and presence of stabilizer peptide was 3.62±0.37 pN and 5.46±0.10 pN respectively (FIG. 38 and Table 7). The R value for control and test force distance curve fits were 0.988 and 0.917 respectively (Table 7).

FIG. 38A-B illustrates a GFS curve fit for average forces to distance for the effect of stabilizer peptide over myosin S2 coiled coil: (A) Force distance curve for myosin molecule in absence of stabilizer peptide (n=7); (B) Force distance curve for myosin molecule in presence of stabilizer peptide (n=6). In dashed box; cartoon of a myosin molecule (red) with stabilizer peptide (green) tethered at myosin S1 actin with actin (cyan arrow) for GFS.

TABLE 7

| Length of uncoiled myosin S2 molecule in absence and presence of stabilizer peptide measured with GFS. | | | |
|---|---|---|---|
| | No. of molecules (n) | Length (nm) | Force (pN) | Correlation coefficient (R) |
| Myosin S2 (Control) | 7 | 50 | 3.62 ± 0.37 | 0.988 |
| Myosin S2 with stabilizer peptide (Test) | 6 | 50 | 5.46 ± 0.10 | 0.917 |

FIG. 39 illustrates a comparison of force distance curve of myosin molecule without stabilizer peptide (blue) and myosin molecule with stabilizer peptide added (red).

The force distance curve fits of myosin molecule uncoiled in absence and presence of stabilizer peptide showed the stabilizing effect of stabilizer peptide on myosin S2 of myosin molecule with 1.5 time the force required to uncoil myosin in presence of stabilizer peptide. Myosin molecule when uncoiled from its myosin S1 heads has similar force distance trace compared to that of when uncoiled from myosin S2 region (Singh et al., 2017) and stabilizer peptide being specific to myosin S2, the stabilizing effect observed was due to binding to stabilizer peptide to myosin S2.

Myofibrillar Contractility Assay with Stabilizer Peptide

The cELISA and GFS experiments with stabilizer confirmed that the stabilizer peptide is specific to myosin S2 as well as it has a stabilizing effect on the myosin molecule at its S2 region. Next test was to verify whether the stabilization of this myosin S2 region has an effect over the contractility of myofibrils.

Myofibrillar contractility assay with stabilizer peptide would be able to verify the stabilization effect of myosin S2 by stabilizer peptide over myofibrillar contraction. For the assay, rabbit skeletal myofibrils were washed several times with assay buffer. Small amount of myofibrils were placed on a glass slide and imaged through the microscope. To the same myofibrils 100 microliter of assay buffer containing 1 mM ATP was added and the myofibrils were imaged after 30 minutes to allow the myofibrils to take up ATP and allow the sarcomeres to shorten. These myofibrils are again imaged through microscope.

To test the effect of stabilizer peptide over the myofibrils, the washed rabbit skeletal myofibrils were incubated at room temperature with different concentrations of stabilizer peptide ranging 1-100000 nM in the multiples of 10. The myofibrils incubated with stabilizer peptide were placed on to a coverslip and imaged through microscope. To the same myofibrils, 100 μl of assay buffer with 1 mM ATP are added and the myofibrils were imaged after 30 minutes to allow the myofibrils to take up ATP resulting in sarcomere shortening.

Length of the sarcomere measured before and after addition gave the percentage contraction observed in the myofibrils without and with stabilizer peptide. For the control the percentage contraction in myofibril was at 22.25%±0.201 (FIG. 40). The percentage contraction observed in the myofibrils incubated with increasing concentrations of stabilizer peptide was reduced and saturated to 18.6% at 1000 nM of stabilizer peptide (FIG. 40A). The binding efficiency of stabilizer peptide to myofibrils was calculated to be at 6 nM stating the high binding efficiency of stabilizer peptide to myosin S2 present in myofibrils (FIG. 40B).

FIG. 40A-B graphically illustrate dose response of stabilizer peptide on myofibril contraction: (A) Percentage of contraction versus stabilizer in nanomolar concentration; (B) Percentage of contraction versus stabilizer in nanomolar concentration in the logarithmic power of 10.

In Vitro Motility Assay of Actin Thin Filaments Over Myosin HMM Incubated with Stabilizer Peptide.

The results from myofibrillar contractility assay confirmed that presence of stabilizer peptide slowed down contraction in myofibrils. Previously, cELISA and GFS experiments conveyed that stabilizer peptide binds to myosin S2 region and stabilizes that region. Thus it can be said that stabilization of myosin S2 region upon stabilizer peptide binding have a inhibiting effect on contraction of myofibrils. In vitro motility assay would be an ideal test to confirm the inhibiting effect of stabilizer peptide to force produced through acto-myosin interaction.

The setup of in vitro assay began with the extraction of myosin HMM from rabbit skeletal myosin by the virtue of tryptic digestion by α-chymotrypsin. The extracted myosin HMM were purified to yield myosin HMM with active myosin S1 heads by mixing and centrifuging the extracted myosin HMM with actin filaments along with ATP and magnesium chloride. Myosin HMM was used instead of whole myosin thick filaments, since stabilizer peptide binds to myosin S2 region; which is a part of myosin HMM, hence purified myosin HMM with stabilizer peptide would be ideal to test the effect stabilizer peptide over sliding velocity of actin thin filaments.

The purified myosin HMM with active myosin S1 heads are immobilized on dichloromethylsilane treated coverslips. Additional step to reduce the amount of dead myosin S1heads is performed by washing the myosin HMM coated coverslip with unlabeled actin thin filaments with addition of ATP in assay buffer through perfusion chamber. Next step was the addition of fluorescently labelled actin filaments followed by addition of ATP in AB-BSA-GOC buffer. These fluorescently labelled actin thin filaments were imaged by ICCD. To the same in vitro slide, stabilizer peptide diluted in AB-BSA-GOC buffer with ATP is added to test the motility of the same fluorescently labelled actin thin filaments in the presence of stabilizer peptide. Thus allowing, to compare the effect of stabilizer peptide over the motility of actin thin filaments upon binding to myosin S2 region of myosin HMM.

The in vitro motility assay was performed with two different concentration of stabilizer peptide, 20 nM and 100 nM respectively. Histogram for the velocity of actin thin filaments in absence and presence of stabilizer peptide is plotted (FIG. 41A). Distribution for the velocity of actin thin filaments in absence of stabilizer peptide was observed most for more than 7.0 microns/second and in the presence of stabilizer peptide the velocity was observed less than 7.0 microns/second. Histogram of the average velocity of actin thin filaments is plotted (FIG. 41B). The average velocity of actin thin filament in absence of stabilizer peptide was 7.18±0.26 microns/second (n=26), while in presence of 20 nM stabilizer it was reduced to 6.18±0.28 microns/second (n=23) and 6.21±0.14 microns/second (n=24) in presence of 100 nM (FIG. 41B). Student's t test confirmed the velocities observed of actin thin filaments in control and in presence of either 20 nM or 100 nM was statistically significant with p value less than 0.05 (Table 8). While the velocities observed in presence of 20 nM and 100 nM were not statistically significant with p value greater than 0.05 (Table 8).

FIG. 41A-B illustrates histograms for the velocity of actin thin filaments in presence of stabilizer peptide. (A) Histogram for the number of actin thin filaments with their respective velocity, control (blue); velocity of actin in absence of stabilizer peptide, test (red); velocity of actin thin filaments in presence of 20 nM stabilizer peptide and test (green); velocity of actin thin filaments in presence of 100 nM stabilizer peptide. (B) Histogram for the average velocities of actin thin filaments in control (blue) (n=26), test with 20 nM stabilizer peptide (red) (n=23) and test with 100 nM stabilizer peptide (green) (n=24).

TABLE 8

| Table for student's t-test to signify the effect of stabilizer peptide over the velocity of actin thin filaments. | | |
| --- | --- | --- |
| Sample: Velocity of actin filaments | p (T ≤ t) one-tail | p (T ≤ t) two-tail |
| Control and 20 nM stabilizer peptide | 0.007414352 | 0.014828703 |
| Control and 100 nM stabilizer peptide | 0.001647415 | 0.00329483 |
| 20 nM stabilizer peptide and 100 nM stabilizer peptide | 0.4684888724 | 0.936977448 |

Conclusion

Stabilizer peptide was designed to bind to myosin S2 and stabilize the coiled coil in that region with the implication that this stabilization of myosin S2 coiled coil would have an inhibiting effect on the contraction in myofibrils and over all force produced through acto-myosin interaction.

cELISA experiment performed where stabilizer peptide and polyclonal anti-S2 antibody were competed to bind human cardiac myosin S2 peptide and rabbit skeletal myosin S2 (FIG. 37). The experiment performed established that stabilizer peptide was specific to myosin S2 and especially to the proximal myosin S2 region (924-942). The stabilizer peptide had a high binding efficiency with binding constant of 1.38 nM to human cardiac myosin S2 peptide.

In the course of experiment it was also found that stabilizer peptide was also cross specific where it could bind to myosin S2 of human cardiac myosin and rabbit skeletal myosin with relatively high specificity to human cardiac myosin S2 than rabbit skeletal myosin.

GFS experiment performed with stabilizer peptide on rabbit skeletal myosin was able to show that binding of stabilizer peptide stabilized the myosin S2 region. In the absence of stabilizer peptide the myosin molecule was able to uncoil much faster with the force required to uncoil the myosin molecule to a length of 50 nm was 3.62 pN. In the presence of stabilizer peptide, to uncoil the myosin molecule to the same length of 50 nm was 5.46 pN, which was 1.5 times higher than in absence of stabilizer peptide (FIG. 39, Table 7). The binding of stabilizer peptide to myosin molecule thus stabilized the myosin coiled coil since force required to pull the myosin molecule in presence of stabilizer peptide was higher than in the absence of stabilize peptide. cELISA experiment already showed that stabilizer peptide binds to myosin S2, hence the stabilization of myosin molecule by stabilizer peptide should be at the myosin S2 region.

Myofibrillar contractility assay performed showed that stabilization of myosin S2 region upon binding of stabilizer peptide reduced the percentage of contraction in myofibrils treated with stabilizer peptide. Percentage contraction of myofibrils in control was approximately at 22% which dropped down to approximately 18% in increasing amounts of stabilizer peptide. The effective concentration where stabilizer peptide decreased the percentage of contraction in myofibrils was at 6 nM.

In vitro motility of fluorescently labelled actin thin filaments over myosin HMM treated with stabilizer peptide was decreased compared to the motility of actin filaments over myosin HMM with no treatment of stabilizer peptide. The velocity of actin thin filaments in control assay was 7.18 microns/second, and in test assay with 20 nM stabilizer peptide was reduced to 6.18 microns/second, while test assay with 100 nM stabilizer peptide was at 6.21 microns/second (FIG. 41). The in vitro motility assay thus performed, showed that sliding of actin thin filaments over myosin HMM treated with stabilizer peptide was reduced compared to control. Reduction in the velocity of actin can only be explained by reduction in acto-myosin interaction and thus overall decrease in the amount of force produced.

The experiments performed was able to substantiate that a stabilize myosin S2 region have an inhibiting effect over myofibril contraction, acto-myosin interaction and overall force produced. The aforesaid experiments were performed with wild type rabbit skeletal myosin with no changes introduced to myosin S1 heads or the myosin S1-S2 hinge, the only characteristic, in use was the binding of stabilizer peptide to myosin molecule. And cELISA has already, shown that it was specific to myosin S2, hence the decreased contraction and motility observed was due to binding of stabilizer peptide to myosin S2 and GFS experiment showed that this binding stabilized the myosin molecule at the S2 region due to specific binding of stabilizer peptide. Thus stabilization of myosin S2 coiled coil by stabilizer peptide had a role in controlling the amount of myosin S1 heads (N$_t$) available to bind actin filaments, evidenced by reduction in contraction of myofibrils and motility of actin over myosin HMM treated with stabilizer peptide.

Destabilizer Peptide and Myosin Subfragment 2

The idea for destabilizer peptide was to destabilize the myosin S2 coiled coil and increase the amount of myosin S1 heads available to bind actin thin filaments, thus resulting in increase in myofibril contraction and overall force produced through acto-myosin interaction. This property of destabilizer would be useful in cardiomyopathy mutations which results in dilated cardiomyopathy and heart failure due to hypo contraction in heart muscles, thus increasing the amount of contraction in heart muscles with hypo contraction could alleviate the defects caused by hypo contraction.

The methodology behind the destabilization came with the binding of polyclonal anti-S2 antibody to myosin S2. The polyclonal anti-S2 was raised against a single α-helix of the myosin S2 coiled coil, thus polyclonal anti-S2 antibodies will have two sites to bind in a myosin S2 coiled coil at each individual α-helices. Thus both the α-helices when occupied by polyclonal anti-S2 antibody would interfere with the natural coiled coil formation between α-helices of myosin S2 resulting in a destabilized coiled coil. Thus GFS and myofibrillar contractility assay was performed with rabbit skeletal myosin and myofibril with polyclonal anti-S2 antibody to check the effect of the destabilized myosin S2 coiled coil. GFS performed with polyclonal anti-S2 antibody treated rabbit skeletal myosin gave much faster uncoiling of myosin molecule compared to that of control. Myosin uncoiled to a length of 168 nm with the force of 2.1 pN in presence of polyclonal anti-S2 antibody, while the uncoiled length of myosin in the control was 138 nm with the force of 4.8 pN (FIG. 42). Thus GFS assay confirmed that polyclonal anti-S2 had a destabilizing effect on myosin molecule at myosin S2, since antibody was against the myosin S2. Myofibrillar contractility assay performed with myofibrils incubated with polyclonal anti-S2 antibody gave a much higher percentage of contraction than control myofibrils. Percentage contraction in control myofibrils was 20.5% and it rose to 34% in case of myofibrils treated with polyclonal anti-S2 antibody (FIG. 43).

This effect of polyclonal anti-S2 over myosin S2 coiled coil and myofibril contraction gave the idea to develop a small peptide which could simulate the same effects as that of polyclonal anti-S2 antibody. Hence the destabilizer peptide designed was the modified form of single α-helix of human β-cardiac myosin S2 (924-942), which have a higher binding efficiency to natural single α-helix of human β-cardiac myosin S2 thus interrupting the natural coiled coil formation of myosin S2 coiled coil.

Destabilizer peptide thus designed will be able to destabilize the myosin S2 coiled coil, and the effect of this destabilized coiled coil over myofibril contraction and force produced through acto-myosin interaction could be studied. Destabilizer peptide specificity to myosin S2 region was tested by performing the competitive ELISA. The destabilization of myosin coiled coil was tested by performing the GFS experiments with rabbit skeletal myosin treated with destabilizer peptide. Myofibrillar contractility assay was performed to study the effect of destabilizer peptide over the contraction of myofibrils treated with the destabilizer peptide. In vitro motility assay was performed to assay the effect of destabilizer peptide bound myosin HMM over the actin thin filaments thus establishing the effect of destabilizer peptide over the force produced through acto-myosin contraction.

FIG. 42A-B illustrates force distance traces for myosin treated with polyclonal anti-S2 antibody. (A) Force distance curve for myosin molecule without polyclonal anti-S2 antibody. (B) Force distance curve for myosin molecule with polyclonal anti-S2 antibody. Black arrows indicate the event of uncoiling and coiling back of myosin coiled coil.

FIG. 43 illustrates percentage contraction in myofibrils without (blue) and with polyclonal anti-S2 antibody (red). Competitive ELISA of Destabilizer Peptide to Myosin S2

The first experiment performed was to test whether the destabilizer peptide designed was specific to myosin S2 and do not bind anywhere else along the length of myosin molecule. cELISA was preformed to compete destabilizer peptide with polyclonal anti-S2 antibody to bind human cardiac myosin S2 peptide and rabbit skeletal myosin S2.

The assay began with coating 96 well microtiter plate with rabbit skeletal myosin molecule overnight. To each of the wells 1:64 diluted primary polyclonal anti-S2 antibody was added followed by 62.5 nM of human cardiac myosin S2. Different concentration of destabilizer peptide in nanomolar units were added to the wells in replicates. After incubation at room temperature for an hour, the unbound protein complexes were washed with PBS and blocking buffer. Enzyme conjugated secondary antibody were added on to the wells and allowed conjugate for an hour at room temperature. After washing the wells with detergent buffer, color developing BCIP substrate were added on to the wells. Images of the color developed in the wells were captured and analyzed in Image J.

The trend in the optical density with different concentration of destabilizer peptide observed was from low OD to high OD to again back to low OD (FIG. 44A). This trend in OD was expected, the wells with no destabilizer peptide, had their primary polyclonal anti-S2 bound to human cardiac myosin S2 peptide and this complex gets washed off, thus there are low amounts of primary antibody left for enzyme conjugate secondary antibody to bind resulting in lower OD.

As the concentration of destabilizer peptide kept on increasing, the destabilizer peptide would bind to human cardiac myosin S2 peptide, resulting in primary polyclonal anti-S2 antibody to go and bind to next available myosin S2 site on rabbit skeletal myosin bound to wells. Thus enzyme conjugate secondary antibody would have primary antibody to bind to resulting in higher OD with increasing concentration of destabilizer peptide.

The drop in OD is observed, because there comes a stage where destabilizer peptide would saturate all the available human cardiac myosin S2 and the leftover destabilizer peptide would go and bind to myosin S2 region in rabbit skeletal myosin bound to the wells of microtiter plate. Primary polyclonal anti-S2 would have less myosin S2 sites available to bind, leading to lower OD upon addition of enzyme conjugate secondary antibody.

This trend in OD thus confirms that destabilizer peptide designed was specific to myosin S2, especially at proximal myosin S2 (924-942), since the destabilizer peptide competed with the binding of polyclonal anti-S2 antibody. The binding efficiency ($K_d$) of destabilizer peptide was calculated to be at 6 nM (FIG. 44B).

FIG. 44A-B illustrates optical Density versus the destabilizer peptide concentration. (A) OD with increasing concentration of stabilizer peptide gave the trend of low-high-low OD. (B) Curve fit of OD with increasing destabilizer concentration to calculate the binding efficiency ($K_d$).

cELISA experiment with destabilizer peptide showed that the destabilizer peptide was specific to myosin S2 also cross specific since it was able to bind to bot human cardiac myosin S2 and rabbit skeletal myosin S2. The destabilizer peptide had more potent and higher binding efficiency to human cardiac myosin S2 compared to rabbit skeletal myosin S2.

Gravitational Force Spectroscopy with Destabilizer Peptide

The destabilizer peptide was specific to myosin S2 region and also cross specific, that it can bind to both human cardiac myosin S2 and rabbit skeletal myosin S2, as shown by cELISA experiment. Next assay performed was to check whether the designed destabilizer peptide can destabilize the myosin S2 coiled coil. GFS with rabbit skeletal myosin treated with destabilizer peptide was performed to confirm the destabilizing effect of destabilizer peptide at myosin S2 coiled coil.

For the GFS assay, the rabbit skeletal myosin molecule was tethered between immobile edge and mobile bead with help of G-actin and myosin S1 binding property of myosin molecule. The edge of the glass coverslips and silica beads were coated with G-actin molecules. The slide for GFS was prepared, with the successful tethering of rabbit skeletal myosin molecule between G-actin coated immobile edge and mobile beads. To test the effect of destabilizer peptide, the rabbit skeletal myosin molecules incubated with destabilizer peptide were tethered similarly as described earlier. GFS measurement were performed to get force distance curves for the uncoiling of myosin molecule without and with destabilizer peptide when pulled from its myosin S1 heads in both the directions perpendicular to its thick filament axis.

From the force distance curve fit of myosin molecule in absence of destabilizer peptide, to uncoil the myosin molecule to a length of 100 nm the force required was $4.92\pm0.11$ pN (n=7) (FIG. 45A, Table 9). In presence of destabilizer peptide, to uncoil the myosin molecule to a length of 100 nm, the force required was $3.09\pm0.05$ pN (n=7) (FIG. 45B, Table 9). The correlation coefficient (R) for control was 0.98 and for test was 0.988. Force distance traces, when compared in absence and presence of destabilizer peptide showed the enhancement of the flexibility of myosin S2 coiled coil with 1.6 times less force required to uncoil the myosin molecule in presence of destabilizer peptide (FIG. 46).

FIG. 45A-B illustrate force distance curve for GFS experiment with rabbit skeletal myosin treated with destabilizer peptide. (A) Force distance curve for uncoiling of myosin molecule with no destabilizer peptide added (n=7). (B) Force distance curve for uncoiling of myosin molecule with destabilizer peptide added (n=7). In dashed box; cartoon of a myosin molecule (red) with destabilizer peptide (orange) tethered at myosin S1 region with actin (cyan arrow) for GFS.

TABLE 9

| Length of uncoiled myosin S2 molecule in absence and presence of MyBPC measured with GFS. | | | |
|---|---|---|---|
| | No. of molecules (n) | Length (nm) | Force (pN) | Correlation coefficient (R) |
| Myosin S2 (Control) | 7 | 100 | $4.92 \pm 0.11$ | 0.980 |
| Myosin S2 with destabilizer peptide (Test) | 7 | 100 | $3.09 \pm 0.05$ | 0.988 |

FIG. 46 illustrates comparison of force distance curve for control (blue) and test (red) assay for myosin molecule treated with destabilizer peptide.

GFS of rabbit skeletal myosin molecule with destabilizer peptide confirmed the destabilizing effect of destabilizer peptide to myosin molecule, since the force required to uncoil the myosin molecule in presence of destabilizer peptide was less when compared to that of the control. cELISA specified the binding of destabilizer peptide to myosin S2, thus destabilization of myosin coiled coil by destabilizer peptide has to be at the myosin S2 region.

Myofibrillar Contractility Assay with Destabilizer Peptide.

GFS and cELISA experiments proved, the specificity of destabilizer peptide to myosin S2 region and destabilization of the same upon binding. To study the effect the destabilization of myosin S2 coiled coil over the contraction in myofibrils, myofibrillar contractility assay was performed in rabbit skeletal myofibrils treated with different concentrations of destabilizer peptide.

For control assay, the rabbit myofibrils were washed thoroughly with assay buffer and small amount of myofibrils are placed on a glass coverslip and imaged through microscope. To the same myofibrils 100 µl of 1 mM ATP diluted in assay buffer was added to allow the shortening of sarcomeres in the myofibrils. Difference in the length of sarcomere before and after addition of ATP gave the percentage of contraction in sarcomeres of myofibril in absence of destabilizer peptide.

For test assay, washed rabbit myofibrils were incubated at room temperature for two hours with different nanomolar concentrations of destabilizer peptide ranging from none to 1000 nM. These destabilizer treated myofibrils were imaged for sarcomeres before and after addition of ATP to calculate percentage contraction in these myofibrils.

With increasing concentration of destabilizer peptide, the percentage contraction in sarcomeres kept on increasing and saturated at concentrations above 40 nM (FIG. 47). The binding efficiency (Kd) of destabilizer peptide to myofibrils was calculated to be less than 10 nM at 7.88 nM (FIG. 47).

FIG. 47 illustrates percentage contraction in sarcomeres versus destabilizer peptide concentration. With increase in destabilizer peptide the percentage contraction in sarcomeres also increased.

Myofibrillar contractility assay with destabilizer peptide confirmed that destabilization of myosin S2 coiled coil by destabilizer peptide resulted in increased contraction in myofibrils treated with destabilizer peptide. In the assay the only factor added to myofibrils was increased dosage of destabilizer peptide, thus stating the direct relation between destabilization of myosin S2 coiled coil and increase in contraction of myofibrils treated with destabilizer peptide.

In Vitro Motility Assay of Actin Thin Filaments Over Myosin HMM Incubated with Destabilizer Peptide.

The cELISA, GFS and myofibrillar contractility assay with destabilizer peptide was able to substantiate that destabilization of myosin S2 coiled coil lead to increased contraction in myofibrils. In vitro motility assay was performed to correlate whether, destabilization of myosin S2 coiled coil also lead to increase in overall force produced through acto-myosin interaction. Increase in the motility of actin thin filaments over myosin molecules treated with destabilizer peptide would confirm that destabilized myosin S2 coiled coil lead to increase in overall force produced through acto-myosin interaction.

In vitro assay began with immobilizing purified myosin HMM on dichloromethylsilane coated glass coverslip. Unlabeled actin thin filament followed by addition of ATP diluted in AB-BSA buffer to the slide allowed the blocking of dead myosin S1 heads. Fluorescently labeled actin thin filaments were added and allowed to conjugate for few minutes over the active myosin S1 heads on the coverslip. ATP diluted in AB-BSA-GOC buffer was added and imaged through ICCD added to the microscope, to capture the movement of actin thin filaments. To the same slide destabilizer peptide and ATP diluted in AB-BSA-GOC buffer was added to image the sliding of actin thin filaments over myosin HMM with destabilizer peptide. In vitro motility assay was performed with 20 nM and 100 nM destabilizer peptide.

The observed motility of actin thin filaments were much faster compared to control irrespective of the concentration of destabilizer peptide. Histogram for motility actin thin filaments in control and test assay with 20 nM and 100 nM destabilizer peptide showed a differential distribution. For control the motility of actin thin filaments were in range of 6.5 microns/second, while test assay with 20 nM and 100 nM had motility in the range of 8.0 microns/second (FIG. 48A). Average velocity of actin thin filaments in control assay was 6.82±0.211 microns/second (n=20), for test assay with 20 nM destabilizer peptide was 8.22±0.254 microns/second (n=22) and test assay with 100 nM destabilizer peptide was 8.39±0.397 microns/second (n=19) (FIG. 48B). The difference in velocities of actin thin filaments in control and test assay with 20 nM destabilizer peptide or control and test assay with 100 nM destabilizer peptide were statistically significant with p values less than 0.05, however the difference of velocities in both the test assay were not statistically significant (Table 10).

FIG. 48 illustrates a histogram for the velocity of actin thin filaments in presence of destabilizer peptide. (A) Histogram for the number of actin thin filaments with their respective velocity, control (blue); velocity of actin in absence of destabilizer peptide, test (red); velocity of actin thin filaments in presence of 20 nM destabilizer peptide and test (green); velocity of actin thin filaments in presence of 100 nM destabilizer peptide. (B) Histogram for the average velocities of actin thin filaments in control (blue) (n=20), test with 20 nM destabilizer peptide (red) (n=22) and test with 100 nM destabilizer peptide (green) (n=19).

TABLE 10

Table for student's t-test to signify the effect of destabilizer peptide over the velocity of actin thin filaments.

| Sample: Velocity of actin filaments | p (T ≤ t) one-tail | p (T ≤ t) two-tail |
|---|---|---|
| Control and 20 nM destabilizer peptide | 0.000101236 | 0.000202472 |
| Control and 100 nM destabilizer peptide | 0.000750204 | 0.001500408 |
| 20 nM destabilizer peptide and 100 nM destabilizer peptide | 0.366973124 | 0.733946248 |

The increased motility of actin thin filaments over myosin HMM treated with destabilize peptide confirmed that destabilization of myosin S2 coiled coil directly influenced the increase in motility of actin thin filaments, thus increasing the overall force produced through acto-myosin interaction. The assay also showed that destabilizer peptide in lower concentration was potent in increasing the motility of actin thin filaments, since five times the lower concentration of destabilizer peptide utilized had no statistically significant difference in their respective velocities.

Conclusion

The destabilizer peptide was designed to destabilize the myosin S2 coiled coil at its proximal region (924-942) and study the implication of this destabilized myosin S2 coiled coil over the contraction of sarcomeres in myofibrils and over all force produced through acto-myosin interaction.

cELISA experiment with destabilizer peptide confirmed the specificity of destabilizer peptide to proximal myosin S2 region. The destabilizer peptide was able to compete with the polyclonal anti-S2 antibody to bind to human cardiac myosin S2 peptide and myosin S2 on rabbit skeletal myosin. cELISA also showed the high binding efficiency of destabilizer peptide to human cardiac myosin S2 peptide with $K_d$ at 1 nM (FIG. 44).

GFS performed with rabbit skeletal myosin treated with destabilizer peptide confirmed the destabilization of myosin coiled coil. The force required to uncoil the myosin molecule with destabilizer peptide was 1.6 times less than the force required to uncoil the myosin molecule with no destabilizer peptide added (FIG. 46). The binding site of destabilizer peptide at proximal myosin S2 is approximately 50 nm away from myosin S1 (Warrick, H. M., and Spudich, J. A. 1987) and the force trace shows the effect of destabilizer peptide to be more apparent after 50 nm.

Myofibrillar contractility assay showed that myofibrils treated with destabilizer peptide had increased contraction when compared to control. Increase in contraction of myofibrils was also observed with increased concentration of destabilizer peptide. The effective concentration of destabilizer peptide was less than 10 nM. The percentage contraction in control was approximately at 18% which rose to a maximum of 43% in presence of destabilizer peptide. Thus confirming that destabilized myosin S2 lead to increase on contraction of sarcomeres in myofibril.

In vitro motility assay also confirmed the effect of destabilized myosin S2 over the force produced through acto-myosin interaction. The velocity of actin thin filaments over myosin molecules treated with destabilizer peptide was higher compared to control. Average velocity of actin thin filaments in control assay was 6.82±0.211 microns/second, for test assay with 20 nM destabilizer peptide was 8.22±0.254 microns/second and test assay with 100 nM destabilizer peptide was 8.39±0.397 microns/second. Thus in vitro motility assay confirmed that increase in force produced through acto-myosin interaction was due to destabilized myosin S2 coiled coil by destabilizer peptide.

All the experiments performed, confirms that a destabilized myosin S2 coiled lead to increase in contraction of sarcomeres and overall force produced through acto-myosin interaction. The destabilization of myosin S2 coiled coil was achieved through binding of destabilizer peptide designed to bind myosin S2 in the proximal region (924-942). Increase in contraction and force produced due to a destabilized myosin S2 coiled coil should be due to increase in the number of active myosin S1 heads ($N_t$) available to bind actin filaments, since the experiments were performed with myosin, myofibril and myosin HMM treated with destabilizer peptide, the only region which would have been affected by destabilizer peptide would be the myosin S2 region, and the effect observed was the destabilization of myosin coiled coil at S2 region. Thus confirming the correlation between destabilized myosin S2 coiled coil and increased contraction of sarcomeres along with the increased force production due to increase in number myosin S1 heads ($N_t$) available.

Specificity of the synthesized peptides binding to myosin in the sarcomere was assessed using super-resolution microscopy with the newly available expansion microscopy technique. Fluorescently labeled synthetic peptides will be incubated with myofibrils and then examined by confocal microscopy and expansion microscopy. The potential impacts of thick filament structure and myosin binding proteins will be also be assessed from the images. See FIGS. 49 and 50 as an example.

FIG. 49 illustrates a super-resolution microscopy of a single sarcomere stained with a fluorescein labeled destabilizer peptide using expansion microscopy and a ZEISS 710™ confocal microscope with a water immersion objective lens. The fluorescent intensity profile indicates the expected dip in intensity at the bare zone (M-disk) of the thick filament, but also noticeable decreases in labeling in the C zone where myosin binding protein C resides. There is negligible labeling of the Z-line and surrounding I band. The pattern is consistent with specific labeling of myosin, but possible competition with other myosin binding proteins may exist.

FIG. 50 illustrates a super-resolution microscopy averaged images of sarcomeres stained with both Stabilizer (A) and Destabilizer (B) illustrating specific labeling of the A band.

We started our series of myofibrillar contractility assays with a control group of myofibrils, running assays without adding chemical modifiers to the myofibrils. Eventually, we reached an average of 15±4 percent contractility for our control group.

Effect of S-2 Modulating Peptides

Performing assays with the unlabeled destabilizing peptide, we confirmed the effectiveness of the peptide in increasing the percentage of myofibril shortening (Table 11). We found that the destabilizing peptide greatly induced contraction more than two-fold compared to our control group at high concentrations.

TABLE 11

| Unlabeled Destabilizer | | | | |
|---|---|---|---|---|
| Concentration (nM) | Before (μm) | After (μm) | % Contraction | # of assays (n) |
| 200 | 2.3 | 1.5 | 35 ± 7% | 5 |
| 80 | 2.3 | 1.5 | 32 ± 4% | 4 |
| 40 | 2.2 | 1.7 | 25 ± 8% | 8 |
| 20 | 2.2 | 1.7 | 21 ± 3% | 6 |
| 0 | 2.2 | 1.8 | 15 ± 4% | 24 |

The FITC (fluorescein isothiocyanate) labeled destabilizing peptide displayed similar effectiveness as the unlabeled destabilizing peptide at higher concentrations (around 200 nM). On the other hand, we concluded the FITC labeled destabilizer decreased in efficacy compared to the unlabeled destabilizer at lower concentrations based on their $EC_{50}$ (Table 12). The half maximal effective concentration ($EC_{50}$), or concentration required to reach 50 percent of the increase in percent contraction caused by the destabilizing peptide, was 8±4 nM in the unlabeled destabilizer and 55±19 nM in the labeled destabilizer. Thus, the labeled destabilizing peptide required a greater concentration to enhance myofibril shortening at lower concentrations than the unlabeled destabilizing peptide.

TABLE 12

| | | | labeled Destabilizer | |
| --- | --- | --- | --- | --- |
| Concentration (nM) | Before (μm) | After (μm) | % Contraction | # of assays (n) |
| 200 | 2.2 | 1.5 | 35 ± 3% | 5 |
| 80 | 2.3 | 1.6 | 31 ± 2% | 5 |
| 40 | 2.1 | 1.4 | 33 ± 4% | 5 |
| 10 | 2.1 | 1.5 | 26 ± 3% | 4 |
| 0 | 2.2 | 1.8 | 15 ± 4% | 24 |

Testing the unlabeled stabilizing peptide, we also confirmed its significant influence on inhibiting myofibril contraction (Table 13). When we tested the TRITC (tetramethylrhodamine) labeled stabilizing peptides, we discovered that the labeled stabilizing peptides performed weaker at lower concentrations than the unlabeled stabilizing peptides based on their half maximal inhibitory concentration ($IC_{50}$). Similar to the $EC_{50}$, the $IC_{50}$ refers to the concentration required to reach 50 percent of the reduction in percent contractility. We recorded $IC_{50}$ values of 12±6 nM for the labeled stabilizer and 68±27 nM for the unlabeled stabilizer.

TABLE 13

| | | | Unlabeled Stabilizer | |
| --- | --- | --- | --- | --- |
| Concentration (nM) | Before (μm) | After (μm) | % Contraction | # of assays (n) |
| 200 | 2.2 | 2.0 | 8 ± 1% | 5 |
| 80 | 2.2 | 2.0 | 9 ± 2% | 4 |
| 40 | 2.2 | 1.9 | 10 ± 1% | 4 |
| 10 | 2.1 | 1.9 | 12 ± 2% | 6 |
| 0 | 2.2 | 1.8 | 15 ± 4% | 24 |

Our data shows that the labeled stabilizer required a greater concentration than the unlabeled stabilizer to reduce contraction at low concentrations (Table 14). Nevertheless, we found both the unlabeled and labeled stabilizing peptides maintained functions of inhibiting myofibril shortening at high concentrations.

TABLE 14

| | | | labeled Stabilizer | |
| --- | --- | --- | --- | --- |
| Concentration (nM) | Before (μm) | After (μm) | % Contraction | # of assays (n) |
| 200 | 2.4 | 2.2 | 9 ± 3% | 4 |
| 80 | 2.2 | 2.0 | 10 ± 2% | 5 |
| 40 | 2.3 | 2.0 | 12 ± 1% | 4 |
| 20 | 2.2 | 1.9 | 14 ± 2% | 4 |
| 0 | 2.2 | 1.8 | 15 ± 4% | 24 |

We determined that both the fluorophore labels on the destabilizing and stabilizing peptides did not impede the peptides' functions on modulating myosin subfragment-2 when they were present in high concentrations. Since fluorophore mass is similar to masses of certain peptide sequences, our results indicate the possibility of adding another peptide to the destabilizing and stabilizing peptides. We could potentially modify the S2 modulating peptides with other peptides proven to aid in cell-penetrating capabilities and cardiac tissue specificity[19]. Furthermore, the destabilizing and stabilizing peptides have been shown to bind with more affinity to cardiac and skeletal myosin on humans than rabbits through competitive ELISA assays (Singh, 2017). We concluded that the peptides' stronger binding to human myosin indicates greater effects in their properties of modulating the myosin subfragment-2 region to influence percent contraction.

FIG. 51 graphically illustrates rabbit myofibrillar contractility assay with destabilizing peptide.

FIG. 52 graphically illustrates rabbit myofibrillar contractility assay with FITC labeled destabilizing peptide.

FIG. 53 graphically illustrates rabbit myofibrillar contractility assay with stabilizing peptide.

FIG. 54 graphically illustrates rabbit myofibrillar contractility assay with TRITC labeled stabilizing peptide.

FIG. 55A illustrates an image of labeled destabilizer before ATP 40 nM, FIG. 55B illustrates an image of labeled Destabilizer after ATP 40 nM, % Contraction: 25%; FIG. 55C illustrates an image of labeled Stabilizer before ATP 40 nM, FIG. 55D illustrates an image of labeled Stabilizer after ATP 40 nM, % Contraction: 13%.

FIG. 56A illustrates an image of unlabeled destabilizer before ATP 40 nM, FIG. 56B illustrates an image of unlabeled Destabilizer after ATP 40 nM, % Contraction: 30%; FIG. 56C illustrates an image of unlabeled stabilizer before ATP 40 nM, FIG. 56D illustrates an image of unlabeled Stabilizer after ATP 40 nM, % Contraction: 11%.

Myosin Head Cooperativity Hypothesis

We obtained previously calculated Kd values, concentrations at which half of myosin is saturated with stabilizing or destabilizing peptides, and compared them to our $EC_{50}$ and $IC_{50}$ values (Table 15). Unsure if the $IC_{50}$ value of the labeled stabilizer was significant to its Kd value (n=3), we performed an unpaired two-tailed t test. Acquiring statistically significant results (P<0.01), we deduced that both values can be treated separate from one another.

TABLE 15

| EC-50 and Kd values for destabilizers (above), IC-50 and Kd values for stabilizers (below). All values are statistically significant. | | |
| --- | --- | --- |
| | EC-50 value | Kd value |
| Labeled Destabilizer | 55 ± 19 nM | 176 ± 26 nM |
| Unlabeled Destabilizer | 8 ± 4 nM | 75 ± 36 nM |
| | IC-50 Value | Kd Value |
| Labeled Destabilizer | 68 ± 27 nM | 330 ± 156 nM |
| Unlabeled Destabilizer | 12 ± 6 nM | 6 ± 2 nM |

Finding the majority of $IC_{50}$ or $EC_{50}$ values of the peptides were lower than their respective Kd values, we realized that those peptides did not need to saturate myosin halfway before they could deliver their effects on modulating percent contractility. The unlabeled stabilizer had an $IC_{50}$ and a Kd value around the same range unlike the other peptides' values. However, we adjusted concentrations of the unlabeled destabilizing and stabilizing peptides from diluted solutions based on calculations of the original stock solution. Due to the phenomenon of peptides adhering to the sides of their solution tube, we expected our calculated concentrations to be slightly higher than actual concentration. Because the peptides did not have fluorophores, we could not measure their concentrations accurately with the UV spectrophotometer. Thus, we assume the unlabeled stabilizer would provide a similar trend in $IC_{50}$ and Kd values to the other peptides' values if measured more accurately in future experiments.

Based on those results, we propose a new hypothesis involving the cooperativity of myosin heads. We predict that once a number of myosin heads are influenced (through the modulation of S2), they cause other myosin heads around them in the thick filament to also become affected in the same way alike a chain-reaction mechanism. As a result, a small dose of S2 modulating peptide will be amplified to cause a greater reaction than suggested by the Kd.

Binding to Myosin S2

Before testing the effect of stability of myosin S2 coiled coil over contraction in myofibrils and force produced. The stability of myosin S2 coiled coil was tested by binding with its natural binding partner myosin binding protein C and two peptides designed to bind myosin S2 them being the stabilizer and destabilizer peptide. Confocal microscopy results of myofibrils treated with fluorescently labelled stabilizer and destabilizer peptide highlighted the A bands of sarcomere in particular with no fluorescence detected in the Z line, which corroborated that the designed peptides were specific to muscle myosin and did not bind non muscle myosin or actin thin filaments (Singh et al., unpublished). Stabilizer and destabilizer peptides was tested by cELISA to verify their binding specificity and efficiency to myosin S2 of muscle myosin. Both the peptides were competed against polyclonal anti-S2 antibody to bind human cardiac myosin S2 and rabbit skeletal myosin S2. cELISA experiment with both the peptides gave the similar trend with the OD observed. The trend was from low OD-high OD-low OD with increasing concentrations of the peptides (FIG. 37A and FIG. 44A).

When there were no peptides added to the wells, the human cardiac myosin S2 peptide would bind most of the primary polyclonal anti-S2 antibody in the wells and get washed away leading to low OD. With increasing amounts of peptides added to the wells, they competed with primary polyclonal anti-S2 antibody to bind to human cardiac myosin S2 peptide, allowing primary polyclonal anti-S2 antibody to bind the myosin S2 on rabbit skeletal myosin adsorbed on the wells resulting in higher OD. After saturation of all the available human cardiac myosin S2 peptide with the designed peptides, the remainder of designed peptides was bound to myosin S2 on rabbit skeletal myosin S2 adsorbed on the wells, causing the OD to decline. This observed trend in OD thus confirmed the specificity of designed peptides to myosin S2. The binding efficiency of stabilizer and destabilizer peptide to human cardiac myosin S2 was at 1 nM, indicating the higher binding efficiency to myosin S2. cELISA also revealed the cross specificity of both the designed peptides to human (3-cardiac myosin S2 and rabbit skeletal myosin S2.

Stability of Myosin S2 Coiled Coil

Gravitational force spectroscopy was performed to test the stability of myosin S2 coiled coil in presence of MyBPC, stabilizer and destabilizer peptide. The spectroscopy studies has shown that myosin S2 is flexible than LMM which behaved like a rigid cylinder (Highsmith et al., 1977). Also electron microscopy studies revealed more bending in the S2 than LMM (Walker et al., 1985). Recently it has been demonstrated that myosin S2 coiled coil is flexible compared to myosin LMM by gravitational force spectroscopy (Singh et al., 2017). Thus the effect of the myosin S2 binding proteins over the stability of myosin S2 coiled coil was measured by gravitational force spectroscopy. Uncoiling of myosin S2 was performed in the absence and presence of myosin S2 binding proteins to reveal their effect over the stability of myosin S2 coiled coil.

Stabilizer peptide added to skeletal myosin molecule also had a stabilizing effect over the myosin coiled coil at myosin S2. The force required to uncoil the myosin coiled coil in presence of stabilizer peptide was one and a half times more than in its absence (FIG. 39). Stabilizer peptide being specific to myosin S2, the binding property of myosin S1 to actin was used to uncoil the myosin molecule in GFS. The force required to uncoil myosin molecule at its myosin S1 end or at myosin S2 region specific to polyclonal anti-S2 are similar (Singh et al., 2017). Thus the binding of stabilizer peptide to myosin molecule stabilizes the coiled coil at myosin S2 region.

In contrast the other designed peptide; destabilizer enhanced the flexibility of myosin coiled coil at myosin S2. The force required to uncoil the myosin coiled coil in presence of destabilizer peptide was 1.6 times less than in its absence (FIG. 46). Destabilizer peptide being specific to myosin S2 the enhanced flexibility of myosin coiled coil observed was localized at myosin S2 region.

GFS performed on whole length skeletal myosin in presence of MyBPC, stabilizer and destabilizer peptide, showed that coiled coil at myosin S2 was stabilized by MyBPC and stabilizer peptide and destabilized or enhanced flexibility by destabilizer peptide. The specific binding of MyBPC, stabilizer and destabilizer peptide to myosin S2 altered the stability of myosin S2 coiled coil.

Sarcomere Shortening of Myofibril

The altered stability of myosin S2 coiled coil upon binding of myosin S2 binding proteins and its effect over sarcomere shortening was assayed with myofibrillar contractility assay. Sarcomere shortening was measured before and after addition of ATP to skeletal myofibrils treated with myosin S2 binding proteins. The stability of myosin S2 by MyBPC and its effect on sarcomere shortening was not performed since the myofibrils had its naturally available MyBPC.

Stabilizer peptide treated myofibrils underwent reduced shortening of sarcomeres on addition of ATP. The sarcomere shortening dropped from 22% contractility to 18% in presence of stabilizer peptide. The binding efficiency of stabilizer peptide to myofibrils was at 6 nM (FIG. 40). This assay thus revealed that stability of myosin S2 by stabilizer peptide reduced the shortening of sarcomeres compared to control. This reduction in shortening of sarcomeres by a stable myosin S2 coiled coil further supports the idea that a stable myosin S2 would reduce or regulate the amount of myosin S1 heads available to bind actin thin filaments.

Destabilizer peptide treated myofibrils showed increase in shortening of sarcomeres. The percentage contraction in myofibrils rose from 22% to a maximum of 41% in presence of destabilizer peptide upon addition of ATP. The binding efficiency of destabilizer peptide to myofibrils was at 7.8 nM (FIG. 47). Destabilizer peptide enhances the flexibility of myosin S2 coiled coil. This enhanced flexibility of myosin S2 resulted in increased contraction in myofibrils thus corroborates the idea that an unstable myosin S2 coiled coil would allow more myosin S1 heads to be available to bind actin thin filaments.

In Vitro Motility of Actin Filaments

In vitro motility of actin filaments over myosin molecule or myosin thick filament treated with myosin S2 binding proteins was performed to test the effect of altered stability of myosin S2 coiled coil over the motility of actin thin filaments. The motility of actin thin filaments over skeletal myosin thick filaments treated with whole length skeletal MyBPC was reduced compared to control. The motility of actin thin filaments was reduced by 22% in presence of MyBPC. This reduction in the motility of actin thin filaments by MyBPC would be either by binding of MyBPC to actin or the myosin S2 depending on the phosphorylation of MyBPC. MyBPC in its unphosphorylated state in a mouse model had impaired contractile function, thus suggesting that phosphorylation is required for maximal crossbridge attachment (Colson et al., 2008; Mamidi et al., 2016). MyBPC used was in its unphosphorylated state depending on the higher pI of MyBPC at 5.3. Also, MyBPC phosphorylation does not affect the $K_d$ of MyBPC for actin, however phosphorylation has been reported to reduce the $B_{max}$ (Weith et al., 2012; Rybakova et al., 2011; Shafer et al., 2009). Thus stating that reduced motility of actin is due to binding of unphosphorylated MyBPC to myosin thick filaments.

The motility of actin thin filaments over myosin molecules treated with stabilizer peptide was reduced by 14% (FIG. 41). Stabilizer peptide enhances the stability of myosin S2 which in turn reduced the motility of actin filaments thus providing the evidence that a stabilized myosin S2 coiled coil regulates the myosin S1 heads available to bind actin. In contrast, the motility of actin thin filaments rose by 18% over myosin molecules treated with destabilizer peptide (FIG. 48). Destabilizer peptide enhances the flexibility of myosin S2 coiled coil, this increased flexibility resulted in increased motility of actin filaments, thus confirming that a destabilized myosin S2 coiled coil increased the number of myosin S1 heads to bind actin, hence the observed increased motility in actin filaments.

Conclusions

In conclusion, the stability of myosin S2 coiled coil could be altered. This altered stability had an effect over the sarcomere shortening in myofibrils and the force required to slide the actin filaments over myosin.

Gravitational force spectroscopy experiments showed that the stability of myosin S2 coiled coil could be altered, MyBPC and stabilizer peptide enhanced the stability of myosin S2 coiled coil, and on the other hand destabilizer peptide decreased the stability and enhanced the flexibility of myosin S2 coiled coil. More the force required to uncoil the myosin coiled coil more stable the myosin coiled coil and vice versa, in presence of myosin S2 binding proteins. GFS allowed the uncoiling of myosin S2 region on myosin coiled coil depending on the point of attachment for myosin molecule to be tethered.

Furthermore, myofibrillar contractility assay with stabilizer and destabilizer peptide myofibrils showed that sarcomere shortening or percentage contractility decreased and increased respectively. Thus connecting the stability of myosin S2 coiled coil to sarcomere shortening. Since the GFS experiments with stabilizer peptide conveyed the enhanced stability to myosin S2 coiled coil, thus the stable myosin S2 coiled coil would be thought to reduce the sarcomere shortening of myofibrils treated with stabilizer peptide. Also the stabilizer peptide being highly specific to muscle myosin S2, thus reduced shortening observed is due to enhanced stability of myosin S2 coiled coil by stabilizer peptide. In contrast, the destabilizer peptide enhanced the flexibility of myosin S2 as observed in GFS experiments, with increased amount of sarcomere shortening in myofibrils treated with destabilizer peptide. Destabilizer peptide being specific to myosin S2, confirmed a destabilized myosin S2 coiled coil increased amount of contraction or sarcomere shortening in myofibrils.

In vitro motility of actin thin filaments over myosin treated with MyBPC, stabilizer and destabilizer peptide gave another line of evidence for the effect of stable or unstable myosin S2 coiled coil over the amount of force produced through acto-myosin interaction to slide the actin filaments. MyBPC and stabilizer peptide shown to stabilize the myosin S2 coiled coil lowered or reduced the sliding velocity of actin filaments, while the enhanced flexibility of myosin S2 coiled coil by destabilizer peptide increased the motility of actin filaments. Thus experiments performed in this study establishes that stability of myosin S2 coiled coil affects the contraction in myofibrils and amount of force produced through acto-myosin interaction. MyBPC and stabilizer peptide enhanced the stability of myosin S2 coiled coil resulting in declined contractility in myofibrils and velocity of actin filaments. Destabilizer peptide decreased the stability of myosin S2 coiled coil resulted in enhanced contractility in myofibrils and velocity of actin filaments. Another conclusion which could be drawn is that the stability of myosin S2 coiled coil could easily be altered by small peptides.

Myosin S2 coiled coil has known to be more flexible than LMM, based on the proteolysis of myosin S2 giving a long and a short S2 fragments while LMM had constant sized fragments (Sutoh et al., 1978). The spectroscopic measurements made showed that LMM was more like a rigid cylinder and myosin S2 was more flexible (Highsmith et al., 1977). Electron microscopy showed more bending at the myosin S2 compared to LMM (Walker et al., 1985). Force spectroscopy data also showed that myosin S2 region being more flexible to LMM, along with the flexibility of myosin S2 region in a myosin molecule was independent of its association in myosin thick filament (Singh et al., 2017). Also the data suggested that myosin S2 is more flexible at its N terminal position, which lines with the data observed in scallop myosin S2 had an unstable N terminal position (Li et al., 2003). While the flexibility of the N terminal coiled coil are thought to increase the step size of some nonmuscle myosins (Rock et al., 2005). Variable myosin head positions observed by electron microscopy in vertebrate striated muscle may be due to this unstable N-terminal coiled coil. Thus the effect of stable or unstable myosin S2 coiled coil observed over myofibrillar contraction and force generated through acto-myosin interaction could be explained by the number of myosin S1 heads ($N_t$) being available to bind actin. A stable myosin S2 would reduce the myosin S1 heads available to bind actin and vice versa with an unstable myosin coiled coil.

FIG. 57 schematically illustrates the effect of myosin S2 binding proteins on myosin S2 coiled coil.

Myosin molecule (red) stabilized by MyBPC (green line) and stabilizer peptide (green L shaped) and destabilized by destabilizer peptide (orange).

Cryo-electron micrograph has shown that invertebrate skeletal myosin have their myosin S1 heads folding back on to its myosin S2 backbone (Woodhead et al., 2005; Alamo et al., 2008; Pinto et al., 2012). Molecular construct of myosin S1 and S2 and MyBPC have shown that N-terminal region of myosin S2 is required to bind myosin Si heads along with MyBPC (Nag et al., 2017). Thus myosin S2 coiled coil structure would be assumed to regulate the availability of myosin S1 heads by its altered stability. Stable myosin S2 coiled coil could provide conformation for myosin S1 heads to fold back and rest on to the myosin S2 coiled coil, while a much more flexible myosin S2 coiled coil won't have conformation for myosin heads to fold back and would allow these myosin S1 heads to be available (FIG. 49).

The effect of stable myosin S2 over force generation has been demonstrated by utilization of antibody against the whole myosin S2, which would likely reduce the flexibility of the same, inhibited the force generation in skinned muscle fibers (Sugi et al., 1992). Similarly MyBPC used in this study, stabilized the myosin S2 coiled coil and it reduced the motility of actin thin filaments. MyBPC molecule along its length binds from LMM to myosin S2 region of myosin molecule. MyBPC bound myosin thick filament reduced the motility of actin thin filaments and MyBPC enhanced the stability of myosin S2 coiled coil thus it would be a reasonable statement that a stable myosin S2 reduced the acto-myosin interaction. Also MyBPC used was in its unphosphorylated state and known to bind myosin S2 rather than actin, thus reduced acto-myosin interaction observed was due to the binding of MyBPC to myosin and not to actin filaments (Colson et al., 2008; Mamidi et al., 2016; Saber et al., 2008). MyBPC binding does not affect the myosin S1 region, the only region affected is the myosin S2 coiled coil, and thus a stable myosin S2 reduced the amount of myosin S1 heads available to bind actin filaments in in vitro motility assay.

The effect of stabilizer peptide was similar to that of MyBPC over the stability of myosin S2 coiled coil. Stabilizer peptide was specific and had a higher binding efficiency to myosin S2 region. It enhanced the stability of myosin S2 coiled coil, also resulted in reduced sarcomere shortening and reduced acto-myosin interaction. Again a stable myosin S2 coiled coil was able to affect and reduce the contraction in myofibrils and motility of actin filaments. Stabilizer peptide used was specific to myosin S2 and would not bind actin as observed through confocal microscopy, also if it had non-specific binding to myosin S1 heads there would have been a drastic change to contractility of myofibrils, also would have hindered with attachment of myosin molecule to actin coated edge and silica bead, in GFS, where the myosin molecules were uncoiled from it myosin S1 heads. The results with stabilizer peptide again gave the conclusive interpretation that a stable myosin S2 coiled coil would reduce the amount myosin S1 heads available to bind actin thus decline in sarcomere shortening and acto-myosin interaction.

Unlike MyBPC and stabilizer peptide, the destabilizer peptide enhanced the flexibility of myosin S2 coiled coil. Previously, the melting of myosin S2 coiled coil by laser temperature jump, accelerated the actin sliding in in vitro motility assay and enhanced the contractility of muscle fibers (Davis, J. S., and Harrington, W. F. 1998; Kato et al., 1999). In this study, with enhanced flexibility of myosin S2 coiled coil the contraction in myofibrils and acto-myosin interaction were enhanced. Like stabilizer peptide the destabilizer peptide was also specific to myosin S2 region. Thus a more flexible myosin S2 coiled coil was able to contribute more myosin S1 heads available to bind actin, hence the observed increment in contractility of myofibrils and acto-myosin interaction.

This study thus supports a function for myosin S2 coiled coil and its role in contraction of striated muscles. The stability or flexibility of myosin S2 coiled coil have opposite effects on the contraction of skeletal muscle. A stable myosin S2 coiled coil decreases and a flexible myosin S2 coiled coil increases the amount of contraction. These results add to the significance of myosin S2 region and explain why mutations in the same region would cause lethal cardiomyopathies. Also, this study highlights the effect of MyBPC binding to myosin S2 coiled coil structure. This could explain the hypercontraction observed in cardiac myofibrils of FHC heart caused by mutation in MyBPC (Adhikari et al., 2016). Mutated MyBPC would result in declined stable myosin S2 and increased flexibility of myosin S2 coiled coil thus allowing more myosin S1 heads available leading to hypercontraction.

Folding back of myosin Si heads on a stable myosin S2 coiled coil, could be tested by creating the crystal structure of a stable myosin S2 with stabilizer peptide and observe the orientation of myosin S1 heads on myosin S2. Electron microscopy images of myosin thick filaments treated with stabilizer peptide could also reveal the orientation of myosin S1 heads upon stabilized myosin S2 coiled coil. The other reason which could be thought would be the restriction of rotation of leaver arm of myosin by a stable myosin S2 coiled coil and free rotation of lever arm of myosin by a flexible myosin S2.

Here we tested the effect of stability of myosin S2 coiled coil over muscle contraction in skeletal form, however, these tests should also be performed with cardiac and smooth muscle type to better understand the effect of myosin S2 coiled coil on all muscle types. Stabilizer and destabilizer peptides were designed to be used as potential drugs to reverse the effects caused by increased or decreased contraction in cardiac myocytes of FHC or DCM heart respectively. These peptides needs to be tested with animal models of cardiomyopathy mutants and whether they are effective with expected result for stabilizer peptide to control the increased contraction and destabilizer peptide to increase the decreased contraction in mutant cardiac myocytes. These peptides could have a potential application to regulate cardiac arrhythmias and an alternative to traditionally used beta blockers.

Another probable application of this study would be to develop drugs to target the stability of myosin S2 coiled coil to regulate the contraction of muscles. Drugs designed to affect the stability of the myosin S2 coiled coil, would not affect the ATPase activity nor the actin binding of myosin S1 directly, but would modulate the number of myosin S1 heads binding actin, even with the affected myosin S1 heads due to mutations in myosin S1 heads. R403Q mutation in myosin S1 heads at the actin binding region, resulted in disarrayed acto-myosin interaction also had faster rates of cross-bridge relaxation (Volkmann et al., 1997; Witjas-Paalberends et al., 2014; Nag et al., 2015). In contrast another FHC mutation R453C increases the ensemble force by increased binding to actin which could be the reason for hyper contractility in FHC hearts (Sommese et al., 2013). Altering the stability of myosin S2 coiled coil of R403Q or R453C mutant cardiac myosin can increase or decrease the myosin S1 heads, since R403Q mutation decreases the acto-myosin interaction increasing number of myosin S1 heads would be helpful and increased myosin S1 heads binding to actin by R453C mutation could be regulated by decreasing the myosin S1 heads. Thus myosin S2 region can be altered to change the cross bridge kinetics and could be used as a therapeutic target for muscles with defects in cross bridge formation.

Example 2: Testing the Exemplary Peptides Modified for Heart Tissue Targeting in Collaboration with Institutions Outside the University of North Texas, Including in Live Mice This example describes and demonstrates that methods and peptide compositions as provided herein when modified with a targeting agent can reach heart tissue and penetrate the cardiomyocyte membrane and effect the predicted response even when administered to live animals.

Tests in Live Mouse Cardiomyocytes

To visualize via fluorescence the penetration of the cardiomyocyte membrane by the peptides, Destabilizer peptides were conjugated on their amino terminus with fluorescein isothiocyanate, as described in Example 1, and modified with a heart targeting moiety by TANNylation as described by for example: Qadan, 2021; Shin et al., 2018; United States Patent Application 20200108149. The TANNylated peptides were found to retain similar myosin binding and effects on contractility to the unmodified peptides (Qadan, 2021). These TANNylated fluorescent Destabilizer peptides (0.055 mM) were shipped to Dr. Kerry McDonald at the University of Missouri who incubated the peptides at 0.001 mM concentration with primary cultures of live mouse cardiomyocytes. Confocal imaging indicated that the fluorescent peptides entered the cardiomyocytes and reached an intracellular fluorescent intensity equal to that of the extracellular intensity at approximately 15 minutes of incubation.

TANNylated Destabilizer peptide without fluorescent labeling (0.055 mM) were also shipped to Dr. Kerry McDonald at the University of Missouri who incubated the peptides at 0.001 mM concentration with primary cultures of live mouse cardiomyocytes that were contracting at 1 second intervals due to electrical stimulations. The extent of shortening increased during the incubation to 3 times that of the control cardiomyocytes. The maximum sarcomere length remained relatively constant at 1,750 nm while the minimum sarcomere length in the presence of destabilizer peptide was reduced to 1,500 nm.

Tests in Live Mice

TANNylated Stabilizer and Destabilizer peptides were prepared and shipped to Dr. Kenneth Campbell at the University of Kentucky for injection into live mice. Dr. Campbell's lab was blinded to the identity of each of the peptides and the targeting molecule alone as a control. FIG. 58 demonstrates the response of echocardiogram measurements of stroke volume in the live mice to the Stabilizer peptide.

FIG. 58 graphically illustrates the kinetics of stroke volume response to TANNylated Stabilizer peptide injection in mouse. Data are normalized to the preinjection stroke volume. Each mouse was injected with 200 nanomoles of Stabilizer peptide. The slow response time likely reflects the time required for the TANNylated peptide to migrate from the extracellular matrix to the sarcoplasm of the cardiomyocyte. Other targeting molecules are expected to produce different response times.

The fluorescent Destabilizer also produced a strong response in both the stroke volume and cardiac output as illustrated in FIG. 59. The Stabilizer peptide appeared to trigger a baroreceptor response that significantly increased heart rate, thus partially negating the effect of decreases stroke volume on cardiac output. The fluorescent Destabilizer peptide increased stroke volume, heart rate, and cardiac output.

FIG. 59 graphically illustrates the response of the TANNylated fluorescent Destabilizer peptide compared to that of the TANNylated Stabilizer peptide at 24 hours postinjection. SV is stroke volume in microliters. HR/10 is the heart rate divided by 10 in beats per minute. CO x2 is the cardiac output multiplied by 2 in milliliters per minute.

The robust response of the fluorescent destabilizer in this experiment is complimented by examination of the heart by cryostat sectioning and confocal microscopy of the heart after its excision at 24 hours postinjection and shipment to the University of North Texas. The fluorescent Destabilizer peptide was well distributed throughout the chamber walls of the heart (FIG. 60). The fluorescent Destabilizer peptide appeared to label the A bands of the sarcomeres as expected (FIGS. 61-65); although a substantial amount of the fluorescent peptide was also observed at various extracellular locations. The sarcomeres are highly shortened in these images which is not inconsistent with the impact of the Destabilizer peptide on increasing the extent of sarcomere shortening. Hyperspectral imaging emission spectra indicate a close match with that of fluorescein in the fluorescent peptide (FIG. 66) confirming the presence of the peptide.

FIG. 60 illustrates an image of a central cryostat section of heart from mouse 24 hours postinjection of the TANNylated fluorescent peptide and imaged by epifluorescence microscopy. LA is the left atrium. RA is the right atrium. LV is the left ventricle. RV is the right ventricle. S is the interventricular septum. A is the apex. The image height is 8.8 mm.

FIG. 61 illustrates an image of: confocal two color image of mouse heart cryostat section. Green is the fluorescent peptide. Blue is the DAPI counterstain for the nuclei. Striations indicating sarcomeric labeling are occasionally resolved. Images were acquire with a 20×, 0.8 NA planapochromat objective lens on a Yokogawa spinning disk confocal microscope. The image dimensions are 0.21 mm×0.21 mm.

FIG. 62 illustrates an image of: a confocal image of mouse heart cryostat section in the fluorescein channel. Striations indicating sarcomeric labeling are occasionally resolved. Images were acquire with a 20×, 0.8 NA planapochromat objective lens on a Yokogawa spinning disk confocal microscope. The image dimensions are 0.11 mm×0.11 mm.

FIG. 63 illustrates an image of: corresponding differential interference contrast image to FIG. 62. Striations indicating sarcomeres are occasionally resolved. Images were acquire with a 20×, 0.8 NA planapochromat objective lens on a ZEISS AXIOVERT™ microscope. The image dimensions are 0.11 mm×0.11 mm.

FIG. 64 illustrates an image of: a super-resolution ZEISS AIRYSCAN™ confocal image of mouse heart cryostat section. Striations indicating sarcomeric labeling are occasionally resolved. Images were acquire with a 63×, 1.4 NA oil planapochromat objective lens on a ZEISS 710 AIRY-SCAN™ confocal microscope. The image dimensions are 0.044 mm×0.044 mm.

FIG. 65 illustrates an image of: a super-resolution ZEISS AIRYSCAN™ confocal 3D projection of a mouse heart cryostat section. Striations indicating sarcomeric labeling are occasionally resolved. Images were acquire with a 40×, 1.2 NA water c-apochromat objective lens on a ZEISS 710 AIRYSCAN™ confocal microscope. The image dimensions are 0.027 mm×0.027 mm×0.017 mm.

FIG. 66 graphically illustrates hyperspectral imaging emission spectrum confocal image of mouse heart cryostat section (black) compared to stock fluorescein emission spectrum (green). The match between the emission spectra indicate that the observed fluorescence is predominantly that from the fluorescent Destabilizer peptide. Images were acquire with a 63×, 1.4 NA oil planapochromat objective lens on a ZEISS 710 AIRYSCAN™ confocal microscope.

The images of heart sections from mice injected with the fluorescent Destabilizer peptide demonstrate that it is possible to deliver the peptides to the heart and to the sarcomeres within the cardiomyocytes. Furthermore, the data echocardiograms are consistent with the fluorescent Destabilizer peptide increasing the stroke volume and the Stabilizer peptide decreasing the stroke volume. Mutations that cause hypertrophic or dilated cardiomyopathies can have similar impacts on the stroke volume as these peptides which may contribute to heart remodeling observed in these diseases. The administration of a peptide with an opposing effect to the genetic mutation would offset the impact of the mutation and ameliorate the pathogenicity.

REFERENCES

Aboonasrshiraz, Negar (published, or first available to public, Sep. 7, 2020) Impact of Anti-S2 Peptides on a Variety of Muscle Myosin S2 Isoforms and Hypertrophic Cardio-myopathy Mutants Revealed by Fluorescence Resonance Energy Transfer and Gravitational Force Spectroscopy, dissertation under Dr. Douglas Root.

Adhikari, A. S., et al. (2016) Early-onset hypertrophic cardiomyopathy mutations significantly increase the velocity, force, and actin-activated ATPase activity of human β-cardiac myosin. *Cell Rep.* 17, 2857-2864.

Alamo, L., et al. (2008) Three-dimensional reconstruction of tarantula myosin filaments suggests how phosphorylation may regulate myosin activity. *J Mol Biol.* 384, 780-797.

Al-Khayat, H A. (2013) Three-dimensional structure of the human myosin thick filament: clinical implications. *Glob. Cardiol. Sci. Pract.* 3, 280-302.

Beckett, E. B. (1963) Histochemistry of cardiac muscle. *Biochem Clin.* 2, 51-60.

Campbell, K. S., et al. (2018) Force-Dependent Recruitment from the Myosin Off State Contributes to Length-Dependent Activation. Biophys. J. 115(3):543-553.

Challice, C. E. and Viragh, S. (1973) Ultrastructure of the Mammalian Heart. p 2-p 36. Academic Press, INC., New York.

Cho, K. W., Lee, J., and Kim, Y. (2016) Genetic variations leading to familial dilated cardiomyopathy. *Mol Cells.* 39, 722-727.

Choudhry, S., Puri, K., and Denfield, S. W. (2019) An Update on Pediatric Cardiomyopathy. Curr. Treat. Options Cardiovasc. Med. 21(8):36.

Colson, B. A., et al. (2008) Protein kinase A-mediated phosphorylation of cMyBP-C increases proximity of myosin heads to actin in resting myocardium. *Circ Res.* 103, 244-251.

Cooke, P. (1976) A filamentous cytoskeleton in vertebrate smooth muscle fibers, *J. Cell Biol.* 68, 539-556.

Davis, J. S., and Harrington, W. F. (1998) Force generation by muscle fibers in rigor: a laser temperature-jump study. *Proc Natl Acad Sci USA.* 84, 975-979.

de Tombe, P. P., et al. (2010). Myofilament length dependent activation. *J. Mol. Cell. Cardiol.* 48, 851-858.

Dunn, J. W., Root, D. D. (2011) Demonstrating the uses of the novel gravitational force spectrometer to stretch and measure fibrous proteins. *J. Visualized Exp.* 49, 2624.

Duong, A. M., Reisler, E. (1989) Binding of myosin to actin in myofibrils during ATP hydrolysis. *Biochemistry* 28(3): 1307-13.

Ebashi, S., Endo, M. and Ohtsuki, I. (1969) Control of Muscle Contraction. *Q. Rev. Biophys.* 2, 351-384.

Elliott, A., and Offer, G. (1978) Shape and flexibility of the myosin molecule. *J. Mol. Biol.* 123, 505-519.

Erdmann, J., et al. (2003) Mutation spectrum in a large cohort of unrelated consecutive patients with hypertrophic cardiomyopathy. *Clin. Genet.* 64, 339-349.

Förster, T. (1948) Zwischenmolekulare energiwanderung und fluoreszence (Intermolecular energy migration and fluorescence), *Annals of Physics,* 2, 55-75.

Frederiksen, D. W., and Cunningham, L. W. (1982) The Contractile Apparatus and the Cytoskeleton. *Methods in Enzymology* 85 Part B, Academic Press, New York.

Fürst, D. O., et al. (1992) Mammalian skeletal muscle C-protein: purification from bovine muscle, binding to titin and the characterization of a full-length human cDNA. *J. Cell Sci.* 102, 769-778

Fusi, L., et al. (2016) Thick filament mechano-sensing is a calcium-independent regulatory mechanism in skeletal muscle. *Nat. Commun.* 7, 13281.

Gautel, M., et al. (1995) Phosphorylation switches specific for the cardiac isoform of myosin binding protein-C: a modulator of cardiac contraction? *EMBO J.* 14, 1952-1960.

Godfrey, J. E., and Harrington, W. F. (1970) Self-association in the myosin system at high ionic strength. I. Sensitivity of the interaction to pH and ionic environment. *Biochemistry* 9, 886-895.

Goldman, Y. E. (1987) Kinetics of the actomyosin ATPase in muscle fibers. *Annu. Rev. Physiol.* 49, 637-654.

Goodson, H. V. and Spudich, J. A. (1993) Molecular evolution of the myosin family: Relationships derived from comparisons of amino acid sequences. *Proc. Natl. Acad. Sci. U.S.A.* 90, 659-663.

Gordon, A. M., et al. (2000). Regulation of contraction in striated muscle. *Physiol. Rev.* 80, 853-924

Greaser, M. L. and Gergely, J. (1971) Reconstitution of troponin activity from three protein components. *J. Biol. Chem.* 246, 4226-4233.

Gruen, M., and Gautel M. (1999) Mutations in beta-myosin S2 that cause familial hypertrophic cardiomyopathy (FHC) abolish the interaction with the regulatory domain of myosin-binding protein-C. *J Mol Biol.* 286, 933-949.

Highsmith, S. (1977) The effects of temperature and salts on myosin subfragment-1 and F-actin association. *Arch. Biochem. Biophys.* 180, 404-408.

Holmes, K. C., Popp, D., Gebhard, W. and Kabsch, W. (1990) Atomic model of the actin filament. *Nature* 347, 44-49.

Huxley, A. F. (1964) *Muscle. Annu. Rev. Physiol.* 26, 131-152.

Huxley, A. F. and Niedergerke, R. (1954) Structural changes in muscle during contraction; Interference microscopy of living muscle fibres. *Nature* 173, 971-973.

Jean, M. (2003) How to subdue a swelling heart. *Science.* 300, 1492-1496.

Jeffries, C. M., et al. (2011) Human cardiac myosin binding protein C: structural flexibility within an extended modular architecture. *J. Mol. Biol.* 414, 735-748.

Kato, H., et al. (1999) Imaging of thermal activation of actomyosin motors. *Proc Natl Acad Sci USA.* 96, 9602-9606.

Kensler, R. W., Craig, R., and Moss, R. L. (2017) Phosphorylation of cardiac myosin binding protein C releases myosin heads from the surface of cardiac thick filaments. *Proc. Natl. Acad. Sci. U.S.A.* 114, 1355-1364.

Kinosita, K. Jr., et al. (1984) Submicrosecond and microsecond rotational motions of myosin head in solution and in myosin synthetic filaments as revealed by time-resolved optical anisotropy decay measurements. *Biochemistry* 23, 5963-5975.

Kooij, V., et al. (2013) Characterization of the cardiac myosin binding protein-C phosphoproteome in healthy and failing human hearts. *J. Mol. Cell. Cardiol.* 60, 116-120.

Kron, S. J., et al. (1991) Assays for actin sliding movement over myosin-coated surfaces. *Methods Enzymol.* 196, 399-446.

Levine, R., et al. (2001) Multiple structures of thick filaments in resting cardiac muscle and their influence on cross-bridge interactions. *Biophys J.* 81, 1070-1082.

Li, Y., et al. (2003) Visualization of an unstable coiled coil from the scallop myosin rod. *Nature* 424, 341-345.

Lymn, R. W. and Taylor, E. W. (1971) Mechanism of adenosine triphosphate hydrolysis by actomyosin. *Biochemistry* 10, 4617-4624.

Maliwal, B. P., et al. (1994) Fluorescence energy transfer in one dimension: Frequency-domain fluorescence study of DNA-fluorophore complexes. Biopolymers, 35, pp. 245-255.

Mamidi, R., et al. (2016) Cardiac myosin binding protein-C phosphorylation modulates myofilament length-dependent activation. *Front Physiol.* 7, 38.

McNally, E. M., et al. (2015) The genetic landscape of cardiomyopathy and its role in heart failure. *Cell Metab.* 21, 174-82.

Miller, J. D., Yousuf, O., and Berger, R. D. (2015) The implantable cardioverter-defibrillator: An update. *Trends Cardiovasc. Med.* 25(7):606-11.

Moos, C., Offer, G., Starr, R., and Bennett, P. (1975) Interaction of C-protein with myosin, myosin rod and light meromyosin. *J Mol. Biol.* 97, 1-9.

Muir, A. R. (1965) Further observations on the cellular structure of cardiac muscle. *J Anat.* 99, 27-46.

Mun, J. Y., et al. (2011) Electron microscopy and 3D reconstruction of F-actin decorated with cardiac myosin-binding protein C (cMyBP-C). *J. Mol. Biol.* 410, 214-25.

Mun, J. Y., et al. (2014) Myosin-binding protein C displaces tropomyosin to activate cardiac thin filaments and governs their speed by an independent mechanism. *Proc. Natl. Acad. Sci. U.S.A.* 111, 2170-2175.

Nag, S., et al. (2015) Contractility parameters of human β-cardiac myosin with the hypertrophic cardiomyopathy mutation R403Q show loss of motor function. *Sci Adv.* 1. Online.

Nag, S., et al. (2017) The myosin mesa and the basis of hypercontractility caused by hypertrophic cardiomyopathy mutations. *Nat Struct Mol Biol. Online.*

Ochsnaer, M. (1997) Ca2+ transient, cell volume, and microviscosity of the plasma membrane in smooth muscle. *Biochem. Pharmacol.* 53, 1765-1777.

Offer G, Moos C, and Starr R. (1973) A new protein of the thick filaments of vertebrate skeletal myofibrils: extraction, purification and characterisation. *J Mol Biol.* 74, 653-676.

Pinto, A., et al. (2012) The myosin interacting-heads motif is present in the relaxed thick filament of the striated muscle of scorpion. *J Struct Biol.* 180, 469-478.

Previs, M. J., et al. (2016) Phosphorylation and calcium antagonistically tune myosin-binding protein C's structure and function. *Proc. Natl. Acad. Sci. U.S.A.* 113, 3239-3244.

Previs, M. J., et al. (2012) Molecular mechanics of cardiac myosin binding protein-C in native thick filaments. *Science* 337, 1215-1218.

Price, H. M. (1963) The skeletal muscle fiber in the light of electron microscope studies. A review. *Am J Med.* 35, 589-605.

Qadan, M. (not published) "The Development of potential therapeutic anti-myosin S2 peptides that modulate contraction and append to the heart homing adduct "tannic acid" without noticeable effect on their functions." University of North Texas. (Dissertation under Dr. Root)

Rayment, I., and Holden, H. M. (1994) The three-dimensional structure of a molecular motor. *Trends Biochem Sci.* 19, 129-34.

Rayment, I., Smith, C., and Yount, R. G. (1996) The active site of myosin. *Annu. Rev. Physiol.* 58, 671-702.

Reed, B. N., Sueta, C. A. (2015) A practical guide for the treatment of symptomatic heart failure with reduced ejection fraction (HFrEF). Curr. Cardiol. Rev. 11(1):23-32.

Rees, M. K., and Young, M. (1967) Studies on the isolation and molecular properties of homogeneous globular actin. Evidence for a single polypeptide chain structure. *J. Biol. Chem.* 242, 4449-4458.

Resiler, E., Cheung, P., and Borochov, N. (1986) Macromolecular assemblies of myosin. *Biophys. J* 49, 335-342.

Richard, P., et al. (2003) Hypertrophic cardiomyopathy: distribution of disease genes, spectrum of mutations, and implications for a molecular diagnosis strategy. *Circulation* 107, 2227-2232.

Rickenbacher, P. (2011) Drug treatment for chronic heart failure with reduced ejection fraction. Ther. Umsch. 68(2):71-9.

Robyt, J. F., and White, B. J. (1987) "Biochemical techniques: Theory and practice" Brooks/Cole Pub. Co., Florence, Kentucky.

Rock, R. S., et al. (2005) A flexible domain is essential for the large step size and processivity of myosin VI. *Mol Cell.* 17, 603-609.

Roger V, Go A, Lloyd-Jones D, Benjamin E, et al. (2012) Heart Disease and Stroke Statistics-2012 Update. Circ. 2012; 125(1): e2-e220.

Root D D, Shangguan X, Xu J, McAllister M A. (1999) Determination of fluorescent probe orientations on biomolecules by conformational searching: algorithm testing and applications to the atomic model of myosin. Journal of Structural Biology 127(1):22-34.

Root, D. D., and Reisler, E. (1992) Cooperativity of thiol-modified myosin filaments. ATPase and motility assays of myosin function. *Biophys. J.* 63, 730-740.

Ruppel, K. M., and Spudich, J. A. (1996) Structure-function analysis of the motor domain of myosin. *Annu Rev Cell Dev Biol.* 12, 543-73.

Rybakova, I. N., Greaser, M. L., and Moss, R. L. (2011) Myosin binding protein C interaction with actin: characterization and mapping of the binding site. *J Biol Chem.* 286, 2008-2016.

Saber, W., Begin, K. J., Warshaw, D. M., and VanBuren, P. (2008) Cardiac myosin binding protein-C modulates actomyosin binding and kinetics in the in vitro motility assay. *J Mol Cell Cardiol.* 44, 1053-1061.

Sata, M., Stafford, W., Mabuchi, K., and Ikebe, M. (1997) The motor domain and the regulatory domain of myosin solely dictate enzymatic activity and phosphorylation-dependent regulation, respectively. *Proc. Natl. Acad. Sci. U.S.A.* 94, 91-96.

Selvin, P. R. (1995) Fluorescence resonance energy transfer. Methods Enzymol. 246, pp. 300-334.

Semsarian, C., Ingles, J., Maron, M. S., Maron, B. J. (2015) New perspectives on the prevalence of hypertrophic cardiomyopathy. *J Am. Coll. Cardiol.* 65, 1249-1254.

Semsarian, C., Ingles, J., Wilde, A. A. (2015) Sudden cardiac death in the young: the molecular autopsy and a practical approach to surviving relatives. *Eur. Heart J.* 36, 1290-1296.

Shaffer, J. F., et al. (2009) The myosin-binding protein C motif binds to F-actin in a phosphorylation-sensitive manner. *J Biol Chem.* 284, 12318-12327.

Shin, M., et al. (2018) Targeting protein and peptide therapeutics to the heart via tannic acid modification. Nat Biomed Eng. (5):304-317.

Siemankowski, R. F., et al. (1985) ADP ADP Dissociation from actomyosin subfragment 1 is sufficiently slow to limit the unloaded shortening velocity in vertebrate muscle. *Proc. Natl. Acad. Sci. U.S.A.* 82, 658-662.

Singh, R. R. (2017) "Stability of myosin subfragment-2 modulates the force produced by acto-myosin interaction of striated muscle." University of North Texas. (Dissertation under Dr. Root, available online since Jan. 27, 2018.).

Singh, R. R., et al. (2018) Whole length myosin binding protein C stabilizes myosin S2 flexibility as measured by gravitational force spectroscopy. Arch Biochem Biophys. 638:41-51.

Sommese, R. F., et al. (2013) Molecular consequences of the R453C hypertrophic cardiomyopathy mutation on human β-cardiac myosin motor function. *Proc Natl Acad Sci USA*. 110, 12607-12612.

Spudich, J. A. (2014) Hypertrophic and dilated cardiomyopathy: Four decades of basic research on muscle lead to potential therapeutic approaches to these devastating genetic diseases. *Biophys. J.* 106, 1236-1249.

Spudich, J. A. and Watt, S. (1971) The regulation of rabbit skeletal muscle contraction. I. Biochemical studies of the interaction of the tropomyosin-troponin complex with actin and the proteolytic fragments of myosin. *J. Biol. Chem.* 246, 4866-4871.

Starr, R., and Offer, G. (1978) The interaction of C-protein with heavy meromyosin and subfragment-2. *Biochem. J.* 171, 813-816.

Sugi, H, Kobayashi, T., Gross, T., Noguchi, K., Karr, T., and Harrington, W. F. (1992) Contraction characteristics and ATPase activity of skeletal muscle fibers in the presence of antibody to myosin subfragment 2. *Proc. Natl. Acad. Sci. U.S.A.* 89, 6134-6137.

Sutoh, K., Sutoh, K., Karr, T. and Harrington, W. F. (1978) Isolation and physico-chemical properties of a high molecular weight subfragment-2 of myosin. *J. Mol. Biol.* 126, 1-22.

Taei, N. (published, or first available to the public, Apr. 23, 2014) "Synthetic peptides model instability of cardiac myosin subfragment-2." University of North Texas. (Thesis under Dr. Douglas Root)

Taylor, E. W. (1977) Transient phase of adenosine triphosphate hydrolysis by myosin, heavy meromyosin, and subfragment 1. *Biochemistry* 16, 732-740.

Tesson, F., Richard, P., Charron, P., Mathieu, B., Cruaud, C., Carrier, L., Dubourg, O., Lautié, N., Desnos, M., Millaire, A., Isnard, R., Hagege, A. A., Bouhour, J. B., Bennaceur, M., Hainque, B., Guicheney, P., Schwartz, K., and Komajda, M. (1998) Genotype-phenotype analysis in four families with mutations in beta-myosin heavy chain gene responsible for familial hypertrophic cardiomyopathy. *Hum Mutat.* 12, 385-392.

Trybus, K. M., Huiatt, T. W., and Lowey, S. (1982) A bent monomeric conformation of myosin from smooth muscle. *Proc. Natl. Acad. Sci. U.S.A.* 79, 6151-6155.

Tsuchiya, T., Tanaka, H., Shirakawa, I., Karr, T., and Sugi, H. (1998) Evidence for the essential role of myosin subfragment-2 in the ATP-dependent actin-myosin sliding in muscle contraction. *Jpn. J. Physiol.* 48, 383-387.

Vibert, P., Craig, R., and Lehman, W. (1997). Steric-model for activation of muscle thin filaments. *J. Mol. Biol.* 266, 8-14.

Volkmann, N., Lui, H., Hazelwood, L., Trybus, K. M., Lowey, S., and Hanein, D. (2007) The R403Q myosin mutation implicated in familial hypertrophic cardiomyopathy causes disorder at the actomyosin interface. *PLoS One.* 2, e1123.

Voller, A., Bartlett, A., and Bidwell, D. E. (1978) Enzyme immunoassays with special reference to ELISA techniques. *J Clin Pathol.* 31, 507-520.

Waldmüller, S., et al. (2003) Novel deletions in MYH7 and MYBPC3 identified in Indian families with familial hypertrophic cardiomyopathy. *J Mol Cell Cardiol.* 35, 623-636.

Walker, J. M. (1996) The Protein Protocols Handbook. p 779-p 780. Human Press, INC., New Jersey.

Walker, J. M. (1996) The protein protocols handbook. p 779-p 780. Human Press, INC., New Jersey.

Walker, M., Knight, P., and Trinick, J. (1985) Negative staining of myosin molecules. *J Mol Biol.* 184, 535-542.

Walker, S. M., and Schrodt, G. R. (1967) Contraction of skeletal muscle. *Am J Phys Med.* 46, 151-72

Wang, K. (1985) Sarcomere—associated cytoskelatal lattices in striated muscle. *Cell Muscle Motil.,* 315-369. Springer U S, New York.

Warrick, H. M., and Spudich, J. A. (1987) Myosin structure and function in cell motility. *Annu Rev Cell Biol.* 3, 379-421.

Weisberg, A., and Winegrad. S. (1996) Alteration of myosin cross bridges by phosphorylation of myosin-binding protein C in cardiac muscle. *Proc. Natl. Acad. Sci.* U.S.A. 93, 8999-9003.

Weith, A. E., et al. (2012) The extent of cardiac myosin binding protein-C phosphorylation modulates actomyosin function in a graded manner. *J Muscle Res Cell Motil.* 33, 449-459.

White, H. D. and Taylor, E. W. (1976) Energetics and mechanism of actomyosin adenosine triphosphatase. *Biochemistry* 15, 5818-5826.

Whitten, A. E., et al. (2008) Cardiac myosin-binding protein C decorates F-actin: implications for cardiac function. *Proc. Natl. Acad. Sci. U.S.A.* 105, 18360-18365.

Witjas-Paalberends, E. R., et al. (2014) Faster cross-bridge detachment and increased tension cost in human hypertrophic cardiomyopathy with the R403Q MYH7 mutation. *J Physiol.* 592, 3257-3272.

Woodhead, J. L., et al. (2005) Atomic model of a myosin filament in the relaxed state. *Nature* 436, 1195-1199.

Xu, J., and Root, D. D. (2000) Conformational selection during weak binding at the actin and myosin interface. *Biophys J.* 79, 1498-1510.

Yorde, D. E., et al. (1976). Competitive enzyme linked immunoassay with use of soluble enzyme/antibody immune complexes for labelling. I. Measurement of human choriogonadotropin. *Clin. Chem.,* 22, 1372-1377.

A number of embodiments of the invention have been described. Nevertheless, it can be understood that various modifications may be made without departing from the spirit and scope of the invention. Accordingly, other embodiments are within the scope of the following claims.

What is claimed is:

1. A method for:

treating, ameliorating or protecting, slowing the progress of, abating or decreasing one or more symptoms of heart failure, optionally chronic congestive heart failure (CHF))

in an individual or a patient in need thereof, the method comprising administering a peptide modulator of myosin subfragment-2 coiled coil stability, or a nucleic acid encoding the peptide modulator, to the individual or patient in need thereof, wherein the peptide modulator of myosin subfragment-2 coiled coil stability comprises a peptide or polypeptide comprising:

(a) an amino acid sequence EMNERLEDEREMKAEL-TAK (SEQ ID NO: 1); or (b) an amino acid sequence KKKKKKKKFKAKKKKKK (SEQ ID NO: 3).

2. The method of claim 1, wherein the nucleic acid encoding the peptide modulator of myosin subfragment-2 coiled coil stability is operatively linked to a transcriptional regulatory sequence.

3. The method of claim 2, wherein an expression vehicle, a vector or a recombinant virus having the nucleic acid encoding the peptide modulator of myosin subfragment-2 coiled coil stability contained therein is administered to the individual or patient in need thereof.

4. The method of claim 3, wherein the expression vehicle, vector, recombinant virus, or equivalent is or comprises: an adeno-associated virus (AAV), a lentiviral vector or an adenovirus vector, an AAV serotype AAV5, AAV6, AAV8 or AAV9, a rhesus-derived AAV, or the rhesus-derived AAV AAVrh.10hCLN2, an AAV capsid mutant or AAV hybrid serotype, an organ-tropic AAV, optionally, cardiac or skeletal muscle-tropic, wherein optionally the AAV is engineered to increase efficiency in targeting a specific cell type that is non-permissive to a wild type (wt) AAV and/or to improve efficacy in infecting only a cell type of interest, and optionally the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid.

5. The method of claim 3, wherein a cell having the expression vehicle, a vector or a recombinant virus contained therein is administered to the individual or patient in need thereof.

6. The method of claim 2, wherein a cell having the nucleic acid encoding the peptide modulator of myosin subfragment-2 coiled coil stability contained therein is administered to the individual or patient in need thereof.

7. The method of claim 1, wherein: the peptide modulator or nucleic acid encoding the peptide modulator is administered or delivered to the individual or the patient in need thereof, by oral, intramuscular (IM) injection, by intravenous (IV) injection, by subcutaneous (SC) or intradermal injection, by intrathecal injection, by intra-arterial (IA) injection, by intracoronary injection, by inhalation, by aerosol, or by a biolistic particle delivery system, or by using a "gene gun", air pistol or by a gene gun.

8. The method of claim 1, wherein:

(a) the individual or patient in need thereof is administered the nucleic acid encoding the peptide modulator and a stimulus or signal that activates or induces expression of the peptide modulator, wherein the administered nucleic acid comprises and is operative linked to a promoter that is activated or induced by the stimulus or signal;

(b) the method of (a), wherein the promoter is a cardiac cell-specific promoter;

(c) the individual, patient or subject is administered a stimulus or signal that induces synthesis of a natural or a synthetic activator of the peptide modulator, wherein optionally the natural activator is an endogenous transcription factor;

(d) the method of (c), wherein the synthetic activator is a zinc-finger DNA binding protein designed to specifically and selectively turn on an endogenous or exogenous target gene, wherein optionally the endogenous target is a gene peptide modulator of myosin subfragment-2 coiled coil stability expressing nucleic acid or gene or an activator of a peptide modulator of myosin subfragment-2 coiled coil stability expressing nucleic acid or gene, or an activator of a promoter operatively linked to a peptide modulator of myosin subfragment-2 coiled coil stability-expressing nucleic acid or gene;

(e) the method of any of (a) to (c), wherein the stimulus or signal comprises a biologic, a light, a chemical or a pharmaceutical stimulus or signal;

(f) the individual or patient in need thereof is administered a stimulus or signal that stimulates or induces expression of a post-transcriptional activator of a peptide modulator of myosin subfragment-2 coiled coil stability-expressing nucleic acid or gene, or an activator of a promoter operatively linked to a peptide modulator of myosin subfragment-2 coiled coil stability-expressing nucleic acid or gene, or (g) the individual or patient in need thereof is administered a stimulus or signal that inhibits or induces inhibition of a transcriptional repressor or a post-transcriptional repressor of a peptide modulator of myosin subfragment-2 coiled coil stability expressing nucleic acid or gene.

9. The method of claim 1, wherein the individual or patient in need thereof is administered a chemical or a pharmaceutical that induces expression of the peptide modulator, or induces expression of a regulated or inducible promoter operatively linked to the nucleic acid encoding the peptide modulator, and the chemical or pharmaceutical comprises: an oral antibiotic, a doxycycline, a rapamycin; or a tet-regulation system using doxycycline to induce expression of the peptide modulator of a myosin subfragment-2 coiled coil stability-expressing nucleic acid or gene.

10. The method of claim 1, wherein the peptide modulator is formulated in a liquid, a gel, a hydrogel, a powder or an aqueous or a saline formulation.

11. The method of claim 1, wherein the peptide modulator or the nucleic acid encoding the peptide modulator is formulated in a vesicle, liposome, nanoparticle or nanolipid particle (NLP).

12. The method of claim 1, wherein the nucleic acid encoding the peptide modulator is contained in an expression vehicle, a vector, or a recombinant virus, which is formulated in an isolated or cultured cell.

13. The method of claim 12, wherein the cell is a mammalian cell, a cardiac cell, or a human cell, a non-human primate cell, a monkey cell, a mouse cell, a rat cell, a guinea pig cell, a rabbit cell, a hamster cell, a goat cell, a bovine cell, an equine cell, an ovine cell, a canine cell or a feline cell.

14. The method of claim 1, wherein the peptide modulator or the nucleic acid encoding the peptide modulator is formulated as a pharmaceutical or sterile formulation.

15. The method of claim 1, wherein the peptide modulator or the nucleic acid encoding the peptide modulator is formulated or delivered with, on, or in conjunction with a product of manufacture, an artificial organ or an implant.

16. The method of claim 1, wherein the peptide modulator of myosin subfragment-2 coiled coil stability comprises a peptide or polypeptide consists of:

(a) an amino acid sequence EMNERLEDEREMKAEL-TAK (SEQ ID NO:1), with L or D amino acid isomers; or (b)    an    amino    acid    sequence KKKKKKKKFKAKKKKKK (SEQ ID NO:3), with L or D amino acid isomers.

17. The method of claim 1, wherein the peptide modulator of myosin subfragment-2 coiled coil stability comprises a peptide or polypeptide comprising an amino acid sequence EMNERLEDEREMKAELTAK (SEQ ID NO:1).

18. The method of claim 1, wherein the peptide modulator of myosin subfragment-2 coiled coil stability comprises a peptide or polypeptide comprising an amino acid sequence KKKKKKKKFKAKKKKKK (SEQ ID NO:3).

* * * * *

SEQUENCE LISTING

<160> NUMBER OF SEQ ID NOS: 15

<210> SEQ ID NO 1
<211> LENGTH: 19
<212> TYPE: PRT

-continued

```
<213> ORGANISM: Artificial Sequence
<220> FEATURE:
<223> OTHER INFORMATION: Synthetic

<400> SEQUENCE: 1

Glu Met Asn Glu Arg Leu Glu Asp Glu Arg Glu Met Lys Ala Glu Leu
1               5                   10                  15

Thr Ala Lys

<210> SEQ ID NO 2
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: misc_feature
<222> LOCATION: (6)..(20)
<223> OTHER INFORMATION: "Lys" may or may not be present
<220> FEATURE:
<221> NAME/KEY: misc_feature
<222> LOCATION: (29)..(43)
<223> OTHER INFORMATION: "Lys" may or may not be present

<400> SEQUENCE: 2

Lys Lys Lys Lys Lys Lys Lys Lys Lys Lys Lys Lys Lys Lys Lys Lys
1               5                   10                  15

Lys Lys Lys Lys Phe Lys Ala Lys Lys Lys Lys Lys Lys Lys Lys Lys
            20                  25                  30

Lys Lys Lys Lys Lys Lys Lys Lys Lys Lys Lys
        35                  40

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Lys Lys Lys Lys Lys Lys Lys Lys Phe Lys Ala Lys Lys Lys Lys Lys
1               5                   10                  15

Lys

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Arg Arg Arg Arg Trp Trp Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5
```

-continued

```
Cys Ala Arg Ser Lys Asn Lys Asp Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Cys Arg Lys Asp Lys Cys
1               5

<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Glu Met Asn Glu Arg Leu Glu Asp Glu Glu Glu Met Asn Ala Glu Leu
1               5                   10                  15

Thr Ala Lys

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Glu Met Asn Lys Arg Leu Glu Asp Glu Glu Glu Met Asn Ala Glu Leu
1               5                   10                  15

Thr Ala Lys

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Glu Met Asn Glu Arg Leu Glu Asp Glu Glu Met Asn Ala Glu Leu Thr
1               5                   10                  15

Ala Lys

<210> SEQ ID NO 10
<211> LENGTH: 19
<212> TYPE: PRT
<213> ORGANISM: Artificial Sequence
<220> FEATURE:
<223> OTHER INFORMATION: Synthetic

<400> SEQUENCE: 10

Glu Val Thr Glu Arg Ala Glu Asp Glu Glu Glu Ile Asn Ala Glu Leu
1               5                   10                  15

Thr Ala Lys

<210> SEQ ID NO 11
```

```
<211> LENGTH: 21
<212> TYPE: PRT
<213> ORGANISM: Artificial Sequence
<220> FEATURE:
<223> OTHER INFORMATION: Synthetic

<400> SEQUENCE: 11

Glu Met Glu Ala Arg Leu Glu Glu Glu Asp Arg Gly Gln Gln Leu
1               5                   10                  15

Gln Ala Glu Arg Lys
            20

<210> SEQ ID NO 12
<211> LENGTH: 36
<212> TYPE: PRT
<213> ORGANISM: Artificial Sequence
<220> FEATURE:
<223> OTHER INFORMATION: Synthetic

<400> SEQUENCE: 12

Lys Ile Gln Leu Glu Ala Lys Val Lys Glu Met Asn Glu Arg Leu Glu
1               5                   10                  15

Asp Glu Glu Glu Met Asn Ala Glu Leu Thr Ala Lys Lys Arg Lys Leu
            20                  25                  30

Glu Asp Glu Cys
        35

<210> SEQ ID NO 13
<211> LENGTH: 35
<212> TYPE: PRT
<213> ORGANISM: Artificial Sequence
<220> FEATURE:
<223> OTHER INFORMATION: Synthetic

<400> SEQUENCE: 13

Lys Ile Gln Leu Glu Ala Lys Val Lys Glu Met Asn Glu Arg Leu Glu
1               5                   10                  15

Asp Glu Glu Met Asn Ala Glu Leu Thr Ala Lys Lys Arg Lys Leu Glu
            20                  25                  30

Asp Glu Cys
        35

<210> SEQ ID NO 14
<211> LENGTH: 36
<212> TYPE: PRT
<213> ORGANISM: Artificial Sequence
<220> FEATURE:
<223> OTHER INFORMATION: Synthetic

<400> SEQUENCE: 14

Lys Gln Glu Leu Glu Glu Ile Leu His Glu Met Glu Ala Arg Leu Glu
1               5                   10                  15

Glu Glu Glu Asp Arg Gly Gln Gln Leu Gln Ala Glu Arg Lys Lys Met
            20                  25                  30

Ala Gln Gln Cys
        35

<210> SEQ ID NO 15
<211> LENGTH: 36
<212> TYPE: PRT
<213> ORGANISM: Artificial Sequence
<220> FEATURE:
<223> OTHER INFORMATION: Synthetic
```

-continued

```
<400> SEQUENCE: 15

Lys Ile Gln Leu Glu Ala Lys Ile Lys Glu Val Thr Glu Arg Ala Glu
1               5                   10                  15

Asp Glu Glu Glu Ile Asn Ala Glu Leu Thr Ala Lys Lys Arg Lys Leu
                20                  25                  30

Glu Asp Glu Cys
        35
```